(12) United States Patent
Freel et al.

(10) Patent No.: US 10,982,152 B2
(45) Date of Patent: Apr. 20, 2021

(54) DEMETALLIZATION OF LIQUID BIOMASS

(71) Applicant: Ensyn Renewables, Inc., Wilmington, DE (US)

(72) Inventors: Barry A. Freel, Ottawa (CA); Josh Normand, Wilmington, DE (US); Timothy A. Brandvold, Des Plaines, IL (US); Stanley J. Frey, Des Plaines, IL (US); Doug Clarke, Richmond (CA)

(73) Assignee: Ensyn Renewables, Inc., Wilmington, DE (US)

( * ) Notice: Subject to any disclaimer, the term of this patent is extended or adjusted under 35 U.S.C. 154(b) by 0 days.

(21) Appl. No.: 16/517,245

(22) Filed: Jul. 19, 2019

(65) Prior Publication Data

US 2020/0010764 A1    Jan. 9, 2020

Related U.S. Application Data

(63) Continuation of application No. 15/851,080, filed on Dec. 21, 2017, now Pat. No. 10,400,176.

(60) Provisional application No. 62/440,252, filed on Dec. 29, 2016.

(51) Int. Cl.
| | |
|---|---|
| *C10C 5/00* | (2006.01) |
| *C10B 53/02* | (2006.01) |
| *C12P 7/46* | (2006.01) |
| *C07C 7/09* | (2006.01) |
| *C10G 7/00* | (2006.01) |

(52) U.S. Cl.
CPC .............. *C10B 53/02* (2013.01); *C07C 7/09* (2013.01); *C10G 7/00* (2013.01); *C12P 7/46* (2013.01); *C10G 2300/1011* (2013.01); *C10G 2300/205* (2013.01); *Y02P 20/584* (2015.11)

(58) Field of Classification Search
CPC ... C10B 53/02; C12P 7/46; C07C 7/09; C10G 7/00; C10G 2300/205; C10G 2300/1011; Y02P 20/584; C10C 5/00
USPC .......................................................... 422/608
See application file for complete search history.

(56) References Cited

U.S. PATENT DOCUMENTS

| | | |
|---|---|---|
| 1,252,072 A | 1/1918 | Abbot |
| 2,205,757 A | 6/1940 | Wheat |
| 2,318,555 A | 5/1943 | Ruthruff |
| 2,326,525 A | 8/1943 | Diwoky |

(Continued)

FOREIGN PATENT DOCUMENTS

| | | |
|---|---|---|
| BR | 8304158 | 7/1984 |
| BR | 8304794 | 4/1985 |

(Continued)

OTHER PUBLICATIONS

AccessScience Dictionary, "ebullating-bed reactor," http://www.accessscience.com, last visited Jul. 15, 2014.

(Continued)

*Primary Examiner* — Huy Tram Nguyen
(74) *Attorney, Agent, or Firm* — Jones Day

(57) ABSTRACT

Methods, processes, systems, or apparatus are provided to remove contaminants such as metals and chlorine present in a pyrolysis stream to form reduced-contaminant liquid biomass. In certain embodiments, for example, a metal chelating agent is dissolved into a metal-containing pyrolysis stream condensate to form metal chelate complex, followed by filtering to obtain the reduced-contaminant liquid biomass.

19 Claims, 5 Drawing Sheets

(56) References Cited

U.S. PATENT DOCUMENTS

| | | |
|---|---|---|
| 2,328,202 A | 8/1943 | Doerner |
| 2,380,098 A | 7/1945 | Doerner |
| 2,492,948 A | 1/1950 | Berger |
| 2,566,353 A | 9/1951 | Mills |
| 2,696,979 A | 12/1954 | Berge |
| 2,884,303 A | 4/1959 | William |
| 2,984,602 A | 5/1961 | Nevens et al. |
| 3,130,007 A | 4/1964 | Breck |
| 3,270,807 A | 9/1966 | Steadman |
| 3,309,356 A | 3/1967 | Esterer |
| 3,313,726 A | 4/1967 | Campbell et al. |
| 3,444,048 A | 5/1969 | Schmeling et al. |
| 3,445,549 A | 5/1969 | Hakulin |
| 3,467,502 A | 9/1969 | Davis |
| 3,589,313 A | 6/1971 | Smith et al. |
| 3,593,968 A | 7/1971 | Geddes |
| 3,622,505 A * | 11/1971 | Tilley .................. C10G 21/003 208/252 |
| 3,694,346 A | 9/1972 | Blaser et al. |
| 3,696,022 A | 10/1972 | Hutchings |
| 3,760,870 A | 9/1973 | Guetlhuber |
| 3,776,533 A | 12/1973 | Vlnaty |
| 3,807,090 A | 4/1974 | Moss |
| 3,814,176 A | 6/1974 | Seth |
| 3,853,498 A | 12/1974 | Bailie |
| 3,876,533 A | 4/1975 | Myers |
| 3,890,111 A | 6/1975 | Knudsen |
| 3,907,661 A | 9/1975 | Gwyn et al. |
| 3,925,024 A | 12/1975 | Hollingsworth et al. |
| 3,927,996 A | 12/1975 | Knudsen et al. |
| 3,959,420 A | 5/1976 | Geddes et al. |
| 4,003,829 A | 1/1977 | Burger et al. |
| 4,032,305 A | 6/1977 | Squires |
| 4,039,290 A | 8/1977 | Inada et al. |
| 4,052,265 A | 10/1977 | Kemp |
| 4,064,018 A | 12/1977 | Choi |
| 4,064,043 A | 12/1977 | Kollman |
| 4,085,030 A | 4/1978 | Green et al. |
| 4,095,960 A | 6/1978 | Schuhmann |
| 4,101,414 A | 7/1978 | Kim et al. |
| 4,102,773 A | 7/1978 | Green et al. |
| 4,103,902 A | 8/1978 | Steiner et al. |
| 4,138,020 A | 2/1979 | Steiner et al. |
| 4,145,274 A | 3/1979 | Green et al. |
| 4,147,593 A | 4/1979 | Frischmath et al. |
| 4,153,514 A | 5/1979 | Garrett et al. |
| 4,157,245 A | 6/1979 | Mitchell et al. |
| 4,159,682 A | 7/1979 | Fitch |
| 4,165,717 A | 8/1979 | Reh et al. |
| 4,204,915 A | 5/1980 | Kurata et al. |
| 4,210,492 A | 7/1980 | Roberts |
| 4,219,537 A | 8/1980 | Steiner |
| 4,225,415 A | 9/1980 | Mirza et al. |
| 4,233,119 A | 11/1980 | Meyers et al. |
| 4,245,693 A | 1/1981 | Cheng |
| 4,255,162 A | 3/1981 | Moss |
| 4,258,005 A | 3/1981 | Ito et al. |
| 4,260,421 A | 4/1981 | Brown et al. |
| 4,260,473 A * | 4/1981 | Bauer .................. C10G 1/045 201/2.5 |
| 4,272,402 A | 6/1981 | Mayes |
| 4,279,207 A | 7/1981 | Wormser |
| 4,280,879 A | 7/1981 | Taciuk |
| 4,284,616 A | 8/1981 | Solbakken et al. |
| 4,298,453 A | 11/1981 | Schoennagel et al. |
| 4,300,009 A | 11/1981 | Haag et al. |
| 4,301,771 A | 11/1981 | Jukkola et al. |
| 4,306,619 A | 12/1981 | Trojani |
| 4,308,411 A | 12/1981 | Frankiewicz |
| 4,311,670 A | 1/1982 | Nieminen et al. |
| 4,317,703 A | 3/1982 | Bowen et al. |
| 4,321,096 A | 3/1982 | Dobbin |
| 4,324,637 A | 4/1982 | Durai-swamy |
| 4,324,641 A | 4/1982 | Durai-Swamy |
| 4,324,642 A | 4/1982 | Durai-swamy |
| 4,324,644 A | 4/1982 | Durai-swamy |
| 4,325,327 A | 4/1982 | Kantesaria et al. |
| 4,334,893 A | 6/1982 | Lang |
| 4,336,128 A | 6/1982 | Tamm |
| 4,341,598 A | 7/1982 | Green |
| 4,344,770 A | 8/1982 | Capener et al. |
| 4,364,796 A | 12/1982 | Ishii et al. |
| 4,373,994 A | 2/1983 | Lee |
| 4,375,950 A | 3/1983 | Durley |
| 4,415,434 A | 11/1983 | Hargreaves et al. |
| 4,422,927 A | 12/1983 | Kowalczyk |
| 4,434,726 A | 3/1984 | Jones |
| 4,443,229 A | 4/1984 | Sageman et al. |
| 4,456,504 A | 6/1984 | Spars et al. |
| 4,470,254 A | 9/1984 | Chen et al. |
| 4,482,451 A | 11/1984 | Kemp |
| 4,495,056 A | 1/1985 | Venardos et al. |
| 4,504,379 A | 3/1985 | Stuntz et al. |
| 4,524,752 A | 6/1985 | Clarke |
| 4,537,571 A | 8/1985 | Buxel et al. |
| 4,548,138 A | 10/1985 | Korenberg |
| 4,548,615 A | 10/1985 | Longchamp et al. |
| 4,552,203 A | 11/1985 | Chrysostome et al. |
| 4,574,743 A | 3/1986 | Claus |
| 4,584,064 A | 4/1986 | Ciais et al. |
| 4,584,947 A | 4/1986 | Chittick |
| 4,595,567 A | 6/1986 | Hedrick |
| 4,597,733 A | 7/1986 | Dean et al. |
| 4,597,771 A | 7/1986 | Cheng |
| 4,615,870 A | 10/1986 | Armstrong et al. |
| 4,617,693 A | 10/1986 | Meyer et al. |
| 4,645,568 A | 2/1987 | Kurps et al. |
| 4,668,243 A | 5/1987 | Schulz |
| 4,678,860 A | 7/1987 | Kuester |
| 4,684,375 A | 8/1987 | Morin et al. |
| 4,710,357 A | 12/1987 | Cetinkaya et al. |
| 4,714,109 A | 12/1987 | Tsao |
| 4,732,091 A | 3/1988 | Gould |
| 4,796,546 A | 1/1989 | Herstad et al. |
| 4,823,712 A | 4/1989 | Wormer |
| 4,828,581 A | 5/1989 | Feldmann et al. |
| 4,849,091 A | 7/1989 | Cabrera et al. |
| 4,856,460 A | 8/1989 | Weid et al. |
| 4,880,473 A | 11/1989 | Scott et al. |
| 4,881,592 A | 11/1989 | Cetinkaya |
| 4,891,459 A | 1/1990 | Knight et al. |
| 4,897,178 A | 1/1990 | Best et al. |
| 4,931,171 A | 6/1990 | Piotter |
| 4,936,230 A | 6/1990 | Feugier et al. |
| 4,940,007 A | 7/1990 | Hiltunen et al. |
| 4,942,269 A | 7/1990 | Chum et al. |
| 4,968,325 A | 11/1990 | Black et al. |
| 4,983,278 A | 1/1991 | Cha et al. |
| 4,987,178 A | 1/1991 | Shibata et al. |
| 4,988,430 A | 1/1991 | Sechrist et al. |
| 4,992,605 A | 2/1991 | Craig et al. |
| 5,009,770 A | 4/1991 | Miller et al. |
| 5,011,592 A | 4/1991 | Owen et al. |
| 5,018,458 A | 5/1991 | Mcintyre et al. |
| 5,041,209 A | 8/1991 | Cha et al. |
| 5,059,404 A | 10/1991 | Mansour et al. |
| 5,066,627 A | 11/1991 | Owen et al. |
| 5,077,252 A | 12/1991 | Owen et al. |
| 5,093,085 A | 3/1992 | Engstrom et al. |
| 5,136,117 A | 8/1992 | Paisley et al. |
| 5,151,392 A | 9/1992 | Fettis et al. |
| 5,212,129 A | 5/1993 | Lomas |
| 5,225,044 A | 7/1993 | Breu |
| 5,227,566 A | 7/1993 | Cottrell et al. |
| 5,236,688 A | 8/1993 | Watanabe et al. |
| 5,239,946 A | 8/1993 | Garcia-Mallol |
| 5,243,922 A | 9/1993 | Rehmat et al. |
| 5,264,114 A * | 11/1993 | Dunbar .................. C10G 55/04 208/289 |
| 5,281,727 A | 1/1994 | Carver et al. |
| 5,292,541 A | 3/1994 | Underwood et al. |
| 5,306,481 A | 4/1994 | Mansour et al. |
| 5,308,585 A | 5/1994 | Stroder et al. |
| 5,326,919 A | 7/1994 | Paisley et al. |

(56) References Cited

U.S. PATENT DOCUMENTS

| | | |
|---|---|---|
| 5,343,939 A | 9/1994 | Cetinkaya |
| 5,365,889 A | 11/1994 | Tang |
| 5,371,212 A | 12/1994 | Moens |
| 5,376,340 A | 12/1994 | Bayer et al. |
| 5,380,916 A | 1/1995 | Rao |
| 5,395,455 A | 3/1995 | Scott et al. |
| 5,402,548 A | 4/1995 | Adair et al. |
| 5,407,674 A | 4/1995 | Gabetta et al. |
| 5,423,891 A | 6/1995 | Taylor |
| 5,426,807 A | 6/1995 | Grimsley et al. |
| 5,478,736 A | 12/1995 | Nair |
| 5,494,653 A | 2/1996 | Paisley |
| 5,516,279 A | 5/1996 | Yap |
| 5,520,722 A | 5/1996 | Hershkowitz et al. |
| 5,536,488 A | 7/1996 | Mansour et al. |
| 5,554,347 A | 9/1996 | Busson et al. |
| 5,578,092 A | 11/1996 | Collin |
| 5,584,985 A | 12/1996 | Lomas |
| 5,605,551 A | 2/1997 | Scott et al. |
| 5,637,192 A | 7/1997 | Mansour et al. |
| 5,654,448 A | 8/1997 | Pandey et al. |
| 5,662,050 A | 9/1997 | Angelo, II et al. |
| 5,670,061 A | 9/1997 | Kowallik et al. |
| 5,686,049 A | 11/1997 | Bonifay et al. |
| 5,703,299 A | 12/1997 | Carleton et al. |
| 5,713,977 A | 2/1998 | Kobayashi |
| 5,725,738 A | 3/1998 | Brioni et al. |
| 5,728,271 A | 3/1998 | Piskorz et al. |
| 5,744,333 A | 4/1998 | Cociancich et al. |
| 5,788,784 A | 8/1998 | Koppenhoefer et al. |
| 5,792,340 A | 8/1998 | Freel et al. |
| 5,797,332 A | 8/1998 | Keller et al. |
| 5,853,548 A | 12/1998 | Piskorz et al. |
| 5,875,830 A | 3/1999 | Singer et al. |
| 5,879,079 A | 3/1999 | Hohmann et al. |
| 5,879,642 A | 3/1999 | Trimble et al. |
| 5,879,650 A | 3/1999 | Kaul et al. |
| 5,904,838 A | 5/1999 | Kalnes et al. |
| 5,915,311 A | 6/1999 | Muller et al. |
| 5,961,786 A | 10/1999 | Freel et al. |
| 5,969,165 A | 10/1999 | Liu |
| 6,002,025 A | 12/1999 | Page et al. |
| 6,011,187 A | 1/2000 | Horizoe et al. |
| 6,033,555 A | 3/2000 | Chen et al. |
| 6,106,702 A | 8/2000 | Sohn et al. |
| 6,113,862 A | 9/2000 | Jorgensen et al. |
| 6,117,199 A | 9/2000 | Ruottu |
| 6,123,833 A | 9/2000 | Sechrist et al. |
| 6,133,328 A | 10/2000 | Lightner |
| 6,133,499 A | 10/2000 | Horizoe et al. |
| 6,139,805 A | 10/2000 | Nagato et al. |
| 6,149,765 A | 11/2000 | Mansour et al. |
| 6,190,542 B1 | 2/2001 | Comolli et al. |
| 6,193,837 B1 | 2/2001 | Agblevor et al. |
| 6,237,541 B1 | 5/2001 | Alliston et al. |
| 6,286,443 B1 | 9/2001 | Fujinami et al. |
| 6,339,182 B1 | 1/2002 | Munson et al. |
| 6,497,199 B2 | 1/2002 | Yamada et al. |
| 6,390,185 B1 | 5/2002 | Proeschel |
| 6,398,921 B1 | 6/2002 | Moraski |
| 6,452,024 B1 | 9/2002 | Bui-Khac et al. |
| 6,455,015 B1 | 9/2002 | Kilroy |
| 6,485,841 B1 | 11/2002 | Freel et al. |
| 6,494,153 B1 | 12/2002 | Lyon |
| 6,547,957 B1 | 4/2003 | Sudhakar et al. |
| 6,555,649 B2 | 4/2003 | Giroux et al. |
| 6,656,342 B2 | 12/2003 | Smith et al. |
| 6,660,157 B2 | 12/2003 | Que et al. |
| 6,676,828 B1 | 1/2004 | Galiasso et al. |
| 6,680,137 B2 | 1/2004 | Paisley et al. |
| 6,743,746 B1 | 6/2004 | Prilutsky et al. |
| 6,759,562 B2 | 7/2004 | Gartside et al. |
| 6,768,036 B2 | 7/2004 | Lattner et al. |
| 6,776,607 B2 | 8/2004 | Nahas et al. |
| 6,808,390 B1 | 10/2004 | Fung |
| 6,814,940 B1 | 11/2004 | Hiltunen et al. |
| 6,844,420 B1 | 1/2005 | Freel et al. |
| 6,875,341 B1 | 4/2005 | Bunger et al. |
| 6,911,057 B2 | 6/2005 | Lyon |
| 6,960,325 B2 | 11/2005 | Kao et al. |
| 6,962,676 B1 | 11/2005 | Hyppaenen |
| 6,988,453 B2 | 1/2006 | Cole et al. |
| 7,004,999 B2 | 2/2006 | Johnson et al. |
| 7,022,741 B2 | 4/2006 | Jiang et al. |
| 7,026,262 B1 | 4/2006 | Palmas et al. |
| 7,101,463 B1 | 9/2006 | Weinecke et al. |
| 7,202,389 B1 | 4/2007 | Brem |
| 7,214,252 B1 | 5/2007 | Krumm et al. |
| 7,226,954 B2 | 6/2007 | Tavasoli et al. |
| 7,240,639 B2 | 7/2007 | Hyppaenen et al. |
| 7,247,233 B1 | 7/2007 | Hedrick et al. |
| 7,262,331 B2 | 8/2007 | van de Beld et al. |
| 7,263,934 B2 | 9/2007 | Copeland et al. |
| 7,285,186 B2 | 10/2007 | Tokarz |
| 7,319,168 B2 | 1/2008 | Sanada |
| 7,473,349 B2 | 1/2009 | Keckler et al. |
| 7,476,774 B2 | 1/2009 | Umansky et al. |
| 7,479,217 B2 | 1/2009 | Pinault et al. |
| 7,491,317 B2 | 2/2009 | Meier et al. |
| 7,563,345 B2 | 7/2009 | Tokarz |
| 7,572,362 B2 | 8/2009 | Freel et al. |
| 7,572,365 B2 | 8/2009 | Freel et al. |
| 7,578,927 B2 | 8/2009 | Marker et al. |
| 7,625,432 B2 | 12/2009 | Gouman et al. |
| 7,811,340 B2 | 10/2010 | Bayle et al. |
| 7,897,124 B2 | 3/2011 | Gunnerman et al. |
| 7,905,990 B2 | 3/2011 | Freel |
| 7,943,014 B2 | 5/2011 | Berruti et al. |
| 7,956,224 B2 | 6/2011 | Elliott et al. |
| 7,960,598 B2 | 6/2011 | Spilker et al. |
| 7,982,075 B2 | 7/2011 | Marker et al. |
| 7,998,315 B2 | 8/2011 | Bridgwater et al. |
| 7,998,455 B2 | 8/2011 | Abbas et al. |
| 7,999,142 B2 | 8/2011 | Kalnes et al. |
| 7,999,143 B2 | 8/2011 | Marker et al. |
| 8,043,391 B2 | 10/2011 | Dinjus et al. |
| 8,057,641 B2 | 11/2011 | Bartek et al. |
| 8,097,090 B2 | 1/2012 | Freel et al. |
| 8,097,216 B2 | 1/2012 | Beech et al. |
| 8,147,766 B2 | 4/2012 | Spilker et al. |
| 8,153,850 B2 | 4/2012 | Hall |
| 8,202,332 B2 | 6/2012 | Agblevor |
| 8,207,385 B2 | 6/2012 | O'Connor et al. |
| 8,217,211 B2 | 7/2012 | Agrawal et al. |
| 8,277,643 B2 | 10/2012 | Huber et al. |
| 8,288,600 B2 | 10/2012 | Bartek et al. |
| 8,292,977 B2 | 10/2012 | Suda et al. |
| 8,304,592 B2 | 11/2012 | Luebke |
| 8,314,275 B2 | 11/2012 | Brandvold |
| 8,329,967 B2 | 12/2012 | Brandvold et al. |
| 8,404,910 B2 | 3/2013 | Kocal et al. |
| 8,499,702 B2 | 8/2013 | Palmas et al. |
| 8,519,203 B2 | 8/2013 | Marinangeli et al. |
| 8,519,205 B2 | 8/2013 | Frey et al. |
| 8,524,087 B2 | 9/2013 | Frey et al. |
| 8,575,408 B2 | 11/2013 | Marker et al. |
| 8,715,490 B2 | 5/2014 | Brandvold et al. |
| 8,726,443 B2 | 5/2014 | Freel et al. |
| 8,940,060 B2 | 1/2015 | Baird et al. |
| 8,961,743 B2 | 2/2015 | Freel |
| 9,044,727 B2 | 6/2015 | Kulprathipanja et al. |
| 9,127,208 B2 | 9/2015 | Boulard et al. |
| 9,169,444 B2 | 10/2015 | Gosslink et al. |
| 9,631,145 B2 | 4/2017 | Freel |
| 2002/0014033 A1 | 2/2002 | Langer et al. |
| 2002/0100711 A1 | 8/2002 | Freel et al. |
| 2002/0146358 A1 | 10/2002 | Smith et al. |
| 2002/0194782 A1 | 12/2002 | Paisley |
| 2003/0049854 A1 | 3/2003 | Rhodes |
| 2003/0202912 A1 | 10/2003 | Myohanen et al. |
| 2004/0069682 A1 | 4/2004 | Freel et al. |
| 2004/0182003 A1 | 9/2004 | Bayle et al. |
| 2004/0200204 A1 | 10/2004 | Dries et al. |
| 2005/0167337 A1 | 8/2005 | Bunger et al. |

(56) References Cited

U.S. PATENT DOCUMENTS

| | | |
|---|---|---|
| 2005/0209328 A1 | 9/2005 | Allgood et al. |
| 2006/0010714 A1 | 1/2006 | Carin et al. |
| 2006/0016723 A1 | 1/2006 | Tang et al. |
| 2006/0070362 A1 | 4/2006 | Dewitz et al. |
| 2006/0074254 A1 | 4/2006 | Zhang et al. |
| 2006/0101665 A1 | 5/2006 | Carin et al. |
| 2006/0112639 A1 | 6/2006 | Nick et al. |
| 2006/0130719 A1 | 6/2006 | Morin et al. |
| 2006/0147854 A1 | 7/2006 | Fullemann |
| 2006/0161036 A1 | 7/2006 | Beech et al. |
| 2006/0163053 A1 | 7/2006 | Ershag |
| 2006/0180060 A1 | 8/2006 | Crafton et al. |
| 2006/0185245 A1 | 8/2006 | Serio et al. |
| 2006/0201024 A1 | 9/2006 | Carin et al. |
| 2006/0254081 A1 | 11/2006 | Carin et al. |
| 2006/0264684 A1 | 11/2006 | Petri et al. |
| 2007/0000809 A1 | 1/2007 | Lin et al. |
| 2007/0006528 A1 | 1/2007 | Diebold et al. |
| 2007/0010588 A1 | 1/2007 | Pearson |
| 2007/0141222 A1 | 6/2007 | Binder et al. |
| 2007/0175088 A1 | 8/2007 | Selkirk |
| 2007/0205139 A1 | 9/2007 | Kulprathipanja et al. |
| 2007/0267323 A1 | 11/2007 | Varadaraj et al. |
| 2007/0272538 A1 | 11/2007 | Satchell |
| 2008/0006519 A1 | 1/2008 | Badger |
| 2008/0006520 A1 | 1/2008 | Badger |
| 2008/0029437 A1 | 2/2008 | Umansky et al. |
| 2008/0035526 A1 | 2/2008 | Hedrick et al. |
| 2008/0035528 A1 | 2/2008 | Marker |
| 2008/0050792 A1 | 2/2008 | Zmierczak et al. |
| 2008/0051619 A1 | 2/2008 | Kulprathipanja et al. |
| 2008/0081006 A1 | 4/2008 | Myers et al. |
| 2008/0086937 A1 | 4/2008 | Hazlebeck et al. |
| 2008/0161615 A1 | 7/2008 | Chapus et al. |
| 2008/0171649 A1 | 7/2008 | Jan et al. |
| 2008/0185112 A1 | 8/2008 | Argyropoulos |
| 2008/0189979 A1 | 8/2008 | Carin et al. |
| 2008/0193345 A1 | 8/2008 | Lott et al. |
| 2008/0194896 A1 | 8/2008 | Brown et al. |
| 2008/0199821 A1 | 8/2008 | Nyberg et al. |
| 2008/0230440 A1 | 9/2008 | Graham et al. |
| 2008/0236043 A1 | 10/2008 | Dinjus et al. |
| 2008/0264771 A1 | 10/2008 | Dam-Johansen et al. |
| 2008/0274017 A1 | 11/2008 | Boykin et al. |
| 2008/0274022 A1 | 11/2008 | Boykin et al. |
| 2008/0282606 A1 | 11/2008 | Plaza et al. |
| 2008/0312468 A1 | 12/2008 | Fleisher et al. |
| 2008/0312476 A1 | 12/2008 | McCall |
| 2008/0318763 A1 | 12/2008 | Anderson |
| 2009/0008292 A1 | 1/2009 | Keusenkothen et al. |
| 2009/0008296 A1 | 1/2009 | Sappok et al. |
| 2009/0031615 A1 | 2/2009 | Joshi et al. |
| 2009/0077867 A1 | 3/2009 | Marker et al. |
| 2009/0077868 A1 | 3/2009 | Brady et al. |
| 2009/0078557 A1 | 3/2009 | Tokarz |
| 2009/0078611 A1 | 3/2009 | Marker et al. |
| 2009/0082603 A1 | 3/2009 | Kalnes et al. |
| 2009/0082604 A1 | 3/2009 | Agrawal et al. |
| 2009/0084666 A1 | 4/2009 | Agrawal et al. |
| 2009/0090046 A1 | 4/2009 | O'Connor et al. |
| 2009/0090058 A1 | 4/2009 | Dam-Johansen et al. |
| 2009/0113787 A1 | 5/2009 | Elliott et al. |
| 2009/0139851 A1 | 6/2009 | Freel |
| 2009/0165378 A1 | 7/2009 | Agblevor |
| 2009/0165435 A1 | 7/2009 | Koranek |
| 2009/0183424 A1 | 7/2009 | Gorbell et al. |
| 2009/0188158 A1 | 7/2009 | Morgan |
| 2009/0193709 A1 | 8/2009 | Marker et al. |
| 2009/0208402 A1 | 8/2009 | Rossi |
| 2009/0227823 A1 | 9/2009 | Huber et al. |
| 2009/0242377 A1 | 10/2009 | Honkola et al. |
| 2009/0250376 A1 | 10/2009 | Brandvold et al. |
| 2009/0253947 A1 | 10/2009 | Brandvold et al. |
| 2009/0253948 A1 | 10/2009 | McCall et al. |
| 2009/0255144 A1 | 10/2009 | Gorbell et al. |
| 2009/0259076 A1 | 10/2009 | Simmons et al. |
| 2009/0259082 A1 | 10/2009 | Deluga et al. |
| 2009/0274600 A1 | 11/2009 | Jain et al. |
| 2009/0283442 A1 | 11/2009 | McCall et al. |
| 2009/0287029 A1 | 11/2009 | Anumakonda et al. |
| 2009/0293344 A1 | 12/2009 | O'Brien et al. |
| 2009/0293359 A1 | 12/2009 | Simmons et al. |
| 2009/0294324 A1 | 12/2009 | Brandvold et al. |
| 2009/0301930 A1 | 12/2009 | Brandvold et al. |
| 2009/0308787 A1 | 12/2009 | O'Connor et al. |
| 2009/0318737 A1 | 12/2009 | Luebke |
| 2009/0321311 A1 | 12/2009 | Marker et al. |
| 2010/0043634 A1 | 2/2010 | Shulfer et al. |
| 2010/0083563 A1 | 4/2010 | Miller |
| 2010/0083566 A1 | 4/2010 | Fredriksen et al. |
| 2010/0105970 A1 | 4/2010 | Yanik et al. |
| 2010/0133144 A1 | 6/2010 | Kokayeff et al. |
| 2010/0147743 A1 | 6/2010 | MacArthur et al. |
| 2010/0151550 A1 | 6/2010 | Nunez et al. |
| 2010/0158767 A1 | 6/2010 | Mehlberg et al. |
| 2010/0148122 A1 | 7/2010 | Breton et al. |
| 2010/0162625 A1 | 7/2010 | Mills |
| 2010/0163395 A1 | 7/2010 | Henrich et al. |
| 2010/0222620 A1 | 9/2010 | O'Connor et al. |
| 2010/0266464 A1 | 10/2010 | Sipila et al. |
| 2010/0325954 A1 | 12/2010 | Tiwari et al. |
| 2011/0013662 A1 | 1/2011 | Missalla et al. |
| 2011/0017443 A1 | 1/2011 | Collins |
| 2011/0067438 A1 | 3/2011 | Bernasconi |
| 2011/0068585 A1 | 3/2011 | Dube et al. |
| 2011/0073461 A1 | 3/2011 | Chiang et al. |
| 2011/0110849 A1 | 5/2011 | Siemons |
| 2011/0113675 A1 | 5/2011 | Fujiyama et al. |
| 2011/0120909 A1 | 5/2011 | Brandvold |
| 2011/0123407 A1 | 5/2011 | Freel |
| 2011/0132737 A1 | 6/2011 | Jadhav |
| 2011/0139597 A1 | 6/2011 | Lin |
| 2011/0146135 A1 | 6/2011 | Brandvold |
| 2011/0146140 A1 | 6/2011 | Brandvold et al. |
| 2011/0146141 A1 | 6/2011 | Frey et al. |
| 2011/0146145 A1 | 6/2011 | Brandvold et al. |
| 2011/0160505 A1 | 6/2011 | McCall |
| 2011/0182778 A1 | 7/2011 | Breton et al. |
| 2011/0201854 A1 | 8/2011 | Kocal et al. |
| 2011/0219680 A1 | 9/2011 | Fuica |
| 2011/0224471 A1 | 9/2011 | Wormsbecher et al. |
| 2011/0233042 A1 | 9/2011 | Siskin et al. |
| 2011/0239530 A1 | 10/2011 | Marinangeli et al. |
| 2011/0253600 A1 | 10/2011 | Niccum |
| 2011/0258914 A1 | 10/2011 | Banasiak et al. |
| 2011/0264084 A1 | 10/2011 | Reid |
| 2011/0277377 A1 | 11/2011 | Novak et al. |
| 2011/0278149 A1 | 11/2011 | Hornung et al. |
| 2011/0284359 A1 | 11/2011 | Sechrist et al. |
| 2012/0012039 A1 | 1/2012 | Palmas et al. |
| 2012/0017493 A1 | 1/2012 | Traynor et al. |
| 2012/0022171 A1 | 1/2012 | Frey |
| 2012/0023809 A1 | 2/2012 | Koch et al. |
| 2012/0047794 A1 | 3/2012 | Bartek et al. |
| 2012/0073185 A1 | 3/2012 | Jokela et al. |
| 2012/0137571 A1 | 6/2012 | Brady et al. |
| 2012/0137572 A1 | 6/2012 | Bartek et al. |
| 2012/0137939 A1 | 6/2012 | Kulprathipanja |
| 2012/0160741 A1 | 6/2012 | Gong et al. |
| 2012/0167454 A1 | 7/2012 | Brandvold et al. |
| 2012/0172622 A1 | 7/2012 | Kocal |
| 2012/0172643 A1 | 7/2012 | Ramirez Corredores et al. |
| 2012/0184634 A1* | 7/2012 | Chen .................. C10G 1/10 521/42 |
| 2012/0193581 A1 | 8/2012 | Goetsch et al. |
| 2012/0205289 A1 | 8/2012 | Joshi |
| 2012/0214114 A1 | 8/2012 | Kim et al. |
| 2012/0216448 A1 | 8/2012 | Ramirez Coredores et al. |
| 2012/0279825 A1 | 11/2012 | Freel et al. |
| 2012/0317871 A1 | 12/2012 | Frey et al. |
| 2013/0029168 A1 | 1/2013 | Trewella et al. |
| 2013/0062184 A1 | 3/2013 | Kulprathipanja et al. |
| 2013/0067803 A1 | 3/2013 | Kalakkunnath et al. |
| 2013/0075072 A1 | 3/2013 | Kulprathipanja et al. |

(56) References Cited

U.S. PATENT DOCUMENTS

| | | | |
|---|---|---|---|
| 2013/0078581 A1 | 3/2013 | Kulprathipanja et al. |
| 2013/0212930 A1 | 3/2013 | Naae et al. |
| 2013/0105356 A1 | 5/2013 | Dijs et al. |
| 2013/0109765 A1 | 5/2013 | Jiang et al. |
| 2013/0118059 A1 | 5/2013 | Lange et al. |
| 2013/0150637 A1 | 6/2013 | Borremans et al. |
| 2013/0152453 A1 | 6/2013 | Baird et al. |
| 2013/0152454 A1 | 6/2013 | Baird et al. |
| 2013/0152455 A1 | 6/2013 | Baird et al. |
| 2013/0195727 A1 | 8/2013 | Bull et al. |
| 2013/0267743 A1 | 10/2013 | Brandvold et al. |
| 2013/0267753 A1 | 10/2013 | Ramirez Corredores et al. |
| 2014/0001026 A1 | 1/2014 | Baird et al. |
| 2014/0140895 A1 | 5/2014 | Davydov et al. |
| 2014/0142362 A1 | 5/2014 | Davydov et al. |
| 2014/0230725 A1 | 8/2014 | Holler et al. |
| 2014/0303414 A1 | 10/2014 | Mazanec et al. |
| 2015/0004093 A1 | 1/2015 | Zhou et al. |
| 2015/0005547 A1 | 1/2015 | Freel et al. |
| 2015/0184025 A1* | 7/2015 | Talwar .................... C08L 91/00 524/705 |
| 2016/0040080 A1 | 2/2016 | Freel et al. |
| 2016/0083754 A1 | 3/2016 | Medoff et al. |
| 2018/0148652 A1* | 5/2018 | Egeberg .................. C10G 31/10 |

FOREIGN PATENT DOCUMENTS

| | | |
|---|---|---|
| CA | 1312497 | 1/1993 |
| CA | 2091373 | 9/1997 |
| CA | 2299149 | 12/2000 |
| CA | 2521829 | 3/2006 |
| CN | 1377938 | 11/2002 |
| CN | 1730177 | 2/2006 |
| CN | 101045524 | 10/2007 |
| CN | 101238197 | 8/2008 |
| CN | 101294085 | 10/2008 |
| CN | 101318622 | 12/2008 |
| CN | 101353582 | 1/2009 |
| CN | 101365770 | 2/2009 |
| CN | 101381611 | 3/2009 |
| CN | 101544901 | 9/2009 |
| CN | 101550347 | 10/2009 |
| CN | 101705105 | 5/2010 |
| CN | 101745349 | 6/2010 |
| CN | 101993712 | 3/2011 |
| CN | 102093903 | 6/2011 |
| EP | 105980 | 1/1986 |
| EP | 578503 | 1/1994 |
| EP | 676023 | 7/1998 |
| EP | 718392 | 9/1999 |
| EP | 787946 | 6/2000 |
| EP | 1420058 | 5/2004 |
| EP | 2325281 | 5/2011 |
| FI | 117512 | 11/2005 |
| FR | 879606 | 3/1943 |
| GB | 752400 | 7/1956 |
| GB | 1019133 | 2/1966 |
| GB | 1300966 | 12/1972 |
| JP | 58150793 | 9/1983 |
| JP | 1277196 | 11/1989 |
| JP | 11148625 | 6/1999 |
| JP | 2001/131560 | 5/2001 |
| JP | 2007/229548 | 9/2007 |
| JP | 2008/138188 | 6/2008 |
| SE | 9903742-6 | 1/2004 |
| WO | 81/01713 | 6/1981 |
| WO | 1991/11499 | 8/1991 |
| WO | 1992/07842 | 5/1992 |
| WO | 1992/18492 | 10/1992 |
| WO | 1993/011388 | 6/1993 |
| WO | 1994/13827 | 6/1994 |
| WO | 1997/044410 | 11/1997 |
| WO | 2001/009243 | 2/2001 |
| WO | 2001/83645 | 11/2001 |
| WO | 2002/49735 | 6/2002 |
| WO | 2006/071109 | 7/2006 |
| WO | 2007/017005 | 2/2007 |
| WO | 2007/045093 | 4/2007 |
| WO | 2007/050030 | 5/2007 |
| WO | 2007/112570 | 10/2007 |
| WO | 2007/128798 | 11/2007 |
| WO | 2008/009643 | 1/2008 |
| WO | 2008/020167 | 2/2008 |
| WO | 2008/092557 | 8/2008 |
| WO | 2009/019520 | 2/2009 |
| WO | 2009/047387 | 4/2009 |
| WO | 2009/047392 | 4/2009 |
| WO | 2009/067350 | 5/2009 |
| WO | 2009/099684 | 8/2009 |
| WO | 2009/118357 | 10/2009 |
| WO | 2009/118363 | 10/2009 |
| WO | 2009/126508 | 10/2009 |
| WO | 2009/131757 | 10/2009 |
| WO | 2010/002792 | 1/2010 |
| WO | WO 2011/119016 | 9/2011 |
| WO | 2011/146262 | 11/2011 |
| WO | 2011/159768 | 12/2011 |
| WO | 2012/009207 | 1/2012 |
| WO | 2012/012260 | 1/2012 |
| WO | 2012/018520 | 2/2012 |
| WO | 2012/062924 | 5/2012 |
| WO | 2012/078422 | 6/2012 |
| WO | 2012/088546 | 6/2012 |
| WO | 2012/115754 | 8/2012 |
| WO | 2013/043485 | 3/2013 |
| WO | 2013/090229 | 6/2013 |
| WO | 2014/031965 | 2/2014 |
| WO | 2014/210150 | 12/2014 |
| WO | 2017/001539 | 1/2017 |
| WO | 2018/017664 | 1/2018 |

OTHER PUBLICATIONS

Adam, J. "Catalytic conversion of biomass to produce higher quality liquid bio-fuels," PhD Thesis, Department of Energy and Process Engineering, The Norwegian University of Science and Technology, Trondheim (2005).

Adam, J. et al. "Pyrolysis of biomass in the presence of Al-MCM-41 type catalysts," *Fuel*, 84 (2005) 1494-1502.

Adjaye, John D. et al. "Catalytic conversion of a biomass-derived oil to fuels and chemicals I: Model compound studies and reaction pathways," *Biomass & Bioenergy*, 8:3 (1995) 131-149.

Adjaye, John D. et al. "Catalytic conversion of a biomass-derived oil to fuels and chemicals II: Chemical kinetics, parameter estimation and model predictions," *Biomass & Bioenergy*, 8:4 (1995) 265-277.

Adjaye, John D. et al. "Catalytic conversion of wood derived bio-oil to fuels and chemicals," *Studies in Surface Science and Catalysis*, 73 (1992) 301-308.

Adjaye, John D. et al. "Production of hydrocarbons by the catalytic upgrading of a fast pyrolysis bio-oil," *Fuel Process Technol*, 45:3 (1995) 161-183.

Adjaye, John D. et al. "Upgrading of a wood-derived oil over various catalysts," *Biomass & Bioenergy*, 7:1-6 (1994) 201-211.

Aho, A. et al. "Catalytic pyrolysis of woody biomass in a fluidized bed reactor; Influence of zeolites structure, Science Direct," *Fuel*, 87 (2008) 2493-2501.

Antonakou, E. et al. "Evaluation of various types of Al-MCM-41 materials as catalysts in biomass pyrolysis for the production of bio-fuels and chemicals," *Fuel*, 85 (2006) 2202-2212.

Atutxa, A. et al. "Kinetic Description of the Catalytic Pyrolysis of Biomass in a Conical Spouted Bed Reactor," *Energy Fuels*, 19:3 (2005) 765-774.

Baker, E. G. et al. "Catalytic Upgrading of Biomass Pyrolysis Oils," in Bridgwater, A. V. et al. (eds) *Research in Thermochemical Biomass Conversion*, Elsevier Science Publishers Ltd., Barking, England (1988) 883-895.

Baldauf, W. et al. "Upgrading of flash pyrolysis oil and utilization in refineries," *Biomass & Bioenergy*, 7 (1994) 237-244.

(56) References Cited

OTHER PUBLICATIONS

Baumlin, "The continuous self stirred tank reactor: measurement of the cracking kinetics of biomass pyrolysis vapours," *Chemical Engineering Science*, 60 (2005) 41-55.
Berg, "Reactor Development for the Ultrapyrolysis Process," *The Canadian Journal of Chemical Engineering*, 67 (1989) 96-101.
Bielansky, P. et al. "Catalytic conversion of vegetable oils in a continuous FCC pilot plant," *Fuel Processing Technology*, 92 (2011) 2305-2311.
Bimbela, F. et al. "Hydrogen production by catalytic steam reforming of acetic acid, a model compound of biomass pyrolysis liquids," *J. Ana App. Pyrolysis*, 79 (2007) 112-120.
Bridgwater et al. (eds) *Fast Pyrolysis of Biomass: A Handbook*, Newbury Cpl Press, Great Britain (2008) 1-13.
Bridgwater, A.V. "Principles and practices of biomass fast pyrolysis processes for liquids," *Journal of Analytical and Applied Pyrolysis*, 51 (1999) 3-22.
Bridgwater, Tony "Production of high grade fuels and chemicals from catalytic pyrolysis of biomass," *Catalysis Today*, 29 (1996) 285-295.
Bridgwater, Tony et al. "Transport fuels from biomass by thermal processing," *EU-China Workshop on Liquid Biofuels*, Beijing, China (Nov. 4-5, 2004).
Buchsbaum, A. et al. "The Challenge of the Biofuels Directive for a European Refinery," *OMW Refining and Marketing*, ERTC 9th Annual Meeting, Prague, Czech Republic (Nov. 15-17, 2004).
Carlson, T. et al. "Aromatic Production from Catalytic Fast Pyrolysis of Biomass-Derived Feedstocks," *Top Catal*, 52 (2009) 241-242.
Carlson., T. et al. "Green Gasoline by Catalytic Fast Pyrolysis of Solid Biomass Derived Compounds," *ChemSusChem*, 1 (2008) 397-400.
Cass et al. "Challenges in the Isolation of Taxanes from *Taxus canadensis* by Fast Pyrolysis, "*J Analytical and Applied Pyrolysis* 57 (2001) 275-285.
Chantal, P. D. et al. "Production of Hydrocarbons from Aspen Poplar Pyrolytic Oils over H-ZSM5," *Applied Catalysis*, 10 (1984) 317-332.
Chen, N. Y. et al. "Fluidized Upgrading of Wood Pyrolysis Liquids and Related Compounds," in Soltes, E. J. et al. (eds) *Pyrolysis Oils from Biomass*, ACS, Washington, DC (1988) 277-289.
Chinsuwan, A. et al. "An experimental investigation of the effect of longitudinal fin orientation on heat transfer in membrane water wall tubes in a circulating fluidized bed," *International Journal of Heat and Mass Transfer*, 52:5-6 (2009) 1552-1560.
Cornelissen, T. et al., "Flash co-pyrolysis of biomass with polylactic acid. Part 1: Influence on bio-oil yield and heating value," *Fuel* 87 (2008) 1031-1041.
Cousins, A. et al. "Development of a bench-scale high-pressure fluidized bed reactor and its sequential modification for studying diverse aspects of pyrolysis and gasification of coal and biomass," *Energy and Fuels*, 22:4 (2008) 2491-2503.
Cragg et al, "The Search for New Pharmaceutical Crops: Drug Discovery and Development at the National Cancer Institute," in Janick, J. and Simon, J.E. (eds) *New Crops*, Wiley, New York (1993) 161-167.
Czernik, S. et al. "Hydrogen from biomass-production by steam reforming of biomass pyrolysis oil," *Catalysis Today*, 129 (2007) 265-168.
Czernik, S. et al. "Hydrogren by Catalytic Steam Reforming of Liquid Byproducts from Biomass Thermoconversion Processes," *Ind. Eng. Chern. Res.*, 41 (2002) 4209-4215.
Dahmen, "Rapid pyrolysis for the pretreatment of biomass and generation of bioslurry as intermediate fuel", *Chemie-Ingenieur-Technik*, 79:9 (2007) 1326-1327. Language: German (Abstract only; Machine translation of Abstract).
Dandik, "Catalytic Conversion of Used Oil to Hydrocarbon Fuels in a Fractionating Pyrolysis Reactor," *Energy & Fuels*, 12 (1998) 1148-1152.
Daoust et al. "Canada Yew (*Taxus canadensis* Marsh.) and Taxanes: a Perfect Species for Field Production and Improvement through Genetic Selection," Natural Resources Canada, Canadian Forest Service, Sainte-Fov, Quebec (2003).
De Wild, P. et al. "Lignin valorisation for chemicals and (transportation) fuels via (catalytic) pyrolysis and hydrodeoxygenation," *Environ. Prog. Sustainable Energy*, 28 (2009) 461-469.
Demirbas, Ayhan "Fuel Conversional Aspects of Palm Oil and Sunflower Oil," *Energy Sources*, 25 (2003) 457-466.
Di Blasi, C. et al. "Effects of Potassium Hydroxide Impregnation of Wood Pyrolysis, American Chemical Society," *Energy & Fuels* 23 (2009) 1045-1054.
Ellioti, D. "Historical Developments in Hydroprocessing Bio-oils," *Energy & Fuels*, 21 (2007) 1792-1815.
Ensyn Technologies Inc. "Catalytic de-oxygenation of biomass-derived RTP vapors." Prepared for ARUSIA, *Agenzia Regionale Umbria per lo Sviluppo e L'Innovazione*, Perugia, Italy (Mar. 1997).
Filtration, Kirk-Othmer Encyclopedia of Chemical Technology 5th Edition. vol. 11., John Wiley & Sons, Inc., Feb. 2005.
Gayubo, A. G. et al. "Deactivation of a HZSM-5 Zeolite Catalyst in the Transformation of the Aqueous Fraction of Biomass Pyrolysis Oil into Hydrocarbons," *Energy & Fuels*, 18:6 (2004) 1640-1647.
Gayubo, A. G. et al. "Undesired components in the transformation of biomass pyrolysis oil into hydrocarbons on an HZSM-5 zeolite catalyst," *J Chem Tech Biotech*, 80 (2005) 1244-1251.
Gevert, Börjie S. et al. "Upgrading of directly liquefied biomass to transportation fuels: catalytic cracking," *Biomass* 14:3 (1987) 173-183.
Goesele, W, et al., Filtration, Wiley-VCHVerlag GmbH & Co. KGaA, Weinheim, 10.1002/14356007.b0210, 2005.
Grange, P. et al. "Hydrotreatment of pyrolysis oils from biomass: reactivity of the various categories of oxygenated compounds and preliminary techno-economical study," *Catalysis Today*, 29 (1996) 297-301.
Hama, "Biodiesel-fuel production in a packed-bed reactor using lipase-producing Rhizopus oryzae cells immobilized within biomass support particles", *Biochemical Engineering Journal*, 34 (2007) 273-278.
Hoekstra, E. et al., "Fast Pyrolysis of Biomass in a Fluidized Bed Reactor: In Situ Filtering of the Vapors," *Ind. Eng. Chern. Res.*, 48:10 (2009) 4744-4756.
Holton et al. "First Total Synthesis of Taxol. 2. Completion of the C and D Rings," *J Am Chem Soc*, 116 (1994) 1599-1600.
Horne, Patrick A. et al. "Catalytic coprocessing of biomass-derived pyrolysis vapours and methanol," *J. Analytical and Applied Pyrolysis*, 34:1 (1995) 87-108.
Horne, Patrick A. et al. "Premium quality fuels and chemicals from the fluidised bed pyrolysis of biomass with zeolite catalyst upgrading," *Renewable Energy*, 5:5-8 (1994) 810-812.
Horne, Patrick A. et al. "The effect of zeolite ZSM-5 catalyst deactivation during the upgrading of biomass-derived pyrolysis vapours," *J Analytical and Applied Pyrolysis*, 34:1 (1995) 65-85.
Huang et al. "New Taxanes from Taxus brevifolia," *J of Natural Products*, 49 (1986) 665-669.
Huffman, D. R. et al., Ensyn Technologies Inc., "Thermo-Catalytic Cracking of Wood to Transportation Fuels," DSS Contract No. 38SQ.23440-4-1429, Efficiency and Alternative Energy Technology Branch, Natural Resources Canada, Ottawa, Canada (1997).
Huffman, D. R., Ensyn Technologies Inc., "Thermo-catalytic cracking of wood to transportation fuels using the RTP process," DSS Contract No. 38SQ.23440-4-1429, Efficiency and Alternative Energy Technology Branch, Natural Resources Canada, Ottawa, Ontario (Jan. 1997).
Hughes, J. et al. "Structural variations in natural F, OH and Cl apatites," *American Mineralogist*, 74 (1989) 870-876.
Huie, C. W. "A review of modern sample-preparation techniques for the extraction and analysis of medicinal plants," *Anal Bioanal Chem*, 373 (2002) 23-30.
International Search Report dated Feb. 22, 2013 for corresponding International Application No. PCT/US2012/68876.
Ioannidou, "Investigating the potential for energy, fuel, materials and chemicals production from corn residues (cobs and stalks) by non-catalytic and catalytic pyrolysis in two reactor configurations," *Renewable and Sustainable Energy Reviews*, 13 (2009) 750-762.

(56) References Cited

OTHER PUBLICATIONS

Iojoiu, E. et al. "Hydrogen production by sequential cracking of biomass-derived pyrolysis oil over noble metal catalysts supported on ceria-zirconia," *Applied Catalysis A: General*, 323 (2007) 147-161.
Jackson, M. et al. "Screening heterogenous catalysts for the pyrolysis of lignin," *J. Anal. Appl. Pyrolysis*, 85 (2009) 226-230.
Junming et al. "Bio-oil upgrading by means of ethyl ester production in reactive distillation to remove water and to improve storage and fuel characteristics," *Biomass and Energy*, 32 (2008) 1056-1061.
Kalnes, Tom et al. "Feedstock Diversity in the Refining Industry," UOP Report to NREL and DOE (2004).
Khanal, "Biohydrogen Production in Continuous-Flow Reactor Using Mixed Microbial Culture," *Water Environment Research*, 78:2 (2006) 110-117.
Khimicheskaya Entsiklopediya. Pod red. N. S. Zefirov. Moskva, Nauchnoe Izdatelstvo "Bolshaya Rossyskaya Entsiklopediya", 1995, p. 133-137,529-530.
Kingston et al. "New Taxanes from *Taxus brevifolia*," *J of Natural Products*, 45 (1982) 466-470.
Lappas, A. A. et al. "Biomass pyrolysis in a circulating fluid bed reactor for the production of fuels and chemicals," *Fuel*, 81 (2002) 2087-2095.
Lappas, A.A. et al. "Production of Transportation Fuels from Biomass," *Workshop of Chemical Process Engineering Research Institute/Center for Research and Technology Hellas*, Thermi-Thessaloniki, Greece (2004).
Lappas, A.A., "Production of biofuels via co-processing in conventional refining process," *Catalysis Today*, 145 (2009) 55-62.
Maiti, R.N. et al. "Gas-liquid distributors for trickle-bed reactors: A review"; *Industrial and Engineering Chemistry Research*, 46:19 (2007) 6164-6182.
Mancosky, "The use of a controlled cavitation reactor for bio-diesel production," (abstract only), AIChE Spring National Meeting 2007, Houston, Texas.
Marker, Terry L., et al. "Opportunities for Biorenewables in Petroleum Refineries," Proceedings of the 230th ACS National Meeting, Washington, DC, Paper No. 125, Fuel Division (Aug 31, 2005) (abstract only).
Marker, Terry L., et al., UOP, "Opportunities for Biorenewables in Oil Refineries," Final Technical Report, U.S. Department of Energy Award No. DE-FG36-05G015085, Report No. DOEGO15085Final (2005).
Marquevich, "Hydrogen from Biomass: Steam Reforming of Model Compounds of Fast-Pyrolysis Oil," *Energy & Fuels*, 13 (1999) 1160-1166.
Masoumifard, N. et al. "Investigation of heat transfer between a horizontal tube and gas-solid fluidized bed," *International Journal of Heat and Fluid Flow*, 29:5 (2008) 1504-1511.
McLaughlin et al. 19-Hydroxybaccatin III, 10-Deacetylcephalo-Mannine, and 10-Deacetyltaxol: New Anti-Tumor Taxanes from *Taxus wallichiana*, *J of Natural Products*, 44 (1981) 312-319.
McNeil "Semisynthetic Taxol Goes on Market Amid Ongoing Quest for New Versions," *J of the National Cancer Institute*, 87:15 (1995) 1106-1108.
Meier, D. et al. "State of the art of applied fast pyrolysis of lignocellulosic materials—a review," *Bioresource Technology*, 68:1 (1999) 71-77.
Meier, D. et al., "Pyrolysis and Hydroplysis of Biomass and Lignins—Activities at the Institute of Wood Chemistry in Hamburg, Germany," vol. 40, No. 2, Preprints of Papers Presented at the 209th ACS National Meeting, Anaheim, CA (Apr. 2-7, 1995).
Mercader, F. et al. "Pyrolysis oil upgrading by high pressure thermal treatment," *Fuel*, 89:10 (2010) 2829-2837.
Miller et al. "Antileukemic Alkaloids from *Taxus wallichiana* Zucc," *J Org Chem*, 46 (1981) 1469-1474.
Mohan, D. et al. "Pyrolysis of Wood/Biomass for Bio-oil: A Critical Review," *Energy Fuels*, 20:3 (2006) 848-849.

Newton "Taxol: A Case Study in Natural Products Chemistry," Lecture Notes, University of Southern Maine, http:/www.usm.maine.edu/ (2009) 1-6.
Nicolaou et al. "Total Synthesis of Taxol," *Nature*, 367 (1994) 630-634.
Nowakowski, D. et al. "Potassium catalysis in the pyrolysis behaviour of short rotation willow coppice," *Fuels*, 86 (2007) 2389-2402.
Ognisty, T. P. "The direct contact heat transfer performance of a spray nozzle, a notched through distributor, and two inch Pall rings," AIChE 1990 Spring National Meeting (Orlando 3/18-22-90) Preprint N. 37c 36P, Mar. 18, 1990.
Ohman "Bed Agglomeration Characteristics during Fluidized Bed Combustion of Biomass Fuels," *Energy & Fuels*, 14 (2000) 169-178.
Okumura, Y. et al. "Pyrolysis and gasification experiments of biomass under elevated pressure condition," Nihon Kikai Gakkai Ronbunshu, B Hen/Transactions of the Japan Society of Mechanical Engineers, Part B, vol. 73, No. 7, 2007, pp. 1434-1441.
Olazar, M. et al. "Pyrolysis of Sawdust in a Conical Spouted-Bed Reactor with a HZSM-5 Catalyst," *AIChE Journal*, 46:5 (2000) 1025-1033.
Onay "Influence of pyrolysis temperature and heating rate on the production of bio-oil and char from safflower seed by pyrolysis, using a well-swept fixed-bed reactor," *Fuel Processing Technology*, 88 (2007) 523-531.
Onay, "Production of Bio-Oil from Biomass: Slow Pyrolysis of Rapeseed (*Brassica napus* L.) in a Fixed-Bed Reactor," *Energy Sources*, 25 (2003) 879-892.
Ong et al. "Pressurized hot water extraction of bioactive or marker compounds in botanicals and medicinal plant materials," *J Chromatography A*, 1112 (2006) 92-102.
Ooi, Y. S. et al, "Catalytic Cracking of Used Palm Oil and Palm Oil Fatty Acids Mixture for the Production of Liquid Fuel: Kinetic Modeling." *J Am Chem Soc*, 18 (2004) 1555-1561.
Otterstedt, J. E. et al. "Catalytic Cracking of Heavy Oils," in Occelli, Mario L. (ed) Fluid Catalytic Cracking, Chapter 17, ACS, Washington, DC (1988) 266-278.
Padmaja, K.V. et al. "Upgrading of Candelilla biocrude to hydrocarbon fuels by fluid catalytic cracking," *Biomass and Bioenergy*, 33 (2009) 1664-1669.
Pavia et al., Intro to Org Labo Techniques (1988) 3d ed. Saunders College Publishing, Washington p. 62-66, 541-587.
PCT/US2012/055384 International Search Report, dated Mar. 28, 2013, and International Preliminary Report on Patentability, dated Mar. 25, 2014.
Pecora, A.A.B. et al., "Heat transfer coefficient in a shallow fluidized bed heat exchanger with a continuous ftow of solid particles," *Journal of the Brazilian Society of Mechanical Sciences and Engineering*, 28:3 (2006) 253-258.
Pecora, A.A.B., et al., "An analysis of process heat recovery in a gas-solid shallow fluidized bed," *Brazilian Journal of Chemical Engineering*, 23:4 (2006) 497-506.
Petrik, P.T. et at "Heat exchange in condensation of R227 coolant on inclined tubes placed in a granular BED," *Journal of Engineering Physics and Thermophysics*, 77:4 (2004) 758-761.
Prasad Y. S. et at "Catalytic conversion of canola oil to fuels and chemical feedstocks. Part II. Effect of co-feeding steam on the performance of HZSM-5 catalyst," *Can J Chem Eng*, 64 (1986) 285-292.
Prins, Wolter et al. "Progress in fast pyrolysis technology," *Topsoe Catalysis Forum 2010*, Munkerupgaard, Denmark (Aug. 19-20, 2010).
Radlein, D. et at "Hydrocarbons from the Catalytic Pyrolysis of Biomass," *Energy & Fuels*, 5 (1991) 760763.
Rao "Taxol and Related Taxanes. I. Taxanes of *Taxus brevifolia* Bark," *Pharm Res* 10:4 (1993) 521-524.
Rao et al. "A New Large-Scale Process for Taxol and Related Taxanes from *Taxus brevifolia*," *Pharm Res*, 12:7 (1995) 1003-1010.
Ravindranath, G., et al., "Heat transfer studies of bare tube bundles in gas-solid fluidized bed", 9th International Symposium on Fluid Control Measurement and Visualization 2007, FLUCOME 2007, vol. 3, 2007, pp. 1361-1369.

(56) References Cited

OTHER PUBLICATIONS

Rodriguez, O.M.H. et al. "Heat recovery from hot solid particles in a shallow fluidized bed," *Applied Thermal Engineering*, 22:2 (2002) 145-160.
Samolada, M. C. et al. "Production of a bio-gasoline by upgrading biomass flash pyrolysis liquids via hydrogen processing and catalytic cracking," *Fuel*, 77:14 (1998) 1667-1674.
Sang "Biofuel Production from Catalytic Cracking of Palm Oil," *Energy Sources*, 25 (2003) 859-869.
Scahill, J. et al. " Removal of Residual Char Fines from Pyrolysis Vapors by Hot Gas Filtration," in Bridgwater, A. V. et al. (eds) *Developments in Thermochemical Biomass Conversion*, Springer Science+Business Media, Dordrecht (1997) 253-266.
Scott, D. et al. Pretreatment of poplar wood for fast pyrolysis: rate of cation removal, *Journal of Analytical and Applied Pyrolysis*, 57 (2000) 169-176.
Senilh et al. "Mise en Evidence de Nouveaux Analogues du Taxol Extraits de *Taxus baccata*,"*J of Natural Products*, 47 (1984) 131-137. (English Abstract included).
Sharma, R. "Upgrading of pyrolytic lignin fraction of fast pyrolysis oil to hydrocarbon fuels over HZSM-5 in a dual reactor system," *Fuel Processing Technology*, 35 (1993) 201-218.
Sharma, R. K. et al. "Catalytic Upgrading of Pyrolysis Oil," *Energy & Fuels*, 7 (1993) 306-314.
Sharma, R. K. et al. "Upgrading of wood-derived bio-oil over HZSM-5," *Bioresource Technology*, 35:1 (1991) 57-66.
Smith R.M. "Extractions with superheated water," *J Chromatography A*, 975 (2002) 31-46.
Snader "Detection and Isolation," in Suffness, M. (ed) *Taxol-Science and Applications*, CRC Press, Boca Raton, Florida (1995) 277-286.
Srinivas, S.T. et al "Thermal and Catalytic Upgrading of a Biomass-Derived Oil in a Dual Reaction System," *Can. J. Chem. Eng.*, 78 (2009) 343-354.
Stierle et al. "The Search for Taxol-Producing Microorganism Among the Endophytic Fungi of the Pacific Yew, *Taxus brevifolia*," *J of Natural Products*, 58 (1995) 1315-1324.
Stojanovic, B. et al. "Experimental investigation of thermal conductivity coefficient and heat exchange between fluidized bed and inclined exchange surface," *Brazilian Journal of Chemical Engineering*, 26:2 (2009) 343-352.
Sukhbaatar, B. "Separation of Organic Acids and Lignin Fraction From Bio-Oil and Use of Lignin Fraction in Phenol-Formaldehyde Wood Adhesive Resin," *Master's Thesis*, Mississippi State (2008).
Twaiq, A. A. et al. "Performance of composite catalysts in palm oil cracking for the production of liquid fuels and chemicals," *Fuel Processing Technology*, 85 (2004) 1283-1300.
Twaiq, F. A. et al. "Liquid hydrocarbon fuels from palm oil by catalytic cracking over aluminosilicate mesoporous catalysts with various Si/Al ratios," *Microporous and Mesoporous Materials*, 64 (2003) 95-107.
Tyson, K. et al. "Biomass Oil Analysis: Research Needs and Recommendations," National Renewable Energy Laboratory, Report No. NREL/TP-510-34796 (Jun. 2004).
Valle, B. et al. "Integration of Thermal Treatment and Catalytic Transformation for Upgrading Biomass Pyrolysis Oil," *International Journal of Chemical Reactor Engineering*, 5:1 (2007).
Vasanova, L.K. "Characteristic features of heat transfer of tube bundles in a cross water-air flow and a three-phase fluidized bed," *Heat Transfer Research*, 34:5-6 (2003) 414-420.
Vitolo, S. et al. "Catalytic upgrading of pyrolytic oils over HZSM-5 zeolite: behaviour of the catalyst when used in repeated upgrading—regenerating cycles," *Fuel*, 80 (2001) 17-26.
Vitolo, S. et al. "Catalytic upgrading of pyrolytic oils to fuel over different zeolites," *Fuel*, 78:10 (1999) 1147-1159.
Wang, Xianhua et al., "The Influence of Microwave Drying on Biomass Pyrolysis," *Energy & Fuels* 22 (2008) 67-74.
Westerhof, Roel J. M. et al., "Controlling the Water Content of Biomass Fast Pyrolysis Oil," *Ind. Eng. Chem. Res.* 46 (2007) 9238-9247.
Williams, Paul T. et al. "Characterisation of oils from the fluidised bed pyrolysis of biomass with zeolite catalyst upgrading," *Biomass and Bioenergy*, 7:1-6 (1994) 223-236.
Williams, Paul T. et al. "Comparison of products from the pyrolysis and catalytic pyrolysis of rice husks," *Energy*, 25:6 (2000) 493-513.
Williams, Paul T. et al. "The influence of catalyst type on the composition of upgraded biomass pyrolysis oils," *J Analytical and Applied Pyrolysis*, 31 (1995) 39-61.
Yukimune et al. "Methyl Jasmonate-induced Overproduction of Paclitaxel and Baccatin III in Taxus Cell Suspension Cultures," *Nature Biotechnology* 14 (1996) 1129-1132.
Zhang et al. "Investigation on initial stage of rapid pyrolysis at high pressure using Taiheiyo coal in dense phase," *Fuel*, 81:9 (2002) 1189-1197.
Zhang, "Hydrodynamics of a Novel Biomass Autothermal Fast Pyrolysis Reactor: Flow Pattern and Pressure Drop," *Chem. Eng. Technol.*, 32:1 (2009) 27-37.
Graham, R.G. et al. "Thermal and Catalytic Fast Pyrolysis of Lignin by Rapid Thermal Processing (RPT)," Seventh Canadian Bioenergy R&D Seminar, Skyline Hotel, Ottawa, Ontario, Canada, Apr. 24-26, 1989.
Wisner, R. "Renewable Identification Numbers (RINs) and Government Biofuels Blending Mandates," *AgMRC Renewable Energy Newsletter* (Apr. 2009), available at http://www.agmrc.org/renewable_energy/biofuelsbiorefining_general/renewable-identification-numbers-rins-and-government-biofuels-blending-mandates/.
Qi et al. "Review of biomass pyrolysis oil properties and upgrading research," *Energy Conversion & Management*, 48 (2007) 87-92.
Office Action, U.S. Appl. No. 14/346,517, dated Sep. 25, 2015, available at www.uspto.gov.
Yoo et al. "Thermo-mechanical extrusion pretreatment for conversion of soybean hulls to fermentable sugars," *Bioresource Technology*, 102 (2011) 7583-7590.
Fogassy, G. et al., "Biomass derived feedstock co-processing with vacuum gas oil for second-generation fuel production in FCC units," *Applied Catalysis B: Environmental*, 96:3-4 (2010) 476-485.
Gutierrez et al., "Co-Processing of Upgraded Bio-Liquids in Standard Refinery Units-Fundamentals," 15th European Biomass Conference & Exhibition, Berlin, May 7-11 (2007).
Mercader, "Pyrolysis Oil Upgrading for Co-Processing in Standard Refinery Units," Ph.D. Thesis, University of Twente (2010).
Samolada, M.C. et al., "Catalyst Evaluation for Catalytic Biomass Pyrolysis," *Energy & Fuels*, 14:6 (2000) 1161-1167.
Zhang, Q. et al. "Review of biomass pyrolysis oil properties and upgrading research," *Energy Conversion & Management*, 48 (2007) 87-92.
Bridgwater et al., "Fast pyrolysis processes for biomass," *Renewable and Sustainable Energy Reviews*, 4:1 (2000) 1-73.
Scott, D. S., "Fast Pyrolysis of Biomass for Recovery of Specialty Chemicals," *Developments in Thermochemical Biomass Conversion*, Springer Netherlands (1997) 523-535.
Nikolakakis, A., "Taxus Canadensis Abundant Taxane: Conversion to Paclitaxel and Rearrangements," *Bioorganic & Medicinal Chem* 8.6 (2000) 1269-1280.
Hussain, ST et al., "Solubility of Oxalic Acid," *Asian J Res Chem* 5:11 (Nov. 2012) 1323-1330.
Chen, J. et al, "Experimental Study on Co-hydroprocessing Canola Oil and Heavy Vacuum Gas Oil Blends", *Energy Fuels* 27 (2013) 3306-3315.
Al-Sabawi, M., "Fluid Catalytic Cracking of Biomass-Derived Oils and Their Blends with Petroleum Feedstocks: A Review," *Energy Fuels* 26 (2012) 5355-5372.
Jenkins et al., "Combustion properties of biomass," *Fuel Proc. Tech.*, 54 (1998) 17-46.
Butler, E., "A Review of Recent Laboratory Research and Commercial Developments in Fast Pyrolysis and Upgrading," *Renewable and Sustainable Energy Reviews*, 15 (Sep. 16, 2011) 4171-4186.
Official Action dated Sep. 18, 2018 in U.S. Appl. No. 14/314,785.
Official Action dated Dec. 26, 2018 in U.S. Appl. No. 15/498,063.

(56) References Cited

OTHER PUBLICATIONS

Official Action dated Jul. 17, 2018 in Japanese Patent Application No. 2017-218578.

* cited by examiner

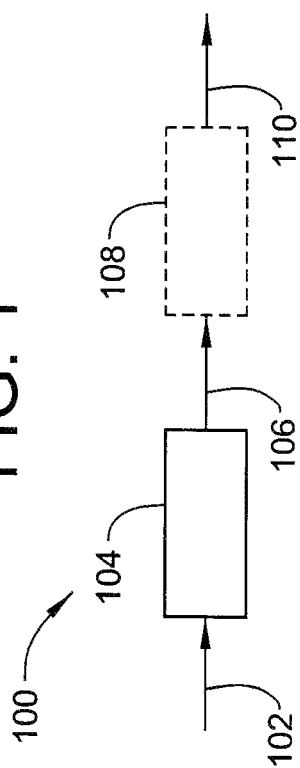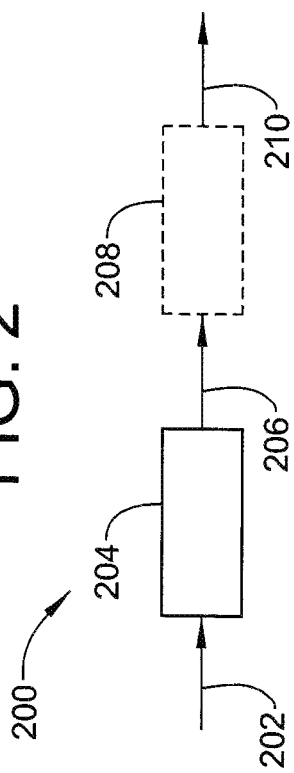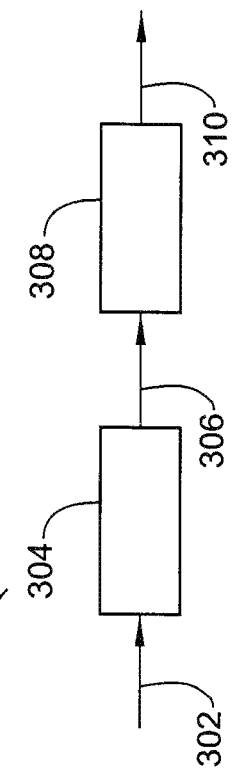

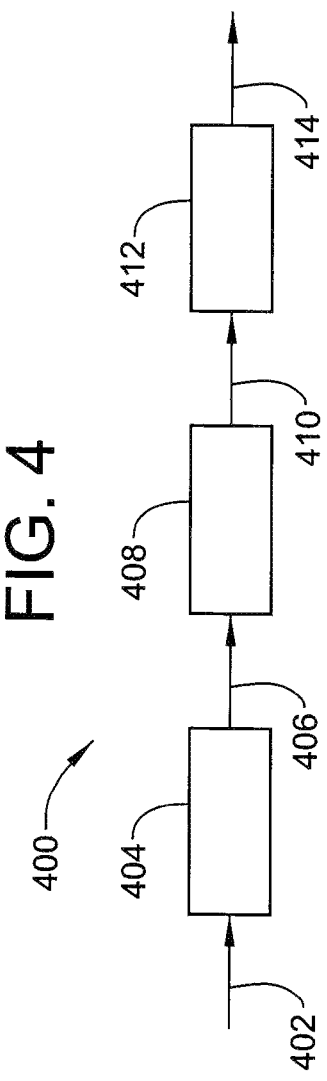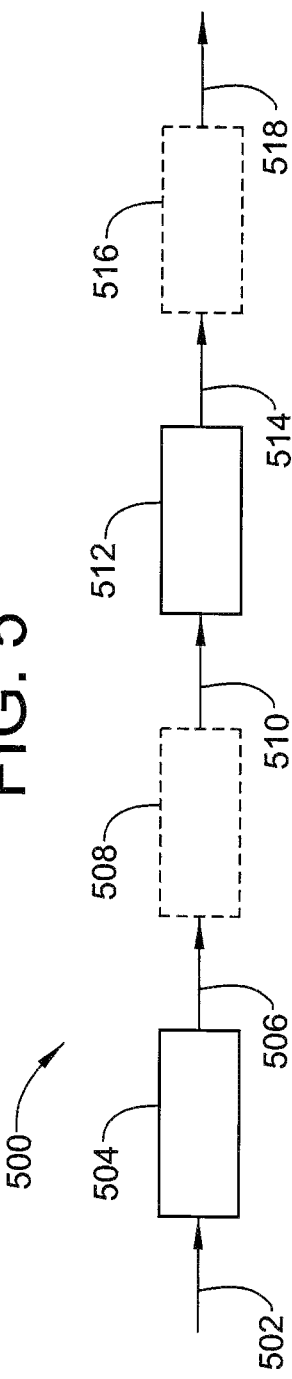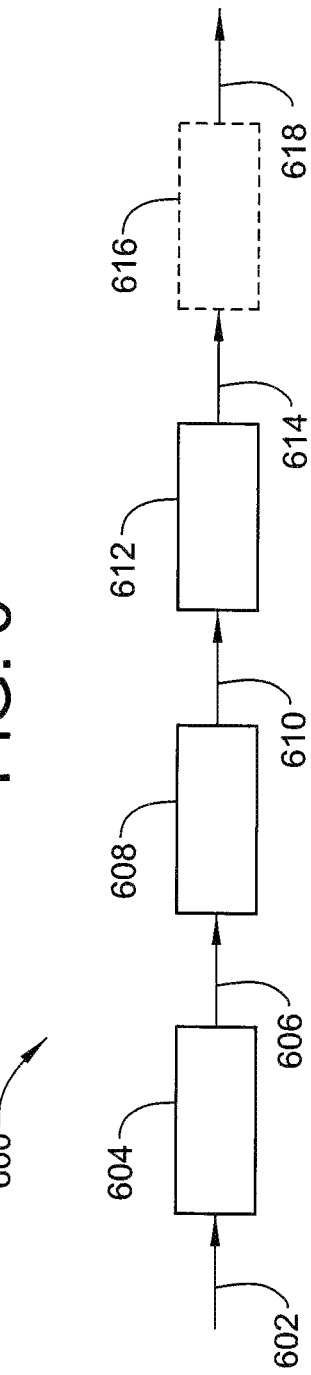

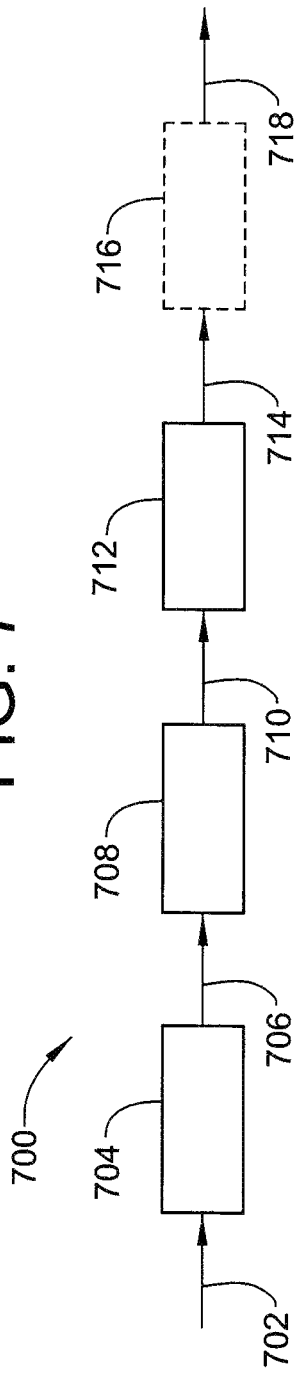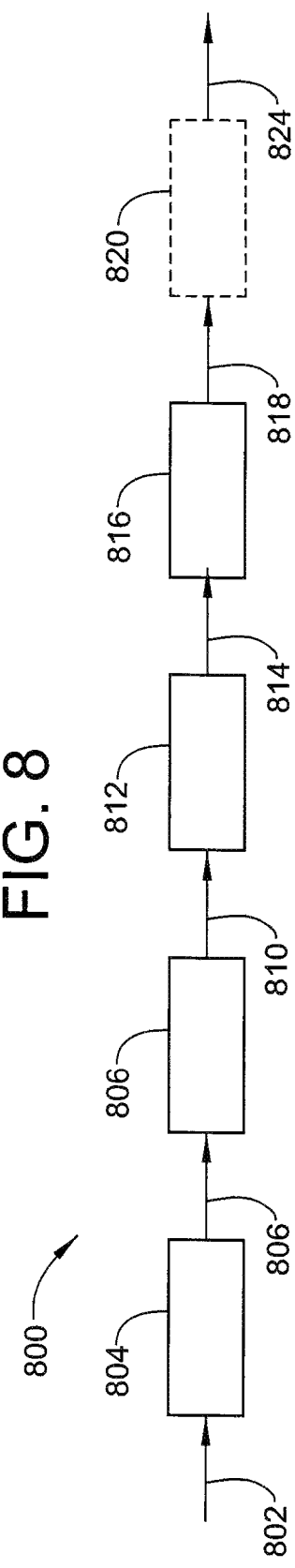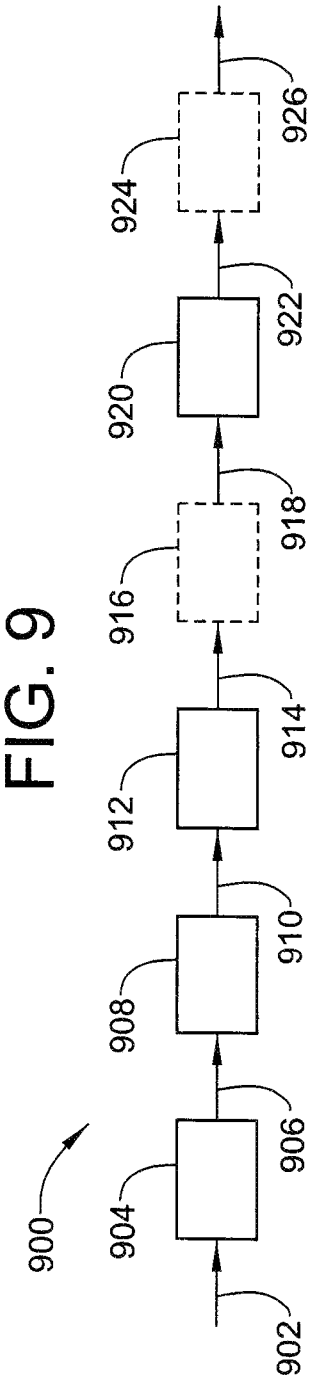

DEMETALLIZATION OF LIQUID BIOMASS

CROSS REFERENCE TO RELATED APPLICATIONS

This application is a continuation of U.S. patent application Ser. No. 15/851,080, filed Dec. 21, 2017, now U.S. Pat. No. 10,400,176, granted Sep. 3, 2019, which further claims the benefit of priority from U.S. Provisional Application No. 62/440,252, filed Dec. 29, 2016. The foregoing related applications, in their entirety, are incorporated herein by reference.

FIELD OF THE INVENTION

The present invention relates generally to methods, processes, systems, and/or apparatus for producing liquid biomass with a reduced concentration of contaminants, for example methods for producing low-metal and/or low-chlorine pyrolysis-derived liquid biomass.

BACKGROUND OF THE INVENTION

Following decades of renewable energy research, liquids derived from conversion of biomass (for example by rapid thermal processing, slow pyrolysis (for example a vacuum pyrolysis), catalytic pyrolysis, torrefaction, or hydrothermal processing, to name a few) are beginning to be used as petroleum substitutes in combustion and in refinery processes such as fluidized catalytic cracking.

One of the remaining challenges is to find cost-effective ways to remove contaminants from liquid biomass that may otherwise increase environmental emissions and/or complicate further processing. For example, rapid thermal processing of cellulosic biomass (for example wood, agricultural waste, etc.) may result in carryover of solids including char, ash, dissolved metals, and dissolved chlorine into the liquid biomass product. These contaminants can produce regulated emissions upon combustion, interfere with or poison catalysts used in refineries, and degrade process equipment (for example chlorine may result in stress cracking in metal equipment unless special alloys are used). These contaminants may also degrade the liquid biomass, thereby reducing shelf life and making it less useful. Char, for example, contributes to thermal instability, increases in viscosity, phase separation, and/or solids formation during storage.

Accordingly, methods, processes, systems, and apparatus are needed to produce liquid biomass having a relatively low contaminant concentration.

BRIEF SUMMARY OF THE INVENTION

Certain embodiments may provide, for example, a method, process, system, and/or apparatus to remove at least a portion of a contaminant (for example ash, metal ions, or chlorine ions) present in a liquid biomass (for example a product of rapid thermal processing of a cellulosic biomass). In certain embodiments, for example, the method may comprise complexing at least a portion of the contaminant with a complexing agent (for example a dissolved complexing agent or a solid state complexing agent) to form a complex (for example a solid complex). In certain further embodiments, the method may comprise separating (for example by filtering and/or by separating with a cyclone separator) at least a portion of the complex from the liquid biomass. In certain embodiments, for example, the liquid biomass may be a recently condensed liquid biomass (for example a liquid product of a rapidly quenched pyrolysis stream). In certain embodiments, for example, the liquid biomass may be a collected liquid product from a pyrolysis system (for example a liquid product obtained by combining the condensate from a primary condenser, a secondary condenser, a demister, and/or a filter bed of a rapid thermal processing system). In certain embodiments, for example, the method may be integral to rapid thermal processing. In certain embodiments, for example, the method may reduce the time for undesirable reactions in a liquid biomass to occur, such as polymerization reactions and/or reactions catalyzed by the presence of solids such as char, ash, dissolved metals, and/or dissolved chlorine present in the liquid biomass.

Certain embodiments may provide, for example, a method to remove at least a portion of a contaminant present in a liquid biomass, comprising: complexing at least a portion of the contaminant with a dissolved complexing agent (for example a metal chelating agent, such as less than 0.2 wt. % oxalic acid, relative to the quantity of the liquid biomass) to form a solid complex (for example a precipitate), and separating the solid complex from the liquid biomass. In certain further embodiments, for example, the liquid biomass may have a pH of greater than 2, including, for example, before and after separating the solid complex from the liquid biomass. In certain embodiments, for example, the separating may comprise filtration. In certain embodiments, for example, the temperature of the liquid biomass may be increased to reduce viscosity to improve filtration (for example by increasing the temperature of the liquid biomass resulting in a less viscous or a thinner liquid, thereby reducing the upstream pressure required to filter, increasing flow through the filter at a given upstream pressure, and/or reducing the frequency and/or time that the filter is offline for cleaning or other maintenance) and/or to promote efficient cyclone separation of the solid complex from the liquid biomass. In certain embodiments, the filtration may have no appreciable effect on the pH of the liquid biomass.

Certain embodiments may provide, for example, a method to reduce a plurality of contaminants present in a liquid biomass (for example reducing a total alkali and/or alkaline earth metals concentration by at least 25% to less than 1000 ppm by weight in the liquid biomass, and reducing a total chlorine concentration by at least 25% to less than 1000 ppm by weight in the liquid biomass), comprising: complexing at least a portion of the plurality of contaminants with a plurality of dissolved complexing agents to form a plurality of solid complexes, and separating at least a fraction of the plurality of solid complexes from the liquid biomass. In certain embodiments, for example, a first of the plurality of complexing agents may be selective to a first of the plurality of contaminants relative to a second of said plurality of contaminants.

Certain embodiments may provide, for example, a method to remove at least a portion of one or more contaminants (for example chlorine ions) present in a liquid biomass, comprising: complexing at least a portion of the one or more contaminants with an anionic ion exchange complexing agent to form one or more complexes. In certain embodiments, for example, the one or more complexes may comprise one or more contaminants bound (for example electrostatically bound (for example by Van der Waals forces), weakly bound, covalently bound, and/or ionically bound) to the anionic ion exchange complexing agent. In certain embodiments, for example, the method may further comprise separating at least a portion of the one or more complexes from the liquid biomass (for example by filtration). In certain embodiments, for example, the method may further comprise removing at least a portion of the liquid biomass from the presence of the one or more complexes (for example by removing the liquid biomass from a fixed bed of the anionic ion exchange complexing agent).

Certain embodiments may provide, for example, a method to reduce a plurality of contaminants present in a liquid biomass, comprising: complexing at least portion of a first contaminant (for example a metal ion) with a dissolved first complexing agent (for example a metal chelating agent, for example less than 0.2 wt. % oxalic acid relative to the weight of the liquid biomass) to form a first complex (for example a precipitate), followed by further complexing at least a portion of a second contaminant with a second complexing agent (for example a cationic ion exchange resin). In certain embodiments, for example, the second contaminant may not form a solid complex with the first complexing agent. In certain embodiments, for example, the complexing and the further complexing may occur simultaneously, for example by adding a mixture of the first complexing agent and the second complexing agent to the liquid biomass. In certain embodiments, for example the complexing and the further complexing may occur sequentially. In certain embodiments, for example the complexing and the further complexing may occur simultaneously and sequentially by, for example, adding a second complexing agent with the first complexing agent and a further complexing agent subsequently thereto. In certain further embodiments, for example, the first complex may be at least partially separated (for example by filtration) from the liquid biomass prior to the further complexing.

Certain embodiments may provide, for example, a method to obtain a reduced-contaminant liquid biomass stream from a pyrolysis stream (for example a gaseous pyrolysis stream produced by rapid thermal processing of cellulosic biomass) having one or more contaminants (for example metal contaminants present in ash, char, and/or inorganic heat transfer particles in the pyrolysis stream), comprising: condensing a portion of the pyrolysis stream in the presence of one or more contaminant complexing agents to form a liquid biomass condensate comprising one or more contaminant complexes; and separating at least a fraction of the one or more contaminant complexes from the condensate to form the reduced-contaminant liquid biomass stream. In certain embodiments, for example, the condensing may occur in a single stage rapid quench condenser (for example at a temperature greater than 20° C., such as a temperature in the range of 30-70° C.). In certain embodiments, for example, the temperature of the condenser may be selected to not only condense a portion of the pyrolysis stream but also to promote ready filtering of the liquid biomass condensate. In certain embodiments, for example, the reduced-contaminant liquid biomass stream may have a pH of at least 2.

Certain embodiments may provide, for example, a method of preparing a reduced-metal liquid biomass, comprising: forming a first quantity of metal complex-containing condensate in a condenser, filtering a portion of the first quantity of metal complex-containing condensate to form the reduced-metal liquid biomass, cooling a further portion of said first quantity of metal complex-containing condensate to form a quantity of quench, and contacting at least a portion of the quantity of quench with a quantity of pyrolysis vapor (for example a quantity of condensable pyrolysis vapor present in a pyrolysis stream) and a quantity of metal chelating agent to form a second quantity of metal complex-containing condensate. In certain embodiments, for example, the quantity of quench may be at least 50 times greater (for example at least 100 times greater, at least 200 times greater, at least 300 times greater, or the quantity of quench may be at least 1000 times greater), on a weight basis, than the second quantity of metal-complex containing condensate.

Certain embodiments may provide, for example, a method, comprising: contacting at least a portion of a contaminant-containing pyrolysis stream with a contaminant complexing agent in a first condenser to form a reduced-contaminant overhead stream and a contaminant complex-containing first bottom stream, condensing a portion of the reduced-contaminant overhead stream in a second condenser to form a further overhead stream and a second bottom stream, and removing at least a portion of the contaminant complex from at least a portion of the first bottom stream. In certain further embodiments, for example, the method may further comprise combining at least portions of the first bottom stream and the second bottom stream. In certain embodiments, for example, the average liquid residence time of the first condenser may be at least 5 minutes, at least 30 minutes, at least 60 minutes, at least 2 hours, at least 2.5 hours, at least 3 hours, or the average liquid residence time of the first condenser may be at least 4 hours. In certain embodiments, for example, the method may further comprise: passing at least a portion of the further overhead stream through a demister. In certain embodiments, for example, the method may further comprise passing at least a portion of the further overhead stream through one or more filter beds (for example, passing at least a portion of the further overhead stream through one or more filter beds before or after passing through a demister).

Certain embodiments may provide, for example, a method, comprising: passing at least a portion of a pyrolysis stream through a multi-condenser separation train to form at least a first liquid biomass stream and a second liquid biomass stream, reducing the concentration of one or more contaminants present in the first liquid biomass stream by contacting at least a portion of the first liquid biomass stream with one or more decontamination agents, combining at least portions of the first liquid biomass stream and the second liquid biomass stream to form a product stream, wherein each of the first liquid biomass stream and the product stream has a pH of at least 2, and adjusting the temperature of a first condenser of the multi-condenser separation train to control the concentration of the one or more contaminants in the product stream. In certain embodiments, for example, the ratio of the first liquid biomass stream relative to the second liquid biomass stream, on a weight basis, may be at least 0.05:1, for example at least 0.1:1, at least 0.3:1, at least 0.5:1, at least 1:1, at least 1.5:1, at least 2:1, at least 2.5:1, at least 3:1, at least 4:1, at least 5:1, at least 7:1, at least 10:1, or the ratio of the first liquid biomass stream relative to the second liquid biomass stream may be at least 20:1 on a weight basis. In certain embodiments, for example, the second liquid biomass stream may have a pH of at least 2. In certain embodiments, for example, the method may further comprise filtering a least a portion of the product stream to remove at least a portion of a suspended solid component. In certain embodiments, for example, the method may further comprise filtering the product stream to remove a portion of at least one of the one or more decontamination agents.

Certain embodiments may provide, for example, a method to obtain a low-contaminant liquid biomass stream from a contaminant-containing pyrolysis stream, comprising: contacting at least a portion of the pyrolysis stream with a quench stream and a contaminant complexing agent in a condenser to form solid complex-containing condensate, and filtering at least a portion of the solid complex from the condensate. In certain embodiments, for example, the average liquid residence time of the condenser may be at least 5 minutes, at least 30 minutes, at least 60 minutes, or the average liquid residence time of the condenser may be at least 2 hours. In certain embodiments, for example, the contaminant complexing agent may be dissolved into the condensate. In certain embodiments, for example, at least a portion of the pyrolysis stream may be quenched to a temperature of less than 70° C. in less than 1 second. In certain embodiments, for example, the filtering may comprise passing at least a portion of the condensate through a cake of ground biomass. In certain embodiments, for example, at least a portion of the cake of ground biomass may be positioned relative to a filter or loaded in a filter assembly. In certain further embodiments, at least a portion of the cake of ground biomass may be periodically removed (for example removed from a filter) and combusted to generate process heat (for example, the heat may be used to dry a biomass prior to thermal processing such as rapid thermal processing).

Certain embodiments may provide, for example, a method to obtain a low-contaminant liquid biomass stream from a contaminant-containing pyrolysis stream, comprising: contacting at least a portion of the pyrolysis stream with a quench stream and a contaminant complexing agent in a collection column to form solid complex-containing condensate, recirculating at least a portion of the condensate through an external cooling loop, and pumping at least a portion of the condensate through an external separator assembly configured to collect at least a portion of the solid complex. In certain embodiments, for example, the quench stream comprises at least a portion of a return stream from the cooling loop. In certain further embodiments, for example, at least a portion of the quench stream may be unfiltered. In certain embodiments, for example, the external separator assembly may be separate from the external cooling loop. In certain embodiments, for example, at least a portion of the quench stream may be filtered. In certain embodiments, for example, the external separator assembly may be in-line with the external cooling loop.

Certain embodiments may provide, for example, an apparatus, comprising: a pyrolysis upflow reactor, at least a single stage condenser system in fluid communication with a pyrolysis stream outlet of the reactor, and at least one filter assembly in fluid communication with a bottom outlet of the condenser system. In certain embodiments, for example, the condenser system may comprise a condensing vessel having a pyrolysis stream inlet, a complexing agent inlet (for example an inlet configured to introduce one or more solid state complexing agents to the condensing vessel, or an inlet configured to introduce one or more complexing agents present in a carrier to the condensing vessel, such as an inlet configured to introduce one or more complexing agents pre-mixed with a liquid biomass to the condensing vessel), a bottom outlet, an overhead outlet, and an inlet to a quench distributor, the quench distributor positioned in an upper portion of the vessel. In certain embodiments, for example, the condenser system may comprise a cooling recirculation loop forming a fluid flow path from the bottom outlet to the quench distributor, the cooling recirculation loop comprising a pump and a heat exchanger. In certain embodiments, for example, the apparatus may further comprise a high performance cyclone positioned in-line between the pyrolysis stream outlet of the reactor and the pyrolysis stream inlet of the condenser. In certain embodiments, for example, the apparatus may further comprise a hot vapor filter positioned in-line between the pyrolysis stream outlet of the reactor and the pyrolysis stream inlet of the condenser. In certain embodiments, for example, the apparatus may further comprise at least a second single stage condenser in fluid communication with the first single stage condenser. In certain embodiments, for example, the apparatus may further comprise at least a demister. In certain embodiments, for example, the apparatus may further comprise further filter assemblies in fluid communication with the first filter assembly.

Certain embodiments may provide, for example, a method to obtain a low-contaminant liquid biomass stream from a solids-containing pyrolysis stream, comprising: condensing a portion of the solids-containing pyrolysis stream (for example a stream containing pyrolysis vapors and entrained solid particles) to form a condensate containing suspended solids, dissolving contaminants (for example, metals and/or their counterions) present in the suspended solids into the condensate, and contacting the condensate with a contaminant complexing agent to form solid complex-containing condensate. In certain embodiments, for example, at least one agent may be added to the condensate to promote the dissolving. In certain embodiments, at least one agent may be added to the condensate to inhibit the dissolving. In certain embodiments, for example, the solids may comprise one or more of ash, char, heat transfer medium, catalyst particles, catalytically active particles, and fines.

Certain embodiments may provide, for example, an apparatus or a method to remove at least a portion of one or more contaminants present in a pyrolysis stream, comprising: condensing a portion of the pyrolysis stream in the presence of one or more complexing agents (for example one or more complexing agents, and/or one or more complexing agents present in a carrier (such as one or more complexing agents mixed with, mixed into, or pre-mixed with a liquid biomass)) to form a slurry, the slurry comprising a liquid biomass and the one or more solid complexing agents, and removing a portion of the one or more complexing agents from the slurry to form a substantially complexing agent-free liquid biomass stream. In certain embodiments, for example, a portion of the one or more sold-state complexing agents may be bound to at least one of the one or more contaminants (for example forming a contaminant complex precipitate). In certain embodiments, for example, the pyrolysis stream may be rapidly condensed with a quench stream. In certain further embodiments, the quench stream may be formed from the slurry. In certain embodiments, for example, the slurry may have an average residence time in a primary condenser assembly of at least 5 minutes, at least 30 minutes, at least 60 minutes, or an average residence time of at least 2 hours in the primary condenser assembly. In certain further embodiments, for example, the primary condenser assembly may comprise at least one slurry pump.

Certain embodiments may provide, for example, a method to remove at least a portion of a contaminant present in a liquid biomass, comprising: complexing at least a portion of the contaminant with a complexing agent to form a complex; and separating the complex from the liquid biomass.

Certain embodiments may provide, for example, a method to remove at least a portion of a contaminant present in a liquid biomass, comprising: complexing at least a portion of the contaminant with a dissolved complexing agent to form a solid complex; and separating the solid complex from the liquid biomass.

Certain embodiments may provide, for example, a method to reduce a plurality of contaminants present in a liquid biomass, comprising: complexing at least a portion of the plurality of contaminants with a plurality of dissolved complexing agents to form a plurality of solid complexes; and separating at least a portion of the plurality of solid complexes from the liquid biomass.

Certain embodiments may provide, for example, a method to remove at least a portion of one or more contaminants present in a liquid biomass, comprising: complexing at least a portion of the one or more contaminants with an anionic ion exchange complexing agent to form one or more complexes; and separating the one or more complexes from the liquid biomass.

Certain embodiments may provide, for example, a method to reduce a plurality of contaminants present in a liquid biomass, comprising: complexing at least a portion of a first contaminant with a dissolved first complexing agent to form a first complex; followed by further complexing at least a portion of a second contaminant with one or more second complexing agents (for example one or more solid-state complexing agents, or one or more complexing agents present in a carrier (such as one or more complexing agents mixed with, mixed into, or pre-mixed with a liquid biomass)).

Certain embodiments may provide, for example, a method to obtain a low-contaminant liquid biomass stream from a pyrolysis stream having one or more contaminants, comprising: condensing a portion of the pyrolysis stream in the presence of one or more contaminant complexing agents to form a liquid biomass condensate comprising one or more contaminant complexes; and separating at least a portion of at least one of the one or more contaminant complexes from the condensate to form the low-contaminant liquid biomass stream.

Certain embodiments may provide, for example, a method of preparing a reduced-metal liquid biomass, comprising: forming a first quantity of metal complex-containing condensate in a condenser; filtering a portion of the first quantity of metal complex-containing condensate to form the reduced-metal liquid biomass; cooling a further portion of said first quantity of metal complex-containing condensate to form a quantity of quench; and contacting at least a portion of the quantity of quench with a quantity of pyrolysis vapor and a quantity of metal chelating agent to form a second quantity of metal complex-containing condensate.

Certain embodiments may provide, for example, a method, comprising: in a first condenser, contacting at least a portion of a contaminant-containing pyrolysis stream with a contaminant complexing agent to form a reduced-contaminant overhead stream and a contaminant complex-containing bottom stream; in a second condenser, condensing a portion of the reduced-contaminant overhead stream to form a further overhead stream and a second bottom stream; removing at least a portion of the contaminant complex from the first bottom stream; and optionally, combining at least portions of the first bottom stream and the second bottom stream.

Certain embodiments may provide, for example, a method, comprising: passing at least a portion of a pyrolysis stream through a multi-condenser separation train to form at least a first liquid biomass stream and a second liquid biomass stream; reducing the concentration of one or more contaminants present in the first liquid biomass stream by contacting the first liquid biomass stream with one or more decontamination agents; combining at least portions of the first liquid biomass stream and the second liquid biomass stream to form a product stream, wherein each of the first liquid biomass stream and the product stream has a pH of at least 2; and adjusting the temperature of a first condenser of the multi-condenser separation train to control the concentration of the one or more contaminants in the product stream.

Certain embodiments may provide, for example, a method to obtain a low-contaminant liquid biomass stream from a contaminant-containing pyrolysis stream, comprising: contacting at least a portion of the pyrolysis stream with a quench stream and a contaminant complexing agent in a condenser to form solid complex-containing condensate; and filtering to separate at least a portion of the solid complex from at least a portion of the condensate.

Certain embodiments may provide, for example, a method to obtain a low-contaminant liquid biomass stream from a contaminant-containing pyrolysis stream, comprising: contacting at least a portion of the pyrolysis stream with a quench stream and a contaminant complexing agent in a collection column to form solid complex-containing condensate; recirculating at least a portion of the condensate through an external cooling loop; and pumping at least a portion of the condensate through an external separator assembly configured to collect at least a portion of the solid complex.

Certain embodiments may provide, for example, a method to obtain a low-contaminant liquid biomass stream from a solids-containing pyrolysis stream, comprising: condensing a portion of the solids-containing pyrolysis stream to form a condensate containing suspended solids; dissolving at least a portion of contaminants present in the suspended solids into the condensate; and contacting at least a portion of the condensate with a contaminant complexing agent to form solid complex-containing condensate.

Certain embodiments may provide, for example, a method to remove one or more contaminants present in a pyrolysis stream, comprising: condensing a portion of the pyrolysis stream in the presence of one or more complexing agents (for example one or more solid-state complexing agents, or one or more complexing agents present in a carrier (such as one or more complexing agents mixed with, mixed into, or pre-mixed with a liquid biomass)) to form a slurry, the slurry comprising: a) a liquid biomass; and b) the one or more complexing agents optionally bound to at least one of the one or more contaminants; and removing a portion of the one or more complexing agents from the slurry to form a substantially complexing agent-free liquid biomass stream.

Certain embodiments may provide, for example, a method, comprising: providing: a) a condensing vessel having a bottom outlet and a quench distributor, the quench distributor positioned in an upper portion of the vessel, b) a cooling recirculation loop forming a fluid flow path from the bottom outlet to the quench distributor, the cooling recirculation loop comprising a pump and a heat exchanger, and c) condensed pyrolysis vapors at a temperature of at least 30° C. and a pH of at least 2, the condensed pyrolysis vapors (or the liquid) having a total average residence time of at least 5 minutes, at least 30 minutes, at least 60 minutes, or a total average residence time of at least 2 hours in the condensing vessel and in the cooling recirculation loop combined, the condensed pyrolysis vapors comprising a downward flowing quench stream exiting the quench distributor; introducing at least a portion of a pyrolysis stream and at least a portion of a metal chelating agent stream into the condensing vessel; condensing at least a portion of the pyrolysis stream in the condensing vessel to form a solid complex-containing portion of the condensed pyrolysis vapors; filtering a fraction of the condensed pyrolysis vapors in a first filter assembly, the first filter assembly configured to collect at least a portion of the solid complex; mixing at least a portion of the filtered fraction of the condensed pyrolysis vapors with cationic ion exchange particles and anionic ion exchange particles in a temperature-controlled mixing vessel to form a mixture; and passing at least a portion of the mixture through a second filter assembly to form a liquid biomass product having a pH of at least 2, a total metal concentration of less than 1000 ppm, for example less than 500 ppm, less than 250 ppm, less than 200 ppm, less than 100 ppm, or a total metal concentration of less than 50 ppm, and a total chlorine concentration of less than 1000 ppm, for example less than 500 ppm, less than 250 ppm, less than 200 ppm, less than 100 ppm, less than 60 ppm or a total chlorine concentration of less than 50 ppm, the second filter assembly configured to collect at least a portion of the cationic ion exchange particles and at least a portion of the anionic ion exchange particles. In certain embodiments, for example, the quench distributor may be an atomizing spray nozzle. In certain further embodiments, for example, at least a portion of the quench stream may be at least partially atomized. In certain further embodiments, for example, the first filter assembly may comprise at least two filters. In certain embodiments, for example, the at least two filters may be cycled. In certain embodiments, for example, the first filter assembly may comprise a cake of ground biomass. In certain embodiments, for example, the pyrolysis stream may be filtered with a hot vapor filter prior to introduction to the primary condenser. In certain embodiments, for example, at least a portion of the first pyrolysis stream may be passed through a high efficiency cyclone prior to introduction to the primary condenser. In certain embodiments, for example, at least a portion of the first pyrolysis stream may be derived from rapid thermal pyrolysis of a cellulosic biomass, for example a water-washed cellulosic biomass.

Certain embodiments may provide, for example, a process for reducing metal and chlorine contaminants in a first pyrolysis stream, comprising: providing a primary condenser operating at a temperature of at least 30° C. and an average liquid residence time of at least 5 minutes, at least 30 minutes, at least 60 minutes, or an average liquid residence time of at least 2 hours; introducing at least a portion of the first pyrolysis stream and a metal chelating agent stream into the primary condenser to form a solid complex-containing first liquid biomass stream having a pH of at least 2 and a reduced-contaminant second pyrolysis stream, at least a portion of the metal chelating agent stream introduced at a ratio of less than 0.2 wt. % metal chelate relative to at least a portion of the first liquid biomass stream; condensing in a second collection column a portion of the second pyrolysis stream to form a second liquid biomass stream having a pH of at least 2 and a third pyrolysis stream; passing at least a portion of the third pyrolysis stream through a demister and optionally one or more filter beds to obtain a combustible gas and one or more additional liquid biomass streams, each of the one or more additional liquid biomass streams having a pH of at least 2; pumping at least a portion of the solid complex-containing first liquid biomass stream through an external filter assembly configured to collect at least a portion of the solid complex; followed by combining at least portions of the first, the second, and the one or more additional liquid biomass streams to form a product stream; contacting at least a portion of the product stream with cationic ion exchange particles and anionic exchange particles; followed by filtering at least a portion of the product stream to form a filtered product stream having: a) a pH of at least 2; and b) total alkali and alkaline earth metal concentration of less than 1000 ppm, for example less than 500 ppm, less than 250 ppm, less than 200 ppm, less than 100 ppm, or a total alkali and alkaline earth metal concentration of less than 50 ppm. In certain further embodiments, for example the filtered product stream may have a total chlorine concentration of less than 1000 ppm, for example less than 500 ppm, less than 250 ppm, less than 200 ppm, less than 100 ppm, less than 60 ppm or a total chlorine concentration of less than 50 ppm. In certain embodiments, for example, at least a portion of the pyrolysis stream may be filtered with a hot vapor filter prior to condensing. In certain embodiments, for example, at least a portion of the pyrolysis stream may be passed through a high efficiency cyclone prior to introduction to condensing. In certain embodiments, for example, at least a portion of the pyrolysis stream may be derived from rapid thermal pyrolysis of a cellulosic biomass, for example a water-washed cellulosic biomass.

Certain embodiments may provide, for example, an apparatus, comprising: a pyrolysis upflow reactor; at least a single stage condenser system in fluid communication with a pyrolysis stream outlet of the reactor, comprising: a) a condensing vessel having a pyrolysis stream inlet, a complexing agent inlet (for example an inlet configured to introduce one or more solid state complexing agents to the condensing vessel, and/or an inlet configured to introduce one or more complexing agents present in a carrier to the condensing vessel, such as an inlet configured to introduce one or more complexing agents pre-mixed with a liquid biomass to the condensing vessel), a bottom outlet, an overhead outlet, and a quench distributor, the quench distributor positioned in an upper portion of the vessel; and b) a cooling recirculation loop forming a fluid flow path from the bottom outlet to the quench distributor, the cooling recirculation loop comprising a pump and a heat exchanger; and a filter assembly in fluid communication with the bottom outlet.

DETAILED DESCRIPTION OF THE DRAWINGS

FIG. 1 is a schematic depiction of a process comprising cationic ion exchange to remove metal contaminants from a liquid biomass.

FIG. 2 is a schematic depiction of a process comprising anionic ion exchange for removing contaminants from a liquid biomass.

FIG. 3 is a schematic depiction of a process comprising use of a chelating agent for removing metal contaminants from a liquid biomass.

FIG. 4 is a schematic depiction of a process comprising use of a chelating agent, cationic ion exchange, and anionic ion exchange for removing contaminants from a liquid biomass.

FIG. 5 is a schematic depiction of a process comprising cationic ion exchange and anionic ion exchange for removing contaminants from a liquid biomass.

FIG. 6 is a schematic depiction of a process comprising use of a chelating agent and anionic ion exchange for removing contaminants from a liquid biomass.

FIG. 7 is a schematic depiction of a process comprising use of a chelating agent and cationic ion exchange for removing contaminants from a liquid biomass.

FIG. 8 is a schematic depiction of a process comprising use of a chelating agent, cationic ion exchange, intermediate filtration, and anionic ion exchange for removing contaminants from a liquid biomass.

FIG. 9 is a schematic depiction of a process comprising use of a chelating agent, cationic ion exchange, multiple intermediate filtration, and anionic ion exchange for removing contaminants from a liquid biomass.

DETAILED DESCRIPTION OF THE INVENTION

Figure 10:
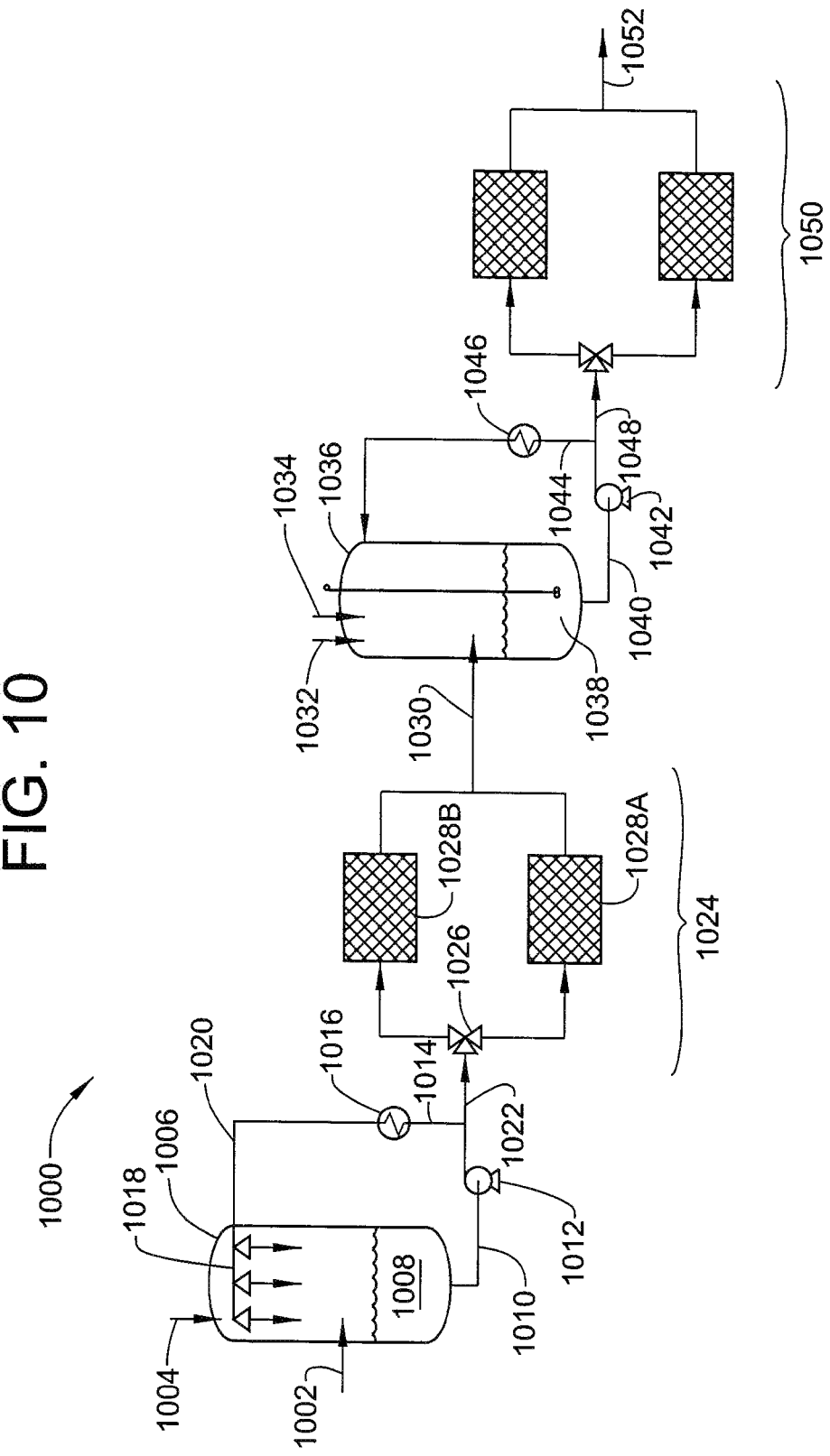
FIG. 10 is a schematic depiction of a process incorporating a quench condenser for removing contaminants from a pyrolysis stream.

In certain embodiments, one of the foregoing embodiments may further comprise one or more than one of the following further embodiments, inclusive of further embodiments that may comprise one or more of the other further embodiments or parts thereof. In certain embodiments, one or more than one (including for instance all) of the following further embodiments may comprise the other embodiments or parts thereof.

Certain embodiments may provide, for example, methods, processes, systems, or apparatus to reduce, remove, and/or recover one or more contaminants present in a liquid biomass.

In certain embodiments, for example, the one or more contaminants may comprise one or more solids. In certain embodiments, for example, the one or more solids may be suspended in the liquid biomass. In certain embodiments, for example, the one or more solids may comprise residue of a biomass material used to make the liquid biomass. In certain embodiments, the one or more contaminants may comprise a dissolved portion of the one or more solids (for example the suspended solids). In certain further embodiments, for example, the one or more solids may comprise ash, for example ash comprising one or more metals (for example alkali and/or alkaline earth metals). In certain embodiments, for example, the one or more solids may comprise char. In certain embodiments, for example, the one or more solids may comprise catalyst particles. In certain further embodiments, for example, the catalyst particles may comprise zeolites. In certain embodiments, for example, the one or more solids may comprise inert particles. In certain further embodiments, for example, the inert particles may comprise sand.

In certain embodiments, for example, the one or more solids may be present in the liquid biomass (prior to any treatment to remove, reduce, or recover the one or more solids from the liquid biomass) at a concentration, relative to the weight of the liquid biomass, of at least 0.01 wt. %, for example at a concentration of at least 0.05 wt. %, at least 0.1 wt. %, at least 0.25 wt. %, at least 0.5 wt. %, at least 0.75 wt. %, at least 1 wt. %, at least 2.5 wt. %, or at a concentration of at least 5 wt. %. In certain embodiments, for example, the one or more solids may be present in the liquid biomass at a concentration, relative to the weight of the liquid biomass, in the range of 0.01-5 wt. %, for example at a concentration in the range of 0.05-2 wt. %, in the range of 0.1-1 wt. %, in the range of 0.1-0.5 wt. %, in the range of 0.1-0.25 wt. %, in the range of 0.5-1.0 wt. %, or at a concentration in the range of 0.5-0.75 wt. %.

In certain embodiments, for example, the ash may be present in the liquid biomass (prior to any treatment to remove, reduce, or recover the ash from the liquid biomass) at a concentration, relative to the weight of the liquid biomass, of at least 0.01 wt. %, for example at a concentration of at least 0.05 wt. %, at least 0.1 wt. %, at least 0.25 wt. %, at least 0.5 wt. %, at least 0.75 wt. %, at least 1 wt. %, at least 2.5 wt. %, or at a concentration of at least 5 wt. %. In certain embodiments, for example, the ash may be present in the liquid biomass at a concentration, relative to the weight of the liquid biomass, in the range of 0.01-5 wt. %, for example at a concentration in the range of 0.05-2 wt. %, in the range of 0.1-1 wt. %, in the range of 0.1-0.5 wt. %, in the range of 0.1-0.25 wt. %, in the range of 0.5-1.0 wt. %, or at a concentration in the range of 0.5-0.75 wt. %.

In certain embodiments, for example, the one or more solids, exclusive of ash, may be present in the liquid biomass (prior to any treatment to remove, reduce, or recover the one or more solids from the liquid biomass) at a concentration, relative to the weight of the liquid biomass, of at least 0.005 wt. %, for example at a concentration of at least 0.025 wt. %, at least 0.05 wt. %, at least 0.125 wt. %, at least 0.25 wt. %, at least 0.375 wt. %, at least 0.5 wt. %, at least 1.25 wt. % or at a concentration of at least 2.5 wt. %. In certain embodiments, for example, the one or more solids, exclusive of ash, may be present in the liquid biomass at a concentration, relative to the weight of the liquid biomass, in the range of 0.005-2.5 wt. %, for example at a concentration in the range of 0.025-1 wt. %, in the range of 0.05-0.5 wt. %, in the range of 0.05-0.25 wt. %, in the range of 0.05-0.125 wt. %, in the range of 0.25-0.5 wt. %, or at a concentration in the range of 0.25-0.375 wt. %.

In certain embodiments, for example, the one or more contaminants may comprise one or more metals, inclusive but not limited to metals in ionic form, non-ionic form, solid-state form, soluble form, dissolved form, and/or insoluble form. In certain embodiments, for example, the one or more metals may be dissolved in the liquid biomass. In certain embodiments, for example, the one or more metals may be present in ash in the liquid biomass. In certain embodiments, for example, the one or more metals may be present in char in the liquid biomass. In certain embodiments, for example, the one or more metals may be present in a combination of two or more of the liquid biomass, the ash, and the char (for example, a portion of the one or more metals may be dissolved as ions while a further portion of the one or more metals may be present in the ash). In certain embodiments, for example, the one or more metals may comprise one or more alkali metals (for example sodium, potassium, and/or cesium), alkaline earth metals (for example magnesium, calcium, barium, and/or strontium), transition metals (for example iron, nickel, and/or manganese), and/or other metals.

In certain embodiments, for example, the total concentration of the one or more metals in the liquid biomass (prior to any treatment to remove, reduce, or recover the one or more metals from the liquid biomass), inclusive of metal in one or more solids present in the liquid biomass, may be in the range of 25-5000 ppm, for example the total concentration of the one or more metals in the liquid biomass may be in the range of 25-500 ppm, 50-500 ppm, 100-500 ppm, 200-500 ppm, 300-400 ppm, 500-5000 ppm, 500-4000 ppm, 500-3000 ppm, 500-2000 ppm, 500-1000 ppm, 1000-4000 ppm, 1000-3000 ppm, 2000-3000 ppm, or the total concentration of the one or more metals in the liquid biomass may be in the range of 2250-2750 ppm.

In certain embodiments, for example, the total concentration of aluminum, antimony, arsenic, barium, beryllium, boron, cadmium, calcium, chromium, cobalt, copper, iron, lead, lithium, magnesium, manganese, mercury, molybdenum, nickel, phosphorous, potassium, sodium, selenium, silicon, silver, strontium, tin, titanium, vanadium, and zinc in the liquid biomass (prior to any treatment to remove, reduce, or recover said metals from the liquid biomass), inclusive of amounts of said metals in one or more solids present in the liquid biomass, may be in the range of 25-5000 ppm, for example the total concentration of said metals in the liquid biomass may be in the range of 25-500 ppm, 50-500 ppm, 100-500 ppm, 200-500 ppm, 300-400 ppm, 500-5000 ppm, 500-4000 ppm, 500-3000 ppm, 500-2000 ppm, 500-1000 ppm, 1000-4000 ppm, 1000-3000 ppm, 2000-3000 ppm, or the total concentration of said metals in the liquid biomass may be in the range of 2250-2750 ppm.

In certain embodiments, for example, the concentration of calcium in the liquid biomass (prior to any treatment to remove, reduce, or recover the calcium from the liquid biomass), inclusive of calcium in one or more solids present in the liquid biomass, may be in the range of 25-2500 ppm, for example the total concentration of calcium in the liquid biomass may be in the range of 25-250 ppm, 50-250 ppm, 100-250 ppm, 150-250 ppm, 150-200 ppm, 500-2500 ppm, 500-2000 ppm, 500-1750 ppm, 750-1750 ppm, 750-1500 ppm, 1000-2000 ppm, 1250-2000 ppm, 1000-1500 ppm, or the total concentration of calcium in the liquid biomass may be in the range of 1250-1750 ppm.

In certain embodiments, for example, the concentration of magnesium in the liquid biomass (prior to any treatment to remove, reduce, or recover the magnesium from the liquid biomass), inclusive of magnesium in one or more solids present in the liquid biomass, may be in the range of 15-1000 ppm, for example the total concentration of magnesium in the liquid biomass may be in the range of 25-500 ppm, 25-200 ppm, 25-100 ppm, 25-50 ppm, 50-100 ppm, 50-75 ppm, 100-1000 ppm, 150-750 ppm, 150-500 ppm, 150-250 ppm, 175-250 ppm, 175-225 ppm, or the total concentration of magnesium in the liquid biomass may be in the range of 100-200 ppm.

In certain embodiments, for example, the concentration of Potassium in the liquid biomass (prior to any treatment to remove, reduce, or recover the potassium from the liquid biomass), inclusive of Potassium in one or more solids present in the liquid biomass, may be in the range of 10-300 ppm, for example the total concentration of potassium in the liquid biomass may be in the range of 10-200 ppm, 10-100 ppm, 20-50 ppm, 50-250 ppm, 50-200 ppm, 75-200 ppm, 75-200 ppm, 100-200 ppm, 125-175 ppm, 100-150 ppm, or the total concentration of potassium in the liquid biomass may be in the range of 125-150 ppm.

In certain embodiments, for example, the concentration of sodium in the liquid biomass (prior to any treatment to remove, reduce, or recover the sodium from the liquid biomass), inclusive of sodium in one or more solids present in the liquid biomass, may be in the range of 10-300 ppm, for example the total concentration of sodium in the liquid biomass may be in the range of 10-200 ppm, 10-100 ppm, 20-50 ppm, 50-250 ppm, 50-200 ppm, 75-200 ppm, 75-200 ppm, 100-200 ppm, 125-175 ppm, 100-150 ppm, or the total concentration of sodium in the liquid biomass may be in the range of 125-150 ppm.

In certain embodiments, the one or more contaminants may comprise a halogen, for example bromine, chlorine, iodine, and/or ions of the same. In certain further embodiments, for example, the halogen, for example the chlorine and/or the chlorine ion, may be present in the liquid biomass at a concentration of at least 50 ppm, for example at a concentration of at least 75 ppm, at least 100 ppm, at least 200 ppm, at least 300 ppm, at least 400 ppm, at least 500 ppm, at least 600 ppm, at least 700 ppm, at least 800 ppm, at least 900 ppm, for example at a concentration of at least 1000 ppm. In certain further embodiments, for example, the halogen may be present in the liquid biomass at a concentration in the range of 25-1000 ppm, for example at a concentration in the range of 50-800 ppm, in the range of 50-700 ppm, in the range of 50-500 ppm, in the range of 50-400 ppm, in the range of 50-300 ppm, in the range of 50-200 ppm, in the range of 50-150 ppm, in the range of 75-125 ppm, for example at a concentration in the range of 75-100 ppm.

In certain embodiments, for example, the one or more contaminants may comprise a plurality of contaminants. In certain further embodiments, for example, the plurality of contaminants may comprise a combination of one or more of the foregoing metal, halogen, and solid contaminants. In certain further embodiments, for example, the plurality of contaminants may comprise a combination of one or more of the foregoing metal, halogen, and solid contaminants at the ranges specified in the foregoing paragraphs.

In certain embodiments, for example, the liquid biomass may be derived from a biomass source. Suitable sources of biomass include (but are not limited to), for example, wood, hardwood, softwood, wood residues, sawdust, slash bark, thinnings, forest cullings, begasse, corn fiber, corn stover, empty fruit bunches (EFB), fronds, palm fronds, flax, straw, low-ash straw, energy crops, palm oil, non-food-based biomass materials, crop residue, slash, pre-commercial thinnings and tree residue, annual covercrops, switchgrass, miscanthus, extractive rich biomass, cellulosic-containing components, cellulosic components of separated yard waste, cellulosic components of separated food waste, cellulosic components of separated municipal solid waste (MSW), or combinations thereof. In certain embodiments, for example, the biomass source may qualify as a Renewable Fuel Standard (RFS2) biomass, and/or may be used to make a liquid biomass that qualifies as a renewable fuel under the Renewable Fuel Standard (RFS2). Cellulosic biomass, for example, includes biomass derived from or containing cellulosic materials. In certain embodiments, for example, at least a portion of the one or more contaminants present in the liquid biomass may be carried over or derived from one or more components of the biomass source (for example metals present in the biomass source and/or chlorine present in the biomass source). In certain embodiments, example, at least a portion of the one or more contaminants present in the liquid biomass may be carried over or derived from conversion of the biomass source to the liquid biomass (for example char and/or ash resulting from thermal or catalytic processing of the biomass source, and/or inorganic inert or catalytic particles). In certain embodiments, for example, at least a portion of the one or more contaminants present in the liquid biomass may be carried over or derived from process equipment or process reagents used to make the liquid biomass.

In certain embodiments, for example, the liquid biomass may qualify as a renewable fuel under the Renewable Fuel Standard (RFS2). In certain embodiments, for example, the liquid biomass may be eligible to generate Renewable Identification Number (RIN) credits. In certain embodiments, for example, the liquid biomass may be a refinery co-processing liquid biomass (for example co-processing with a petroleum feedstock in a catalytic cracker). In certain further embodiments, for example, the co-processed liquid biomass may be used to produce fuels (for example transportation fuels) that qualify for one or more parties obtaining Renewable Identification Number (RIN) credits. In certain embodiments, for example, the liquid biomass may qualify as a fuel meeting the requirements of the low carbon fuel standard. In certain embodiments, for example, the liquid biomass may be used (for example, further processed) to form one or more further chemicals, for example one or more foods, plastics, resins, pharmaceutical compounds, specialty chemicals, and or organic chemicals.

In certain embodiments, for example, the liquid biomass may be derived from a water-washed biomass source. In certain further embodiments, for example, the biomass source may be rinsed with water prior to conversion to the liquid biomass, for example rinsed prior to conversion by pyrolysis. In certain embodiments, for example, the biomass source may be rinsed with water to remove inorganic contaminants (for example pieces of metal, plastic, sand, etc.) present with the biomass source (for example by using the water rise to accomplish a physical separation). In certain embodiments, for example, the biomass source may be rinsed with water to reduce the chlorine content (for example soluble chlorine present in salts) of the biomass source, for example by up to 5%, up to 10%, up to 15%, up to 20%, up to 25%, up to 30%, up to 35%, up to 40%, up to 45%, up to 50%, up to 60%, or the biomass source may be rinsed with water to reduce the chlorine content of the biomass source by up to 70%. In certain embodiments, for example, a biomass source with at least 100 ppm chlorine may be water-washed to reduce the chlorine content to below 90 ppm. In certain embodiments, for example, a biomass source with at least 150 ppm chlorine may be water-washed to reduce the chlorine content to below 140 ppm. In certain embodiments, for example, a biomass source with at least 200 ppm chlorine may be water-washed to reduce the chlorine content to below 190 ppm. In certain embodiments, for example, a biomass source with at least 100 ppm chlorine may be water-washed to reduce the chlorine content by at least 10%. In certain embodiments, for example, a biomass source with at least 150 ppm chlorine may be water-washed to reduce the chlorine content by at least 10%. In certain embodiments, for example, a biomass source with at least 200 ppm chlorine may be water-washed to reduce the chlorine content by at least 10%. In certain embodiments, for example, a biomass source with at least 250 ppm chlorine may be water-washed to reduce the chlorine content by at least 10%. In certain embodiments, for example, a biomass source with at least 300 ppm chlorine may be water-washed to reduce the chlorine content by at least 10%. In certain embodiments, for example, a biomass source with at least 350 ppm chlorine may be water-washed to reduce the chlorine content by at least 10%. In certain embodiments, for example, a biomass source with at least 400 ppm chlorine may be water-washed to reduce the chlorine content by at least 10%. In certain embodiments, for example, a biomass source with at least 450 ppm chlorine may be water-washed to reduce the chlorine content by at least 10%.

In certain embodiments, for example, the liquid biomass may comprise a contaminant-containing product of rapid thermal processing. In certain embodiments, for example, the rapid thermal processing may comprise rapidly heating (for example to a temperature the range of 350-600° C.) a biomass (for example a cellulosic biomass) in the absence of oxygen, resulting in decomposition of one or more biomass components to generate pyrolysis vapors (a portion of which may be condensable to form a liquid product) and char. In certain further embodiments, for example, the pyrolysis vapors may be rapidly quenched to minimize secondary reactions, for example quenched in less than 5 seconds following the start of the rapid heating of the biomass, such as within 1 second following the start of rapid heating of the biomass.

In certain embodiments, for example, the rapid thermal processing may comprise feeding a biomass material (for example solid cellulosic biomass, for example a solid cellulosic biomass that has been water-washed) to an upflow reactor (such as an upflow reactor forming a component of a circulating fluidized bed) wherein the biomass material is mixed with an upward flowing stream of hot heat carriers (for example sand) in a substantially oxygen-free environment at a temperature in the range of 350-600° C. and a residence time of less than 5 seconds (for example at a temperature of approximately 500° C. and an average residence time of less than 2 seconds). In certain embodiments, for example, residence time of the upflow reactor, defined as the ratio of the reactor volume to the volumetric flow rate of material (inclusive of biomass, hot heat carriers, and fluidization gas) introduced to the reactor, may be less than 2 seconds, for example in the range of 0.05-2 seconds, in the range of 0.05-1 seconds, in the range of 0.05-0.5 seconds, in the range of 0.5-2 seconds, or for example a residence time in the range of 0.5-1 seconds. In certain embodiments, for example, the biomass may consist of solid biomass particles having an average size of less than 10 mm, less than 6 mm, less than 5 mm, for example less than 3 mm, less than 2 mm, or an average size of less than 1 mm. In certain embodiments, for example, the biomass may consist of solid biomass particles having an average particle size in the range of 0.5-3 mm, in the range of 0.5-1.5 mm, in the range of 0.5-1 mm, or an average particle size in the range of 2-3 mm. In certain further embodiments, for example, the biomass material may be converted into a pyrolysis stream (for example a hot vapor stream having a condensable portion) in the upflow reactor and the pyrolysis stream may contain at least a portion of the one or more contaminants (for example chlorine, metal-containing ash solids, dissolved metals, and other solids (for example residual char and heat carriers)). In certain further embodiments, for example, the hot vapor stream may be passed through a hot vapor filter to remove one or more of ash, residual char, inorganic particles, metals (and salts thereof), and aerosols. In certain embodiments, for example, the liquid biomass may comprise or be derived from a pyrolysis condensate or a fraction thereof. In certain further embodiments, for example, the pyrolysis stream may be cooled and condensed to form the contaminant-containing liquid biomass.

In certain embodiments, for example, the rapid thermal processing may occur in the absence of a catalyst. In certain embodiments, for example, the rapid thermal processing may occur in the presence of one or more catalysts (for example one or more of a metal catalyst, a zeolite catalyst, a metallocine catalyst, an acid catalyst, and/or a basic catalyst).

In certain embodiments, for example, the rapid thermal processing may be performed in a fluidized bed reactor containing a fluidized dense phase region in a lower portion of the reactor, the dense phase region comprising biomass (for example solid biomass particles), heat transfer particles (for example sand) and upward flowing fluidizing gas. In certain embodiments, for example, the fluidization gas may be introduced to the dense phase region proximate the bottom of the reactor. In certain embodiments, for example, the fluidized bed reactor may further comprise a dilute phase region above the dense phase region (for example, in an upper portion of the reactor such as a freeboard region of the reactor) which receives pyrolysis gases (inclusive of, for example, pyrolysis vapors such as condensable pyrolysis vapors) and char formed in the dense phase region. In certain embodiments, for example, the fluidization gas may be adjusted to achieve a pyrolysis gas residence time in the freeboard region of less than 2 seconds, for example in the range of 0.05-2 seconds, in the range of 0.05-1 seconds, in the range of 0.05-0.5 seconds, in the range of 0.5-2 seconds, or a pyrolysis gas residence time in the freeboard region of in the range of 0.5-1 seconds. In certain embodiments, for example, the biomass may consist of solid biomass particles having an average size of less than 10 mm, less than 6 mm, less than 5 mm, for example less than 3 mm, less than 2 mm, or an average size of less than 1 mm. In certain embodiments, for example, the biomass may consist of solid biomass particles having an average particle size in the range of 0.5-3 mm, in the range of 0.5-1.5 mm, in the range of 0.5-1 mm, or an average particle size in the range of 2-3 mm. In certain further embodiments, for example, pyrolysis gases (inclusive of, for example, pyrolysis vapors such as condensable pyrolysis vapors) formed in the fluidized bed reactor may contain at least a portion of the one or more contaminants (for example chlorine, metal-containing ash solids, dissolved metals, and other solids (for example residual char and heat carriers)). In certain further embodiments, for example, the pyrolysis gases may be passed through a hot vapor filter to remove one or more of ash, residual char, inorganic particles, metals (and salts thereof), and aerosols. In certain embodiments, for example, the liquid biomass may comprise a pyrolysis condensate or a fraction thereof. In certain further embodiments, for example, the pyrolysis vapors may be cooled and condensed to form the contaminant-containing liquid biomass.

In certain embodiments, for example, the rapid thermal processing may be performed in an ablative reactor wherein biomass particles may be accelerated to high velocities by a carrier gas and then introduced tangentially to a heated inner wall of the reactor. In certain further embodiments, for example, the biomass particle may thereby undergo pyrolysis resulting from heat transfer from the inner wall to form pyrolysis gases (inclusive of, for example, pyrolysis vapors such as condensable pyrolysis vapors). In certain further embodiments, for example, the heated inner wall of the reactor may be heated to a temperature in the range of at least 500° C., for example at least 600° C., for example at least 625° C., for example heated to a temperature in the range of 600-650° C. In certain embodiments, for example, the residence time of pyrolysis gases (inclusive of, for example, pyrolysis vapors such as condensable pyrolysis vapors) in the ablative reactor may be in the range of less than 1 second, for example less than 0.5 seconds, for example less than 0.1 seconds, or for example the residence time of vapors in the ablative reactor may be in the range of 0.05-0.1 seconds. In certain further embodiments, for example, pyrolysis gases formed in the ablative reactor may contain at least a portion of the one or more contaminants (for example chlorine, metal-containing ash solids, dissolved metals, and other solids (for example residual char and heat carriers)). In certain further embodiments, for example, the pyrolysis gases may be passed through a hot vapor filter to remove one or more of ash, residual char, inorganic particles, metals (and salts thereof), and aerosols. In certain embodiments, for example, the liquid biomass may comprise a pyrolysis condensate or a fraction thereof. In certain further embodiments, for example, pyrolysis vapors present in the pyrolysis gases may be cooled and condensed to form the contaminant-containing liquid biomass.

In certain embodiments, for example, the rapid thermal processing may comprise feeding a biomass material (for example solid cellulosic biomass, for example a solid cellulosic biomass that has been water-washed) to a rotating cone pyrolysis reactor wherein the biomass material is mixed with an hot heat carriers (for example sand) at the base of the rotating cone in a substantially oxygen-free environment at a temperature in the range of 350-600° C. and a residence time of less than 5 seconds (for example at a temperature of approximately 500° C. and an average residence time of less than 2 seconds). In certain further embodiments, for example, the heat transfer material and biomass material may be transported towards the lip of the spinning cone in the reactor by centrifugal force, and pyrolysis gases (inclusive of, for example, pyrolysis vapors such as condensable pyrolysis vapors) are collected. In certain embodiments, for example, vapor residence time of the rotating cone reactor may be 2 seconds, for example in the range of 0.05-2 seconds, for example 0.05-1 seconds, 0.05-0.5 seconds, 0.5-2 seconds, or for example a residence time of less than 0.5-1 seconds. In certain embodiments, for example, the biomass may consist of solid biomass particles having an average size of less than 10 mm, less than 6 mm, less than 5 mm, for example less than 3 mm, less than 2 mm, or an average size of less than 1 mm. In certain embodiments, for example, the biomass may consist of solid biomass particles having an average particle size in the range of 0.5-3 mm, in the range of 0.5-1.5 mm, in the range of 0.5-1 mm, or an average particle size in the range of 2-3 mm. In certain further embodiments, for example, the biomass material may be converted into a pyrolysis stream (for example a hot vapor stream) in the rotating cone reactor and contain at least a portion of one or more contaminants (for example chlorine, metal-containing ash solids, dissolved metals, and other solids (for example residual char and heat carriers)). In certain further embodiments, for example, the hot vapor stream may be passed through a hot vapor filter to remove one or more of ash, residual char, inorganic particles, metals (and salts thereof), and aerosols. In certain embodiments, for example, the liquid biomass may comprise a pyrolysis condensate or a fraction thereof. In certain further embodiments, for example, the pyrolysis stream may be cooled and condensed to form the contaminant-containing liquid biomass.

In certain embodiments, for example, the liquid biomass may comprise a contaminant-containing product of vacuum pyrolysis of solid biomass in a vacuum pyrolysis reactor (comprising a vacuum chamber) at a temperature in the range of 350-600° C., for example a temperature in the range of 500-600° C., for example a temperature in the range of 500-525° C. In certain embodiments, for example, the solid biomass may comprise solid biomass particles having an average size of less than 7 cm, for example less than 5 cm. In certain embodiments, for example, the solid biomass may comprise solid biomass particles having an average size in the range of 2-5 cm. In certain embodiments, solid biomass may comprise solid biomass particles having an average size of less than 2 cm, for example an average size of less than 1 cm. In certain embodiments, for example, the solid biomass particles may be heated in the vacuum chamber by molten salts. In certain further embodiments, for example, pyrolysis gases (inclusive of, for example, pyrolysis vapors such as condensable pyrolysis vapors) formed in the vacuum pyrolysis reactor may contain at least a portion of the one or more contaminants (for example chlorine, metal-containing ash solids, dissolved metals, and other solids (for example residual char and heat carriers)). In certain further embodiments, for example, the pyrolysis gases may be passed through a hot vapor filter to remove one or more of ash, residual char, inorganic particles, metals (and salts thereof), and aerosols. In certain embodiments, for example, the liquid biomass may comprise a pyrolysis condensate or a fraction thereof. In certain further embodiments, for example, the pyrolysis vapors present in the pyrolysis gases may be cooled and condensed to form the contaminant-containing liquid biomass. In certain further embodiments, for example, the vacuum pyrolysis may be a slow pyrolysis. In certain embodiments, for example, the residence time of the solid biomass particles in the vacuum chamber may be greater than 10 seconds, for example greater than 30 seconds, greater than 1 minute, greater than 3 minutes, greater than 5 minutes, or the residence time of the solid biomass particles in the vacuum chamber may be greater than 10 minutes. In certain embodiments, for example, the residence time of the solid biomass particles in the vacuum chamber may be in the range of 1-10 minutes, for example in the range of 5-10 minutes.

In certain embodiments, for example, the liquid biomass may comprise a product of torrefaction, or slow pyrolysis.

In certain embodiments, for example, the liquid biomass may comprise a product of hydrothermal processing in a reactor. In certain further embodiments, for example, the solid biomass particles may be introduced to heated compressed water to form the liquid biomass. In certain embodiments, for example, the water may be heated to a temperature of at least 150° C., for example at least 200° C., at least 250° C., the water may be heated to a temperature of at least at least 300° C. In certain embodiments, for example, the water may be heated to a temperature in the range of 300-350° C. In certain embodiments, for example, the heated water may be at a pressure of at least 70 bars, for example at least 100 bars, for example a pressure in the range of 100-180 bars. In certain embodiments, for example, the reactor may have a residence time of at least 0.05 seconds, for example at least 10 seconds, at least 5 minutes, the reactor may have a residence time of at least 10 minutes. In certain embodiments, for example, the reactor may have a residence time in the range of 0.05-10 seconds or in the range of 10-20 seconds. In certain further embodiments, for example, the hydrothermal processing may comprise use of a catalyst (for example to speed up the rate of liquid product formation). In certain further embodiments, for example, the catalyst may be a homogeneous catalyst. In certain embodiments, for example, the catalyst may be a heterogeneous (for example a solid) catalyst. In certain embodiments, for example, the catalyst may comprise an alkali metal or alkaline earth salt (for example NaOH, KOH, $Na_2CO_3$, and/or $K_2CO_3$). In certain embodiments, for example, the catalyst may comprise an acid, for example HCl, $H_2SO_4$, and/or $H_3PO_4$. In certain embodiments, for example, the liquid biomass may contain one or more contaminants, for example one or more metals, chlorine, residual catalyst, or inorganic particles.

In certain embodiments, for example, the liquid biomass may have a pH in the range of 0.5 to 8.0, for example, the liquid biomass may have a pH in the range of 0.5 to 7.0, such as 0.5 to 6.5, 1.0 to 6.0, 2.0 to 5.0, 3.0 to 7.0, 1.0 to 4.0, or 2.0 to 3.5. In certain embodiments, for example, the pH of the liquid biomass may be less than 8.0, for example less than 7.0, less than 6.5, less than 6.0, less than 5.5, less than 5.0, less than 4.5, less than 4.0, less than 3.5, less than 3.0, less than 2.5, or less than 2.0. In certain embodiments, for example, the pH of the liquid biomass may be altered or modified by the addition of an external, non-biomass derived material or pH altering agent. In certain embodiments, for example, the liquid biomass may be acidic. In certain embodiments, for example, the liquid biomass may have a pH in the range of between 0.5 to 7, such as between 0.5 to 3, between 1 to 7, between 1 to 6.5, between 2 to 5, between 2 to 3, between 2 to 3.5, between 1 to 4, between 2 to 6, or between 2 to 5. In certain embodiments, for example, the liquid biomass has a pH resulting from the conversion of the biomass from which it may be derived, such as a biomass-derived pH.

In certain embodiments, for example, the liquid biomass may comprise a water content in the range of between 10-40 wt. %. In certain embodiments, for example, the liquid biomass may comprise a water content in the range of between 15 and 35 wt. %, such as between 15 and 30 wt. %, between 20 and 35 wt. %, between 20 and 30 wt. %, between 30 and 35 wt. %, between 25 and 30 wt. %, between 20 and 25 wt. %, between 22 and 24 wt. %, or between 32 and 33 wt. % water. In certain embodiments, for example, the liquid biomass may comprise a water content in the range of less than 40 wt. %, such as less than 35 wt. %, or less than 30 wt. %. In certain embodiments, for example, the liquid biomass may comprise a water content of at least 10 wt. %, such as at least 15 wt. %, at least 20 wt. %, or at least 25 wt. %. In certain embodiments, for example, the liquid biomass may comprise a water content of 23 wt. %. In certain embodiments, for example, the liquid biomass may comprise a water content of less than 25 wt. %. In certain embodiments, for example, the water content of the liquid biomass may be in the range of 0.05 wt. % to 40 wt. %. In certain embodiments, for example, the water content of the liquid biomass may be in the range of 20 wt. % to 30 wt. %, 20 wt. % to 25 wt. %, 20 wt. % to 22 wt. %, 22 wt. % to 25 wt. %, or 25 wt. % to 30 wt. %. In certain embodiments, for example, the water content of the liquid biomass introduced into the combustion system may be in the range of 1 wt. % to 35 wt. %, such as 5 wt. % to 35 wt. %, 10 wt. % to 30 wt. %, 10 wt. % to 20 wt. %, 10 wt. % to 15 wt. %, 15 wt. % to 25 wt. %, 15 wt. % to 20 wt. %, 20 wt. % to 35 wt. %, 20 wt. % to 30 wt. %, 20 wt. % to 25 wt. %, 25 wt. % to 30 wt. %, or 30 wt. % to 35 wt. %. In certain embodiments, for example, the water content of the liquid biomass feedstock introduced into a combustion system may be at least 23 wt. % such as at least 25 wt. %, at least 28 wt. %, at least 30 wt. %, at least 31 wt. %, at least 32 wt. %, at least 33 wt. %, or at least 35 wt. %. In certain embodiments, for example, the water content of the liquid biomass feedstock introduced into the combustion system may be at least 1 wt. %, such as at least 10 wt. %, at least 15 wt. %, at least 20 wt. %, or at least 30 wt. %. In certain embodiments, for example, the water content of the liquid biomass may be less than 38 wt. %, such as less than 35 wt. %, less than 34 wt. %, less than 30 wt. %, less than 25 wt. %, less than 20 wt. %, or less than 15 wt. %.

In certain embodiments, for example, the liquid biomass may comprise an oxygen content level higher than that of a petroleum fraction feedstock or a fossil fuel (for example a heating fuel oil). In certain embodiments, for example, the liquid biomass may have an oxygen content level of greater than 20 wt. %, on a dry basis or moisture-free basis, such as an oxygen content level in the range of 20-50 wt. %, in the range of 35-40 wt. %, in the range of 25-35 wt. %, in the range of 20-30 wt. %, in the range of 25-50 wt. %, in the range of 20-40 wt. %, or in the range of 20-35 wt. %, on a dry basis or moisture-free basis. In certain embodiments, for example, the liquid biomass may have an oxygen content level of less than 20 wt. %, for example less than 15 wt. %, or an oxygen content level of less than 10 wt. %. In certain embodiments, for example, the liquid biomass may have an oxygen content level in the range of 5-20 wt. %, for example in the range of 5-15 wt. %, or an oxygen content level in the range of 10-20 wt. %.

In certain embodiments, for example, the liquid biomass may comprise a greater oxygen content level than carbon content level. In certain embodiments, for example, the liquid biomass may have a greater oxygen content level than carbon content level, on a moisture-containing basis. In certain embodiments, for example, the liquid biomass may have in the range of between 35-80 wt. % carbon content and in the range of between 20-50 wt. % oxygen content, on a dry basis or moisture-free basis. In certain embodiments, for example, the liquid biomass may have in the range of between 50-60 wt. % carbon content and in the range of between 35-40 wt. % oxygen content, on a dry basis or moisture-free basis.

In certain embodiments, for example, the liquid biomass may comprise a carbon content level of at least 40 wt. % of the carbon content contained in the biomass from which it may be derived. In certain embodiments, for example, the liquid biomass may comprise a carbon content level of at least 45 wt. %, such as at least 50 wt. %, at least 55 wt. %, at least 60 wt. %, at least 65 wt. %, at least 70 wt. %, at least 75 wt. %, at least 80 wt. %, at least 85 wt. %, at least 90 wt. %, or at least 95 wt. % of the carbon content contained in the biomass from which it may be derived. In certain embodiments, for example, the liquid biomass may comprise a carbon content level in the range of between 40 wt. % and 100 wt. % of the carbon content contained in the biomass from which it may be derived. In certain embodiments, for example, the liquid biomass may comprise a carbon content level in the range of 40-95 wt. %, in the range of 40-90 wt. %, in the range of 40-80 wt. %, in the range of 50-90 wt. %, in the range of 50-75 wt. %, in the range of 60-90 wt. %, in the range of 60-80 wt. %, in the range of 70-95 wt. %, in the range of 70-80 wt. %, or in the range of 70-90 wt. % of the carbon content contained in the biomass from which it may be derived. In certain embodiments, the liquid biomass may comprise a carbon content level lower than that of a petroleum fraction feedstock. In certain embodiments, for example, the liquid biomass may comprise a carbon content level in the range of in the range of 35-80 wt. %, on a dry basis moisture-free basis, such as in the range of 40-75 wt. %, in the range of 45-70 wt. %, in the range of 50-65 wt. %, in the range of 50-60 wt. %, or in the range of 54-58 wt. %, on a dry basis or moisture-free basis.

In certain embodiments, for example, the liquid biomass may have a kinematic viscosity in the range of 15 cSt to 180 cSt at 40° C., 15 cSt to 30 cSt, 30 cSt to 40 cSt, 40 cSt to 80 cSt, 50 cSt to 70 cSt, 55 cSt to 65 cSt, or 80 cSt to 200 cSt at 40° C. In certain embodiments, for example, the liquid biomass may have a kinematic viscosity in the range of 1 cSt to 15 cSt at 40° C., for example a kinematic viscosity in the range of 1 cSt to 10 cSt, 1 cSt to 5 cSt, 5 cSt to 15 cSt, or a kinematic viscosity in the range of 10 cSt to 15 cSt at 40° C.

By way of example, Tables 1 and 2 provide analyses of several suitable unenriched liquid biomasses which were prepared according to one or more of the procedures described in U.S. Pat. Nos. 7,905,990, 5,961,786, and 5,792,340, each of which is incorporated by reference in their entirety.

TABLE 1

Analytical Results for Alcell Lignin -
Mild Run (LS-3) & Severe Run (LS-4)

|  | LS-3 | LS-4 |
|---|---|---|
| Volatiles (wt %) | 14.7 | 27.9 |
| Moisture Content (wt %) | 1.0 | 0.9 |
| Ash content (wt %) | 0.05 | 1.00 |
| Elemental (wt %, MAF) | | |
| Carbon | 68.68 | 73.04 |
| Hydrogen | 7.16 | 6.52 |
| Nitrogen | 0.00 | 0.01 |
| Oxygen (difference) | 24.16 | 20.43 |
| Hydroxyl (wt %) | 7.54 | 7.50 |
| Methoxyl (wt %) | 15.68 | 1.02 |
| Sequential Solubility (wt %) | | |
| Diethyl Ether | 41.8 | 40.3 |
| Ethyl Acetate | 48.9 | 42.4 |
| Methanol | 0.2 | 0.6 |
| Residue | 9.1 | 16.7 |
| Fractionation (wt %) | | |
| Organic Acids | 31.7 | 3.6 |
| Phenols & Neutrals | 45.0 | 81.7 |
| Residue | 23.3 | 14.1 |

TABLE NOTE:
Mild Run (LS-3) was rapid thermal processed at about 500° C. and the Severe Run (LS-4) was rapid thermal processed at about 700° C.

TABLE 2

Analytical Results of Liquid biomass Derived from Wood Biomass

| | LABORATORY | | | | | | | |
|---|---|---|---|---|---|---|---|---|
| | 1) | 1) | 2) | 3) | 3) | 4) | 5) | AVERAGE |
| SPECIFIC GRAVITY | 1.19 | 1.20 | 1.21 | 1.217 | 1.226 | 1.186 | 1.188 | 1.20 |
| WATER CONTENT (% by wt) | 26 | 27 | 21 | 20.5 | 21 | 28.1 | | 23.9 |
| CHAR CONTENT (% by wt) | 2.0 | 0.6 | | 1.4 | 2.2 | 5.5 | 2.2 | 2.3 |
| HIGHER HEATING (BTU/lb) | 7267 | 7310 | 9245 | 7525 | 7955 | 6536 | 6880 | 7525 |
| ELEMENTAL (%, MAF) | | | | | | | | |
| CARBON | 55.1 | | 53.63 | 55.5 | 52.8 | 58.27 | 51.5 | 54.5 |
| HYDROGEN | 6.7 | | 6.06 | 6.7 | 6.9 | 5.5 | 6.8 | 6.4 |
| NITROGEN | 0.15 | | 0.24 | 0.1 | <0.1 | 0.39 | 0.17 | 0.18 |

TABLE 2-continued

Analytical Results of Liquid biomass Derived from Wood Biomass

| | LABORATORY | | | | | | |
|---|---|---|---|---|---|---|---|
| 1) | 1) | 2) | 3) | 3) | 4) | 5) | AVERAGE |
| SULPUR | | 0.02 | | | <0.14 | 0.07 | <.001 |
| ASH (% by wt) | | | 0.13 | 0.15 | 0.22 | 0.13 | 0.16 |

TABLE NOTES:
The liquid biomass derived from the Wood Biomass was analyzed by the following labs:
1) Universite Catholique de Louvain, Belgium;
2) ENEL, Centro Ricerca Termica, Italy;
3) VTT, Laboratory of Fuel and Process Technology, Finland;
4) CANMET, Energy Research Laboratories, Canada;
5) Commercial Testing and Engineering Co., U.S.A.

In certain embodiments, for example, the liquid biomass may comprise an energy content level of at least 30% of the energy content contained in the biomass from which it may be derived. In certain embodiments, for example, the liquid biomass may comprise an energy content level of at least 45%, such as at least 55%, at least 60%, at least 65%, at least 70%, at least 75%, at least 80%, at least 85%, at least 90%, or at least 95% of the energy content contained in the biomass from which it may be derived. In certain embodiments, for example, the liquid biomass may comprise an energy content level in the range of between 50% and 98% of the energy content contained in the biomass from which it may be derived. In certain embodiments, for example, the liquid biomass may comprise a energy content level in the range of between 50% and 90%, between 50% and 75%, between 60% and 90%, between 60% and 80%, between 70% and 95%, between 70% and 80%, or between 70% and 90% of the energy content contained in the biomass from which it may be derived.

In certain embodiments, for example, the liquid biomass may comprise an energy content level lower than that of a petroleum fuel. In certain embodiments, for example, the liquid biomass may comprise a energy content level in the range of between 30-95%, on a dry basis (moisture-free basis), relative to the energy content of a petroleum feedstock, such as between 40-90%, between 45-85%, between 50-80%, between 50-60%, or between 54-58%, on a dry basis or moisture-free basis, relative to the energy content of a petroleum feedstock. In certain embodiments, for example, the liquid biomass may have energy content in the range of between 30-90%, relative to the petroleum fraction feedstock energy content. In certain embodiments, for example, the liquid biomass may have an energy content of 35%, 40%, 45%, 50%, 55%, 60%, 65%, 70%, 75%, 80%, or 85%, relative to the petroleum fraction feedstock energy content.

Certain embodiments may provide, for example, methods, processes, systems, or apparatus to reduce, remove, and/or recover one or more contaminants (for example one or more of the foregoing disclosed contaminants) present in a liquid biomass (for example one or more of the foregoing disclosed liquid biomasses), comprising: complexing the one or more contaminants with a complexing agent to form one or more complexes.

In certain embodiments, for example, the one or more contaminants present in the liquid biomass may be reduced by at least 25 wt. % to below 1000 ppm in the liquid biomass, for example reduced by at least 25 wt. % to below 200 ppm, by at least 25 wt. % to below 75 ppm, by at least 25 wt. % to below 50 ppm, by at least 50 wt. % to below 1000 ppm, at least 50 wt. % to below 200 ppm, by at least 50 wt. % to below 75 ppm, by at least 50 wt. % to below 50 ppm, by at least 75 wt. % to below 1000 ppm, by at least 75 wt. % to below 200 ppm, by at least 75 wt. % to below 75 ppm, by at least 75 wt. % to below 50 ppm, by at least 90 wt. % to below 1000 ppm, by at least 90 wt. % to below 200 ppm, by at least 90 wt. % to below 75 ppm, or by at least 90 wt. % to below 50 ppm. In certain embodiments, for example, the total metal content of the liquid biomass may be reduced by at least 25 wt. % to below 1000 ppm in the liquid biomass, for example reduced by at least 25 wt. % to below 200 ppm, by at least 25 wt. % to below 75 ppm, by at least 25 wt. % to below 50 ppm, by at least 50 wt. % to below 1000 ppm, at least 50 wt. % to below 200 ppm, by at least 50 wt. % to below 75 ppm, by at least 50 wt. % to below 50 ppm, by at least 75 wt. % to below 1000 ppm, by at least 75 wt. % to below 200 ppm, by at least 75 wt. % to below 75 ppm, by at least 75 wt. % to below 50 ppm, by at least 90 wt. % to below 1000 ppm, by at least 90 wt. % to below 200 ppm, by at least 90 wt. % to below 75 ppm, or by at least 90 wt. % to below 50 ppm. In certain embodiments, for example, the total alkali and alkaline earth metal content of the liquid biomass may be reduced by at least 25 wt. % to below 1000 ppm in the liquid biomass, for example reduced by at least 25 wt. % to below 200 ppm, by at least 25 wt. % to below 75 ppm, by at least 25 wt. % to below 50 ppm, by at least 50 wt. % to below 1000 ppm, at least 50 wt. % to below 200 ppm, by at least 50 wt. % to below 75 ppm, by at least 50 wt. % to below 50 ppm, by at least 75 wt. % to below 1000 ppm, by at least 75 wt. % to below 200 ppm, by at least 75 wt. % to below 75 ppm, by at least 75 wt. % to below 50 ppm, by at least 90 wt. % to below 1000 ppm, by at least 90 wt. % to below 200 ppm, by at least 90 wt. % to below 75 ppm, or by at least 90 wt. % to below 50 ppm. In certain embodiments, for example, a metal present in the liquid biomass (for example calcium, magnesium, barium, or potassium) may be reduced by at least 25 wt. % to below 1000 ppm in the liquid biomass, for example reduced by at least 25 wt. % to below 200 ppm, by at least 25 wt. % to below 75 ppm, by at least 25 wt. % to below 50 ppm, by at least 50 wt. % to below 1000 ppm, at least 50 wt. % to below 200 ppm, by at least 50 wt. % to below 75 ppm, by at least 50 wt. % to below 50 ppm, by at least 75 wt. % to below 1000 ppm, by at least 75 wt. % to below 200 ppm, by at least 75 wt. % to below 75 ppm, by at least 75 wt. % to below 50 ppm, by at least 90 wt. % to below 1000 ppm, by at least 90 wt. % to below 200 ppm, by at least 90 wt. % to below 75 ppm, or by at least 90 wt. % to below 50 ppm. In certain embodiments, for example, chlorine present in the liquid biomass may be reduced by at least 25 wt. % to below 1000 ppm in the liquid biomass, for example reduced by at least 25 wt. % to below 200 ppm, by at least 25 wt. % to below 75 ppm, by at least 25 wt. % to below 50 ppm, by at least 50 wt. % to below 1000 ppm, at least 50 wt. % to below 200 ppm, by at least 50 wt. % to below 75 ppm, by at least 50 wt. % to below 50 ppm, by at least 75 wt. % to below 1000 ppm, by at least 75 wt. % to below 200 ppm, by at least 75 wt. % to below 75 ppm, by at least 75 wt. % to below 50 ppm, by at least 90 wt. % to below 1000 ppm, by at least 90 wt. % to below 200 ppm, by at least 90 wt. % to below 75 ppm, or by at least 90 wt. % to below 50 ppm.

In certain embodiments, for example, the complexing may comprise contacting the complexing agent for a duration of time with the one or more contaminants. In certain embodiments, for example, the duration may be at least 2 hours. In certain embodiments, for example, the duration may be less than 2 hours. In certain embodiments, for example, the duration may be in the range of 1-4 hours, for example the duration may be in the range of 1-3 hours, in the range of 1.5-2.5 hours, in the range of 2-3 hours, or the duration may be in the range of 3-4 hours.

In certain embodiments, for example, the complexing agents may be introduced in a solid, liquid, or gaseous state. In certain embodiments, for example, the complexing agent may be a particle (for example a powder). In certain embodiments, for example, the complexing agent may partially or fully dissolve in the liquid biomass. In certain embodiments, for example, the complexing agent may be partially or fully insoluble in the liquid biomass. In certain embodiments, for example, the complexing agent may be relatively immobilized in a fixed bed.

In certain embodiments, for example, the complexing agent may comprise a chelating agent. In certain further embodiments, for example, the complexing agent may comprise oxalic acid. In certain embodiments, for example, the complexing agent may comprise kaolin. In certain embodiments, for example, the complexing agent may comprise a coagulant. In certain embodiments, for example, the complexing agent may comprise a flocculent. In certain embodiments, for example, the complexing agent may comprise an ion exchange material. In certain embodiments, for example, the complexing agent may comprise a cationic ion exchange material. In certain embodiments, for example, the complexing agent may comprise an acidic ion exchange material. In certain embodiments, for example, the complexing agent may comprise an anionic ion exchange material. In certain embodiments, for example, the complexing agent may comprise a basic ion exchange material.

In certain embodiments, for example, the complexing agent may comprise, relative to the weight of the liquid biomass, less than 3 wt. % oxalic acid, less than 2.5 wt. % oxalic acid, less than 2 wt. % oxalic acid, less than 1.5 wt. % oxalic acid, less than 1 wt. % oxalic acid, less than 0.8 wt. % oxalic acid, less than 0.6 wt. % oxalic acid, less than 0.5 wt. % oxalic acid, less than 0.4 wt. % oxalic acid, less than 0.3 wt. % oxalic acid, less than 0.25 wt. % oxalic acid, less than 0.2 wt. % oxalic acid, less than 0.15 wt. % oxalic acid, less than 0.1 wt. % oxalic acid, or the complexing agent may comprise less than 0.05 wt. % oxalic acid. In certain embodiments, for example, the complexing agent may comprise, relative to the weight of the liquid biomass, in the range of 0.05-3 wt. % oxalic acid, for example the complexing agent may comprise in the range of 0.05-2 wt. % oxalic acid, in the range of 0.05-1 wt. % oxalic acid, in the range of 0.05-0.5 wt. % oxalic acid, in the range of 0.1-0.5 wt. % oxalic acid, in the range of 0.1-0.4 wt. % oxalic acid, in the range of 0.1-0.3 wt. % oxalic acid, or the complexing agent may comprise in the range of 0.15-0.25 wt. % oxalic acid. In certain embodiments, for example, the oxalic acid may be a laboratory grade oxalic acid. In certain embodiments, for example, the oxalic acid may be a commercial grade oxalic acid. In certain embodiments, for example, the oxalic acid may be anhydrous. In certain embodiments, for example, the oxalic acid may be a hydrate.

In certain embodiments, for example, the complexing agent may comprise a cationic ion-exchange resin. In certain embodiments, for example, the cationic ion-exchange resin may comprise strongly acidic cation-exchange resins having sulfonic acid groups. In certain further embodiments, for example, the resin may be in the protonated form, for example, all of the active groups are —$SO_3H$. In certain embodiments, for example, the cationic ion-exchange resin may be a neutralized sulfonic acid resin, wherein some or all of the protons have been exchanged by a cation such as lithium, sodium, potassium, magnesium, barium, and/or calcium. In certain further embodiments, for example, cationic ion-exchange resin may be supplied with alternate counterions (for example sodium ions), and the acid form may be activated prior to use by treatment with aqueous acid (for example hydrochloric, nitric, and/or sulfuric acid). In certain embodiments, for example, the cationic ion-exchange resin may comprise a sulfonated copolymer of styrene. In certain embodiments, for example, the cationic ion-exchange sulfonic acid resin may be a macroreticular resin, for example a macroreticular resin having two continuous phases: a continuous pore phase and a continuous gel polymeric phase. In certain further embodiments, for example, the continuous gel polymeric phase may be structurally composed of small spherical microgel particles agglomerated together to form clusters, which may, in turn, form interconnecting pores. In certain further embodiments, for example, the cationic ion-exchange sulfonic acid resins may comprise a macroreticular ion exchange resins having a surface area in the range of 7-1500 $m^2/g$, and an average pore diameter in the range of 5-10000 nm. In certain embodiments, for example, the macroreticular resins may be suitable for continuous column ion-exchange applications where it may be desirable to minimize resin swelling/shrinking.

In certain embodiments, for example, the cationic ion-exchange resin may comprise a gel-type resin. In certain further embodiments, for example, the gel-type resin may be translucent. In certain embodiments, for example, the gel-type resin may have no permanent pore structure. In certain embodiments, for example, the pore structures of the gel-type resins may be determined by the distance between the polymer chains and crosslinks which vary with the crosslink level of the polymer, the polarity of the solvent, and the operating conditions. In certain embodiments, for example, the gel-type resins may be suitable for batch ion-exchange applications. In certain embodiments, for example, either a gel-type resin or a macroreticular resin may be suitable for batch ion-exchange applications and/or continuous column ion-exchange applications.

In certain embodiments, for example, suitable cationic ion exchange resins include those manufactured by Dow Chemical Co., Midland, Mich. (USA) under the tradenames/trademarks DOWEX® MARATHON C, DOWEX® MONOSPHERE C-350, DOWEX® HCR-S/S, DOWEX® MARATHON MSC, DOWEX® MONOSPHERE 650C, DOWEX® HCR-W2, DOWEX® MSC-1, DOWEX® HGR NG (H), DOWE® DR-G8, DOWEX® 88, DOWEX® MONOSPHERE 88, DOWEX® MONOSPHERE C-600 B, DOWEX® MONOSPHERE M-31, DOWEX® MONOSPHERE DR-2030, DOWEX® M-31, DOWEX® G-26

(H), DOWEX® 50W-X4, DOWEX® 50W-X8, DOWEX® 66, those manufactured by Rohm and Haas, Philadelphia, Pa. (USA) under the tradenames/trademarks Amberlyst® 131, Amberlyst® 15, Amberlyst® 16, Amberlyst® 31, Amberlyst® 33, Amberlyst® 35, Amberlyst® 36, Amberlyst® 39, Amberlyst® 40 Amberlyst® 70, Amberlite® FPC11, Amberlite® FPC22, Amberlite® FPC23, those manufactured by Brotech Corp., Bala Cynwyd, Pa. (USA) under the tradnames/trademarks Purofine® PFC150, Purolite® C145, Purolite® C150, Purolite® C160, Purofine® PFC100, Purolite® C100, and/or those manufactured by Thermax Limited Corp., Novi, Mich. (USA) under the tradename/trademark Monoplus™ S100 and Tulsion® T42.

In certain embodiments, for example, suitable anionic ion exchange resins include gel anion resin consisting of a styrene divinylbenzene polymer matrix supplied in the hydroxide form (for example USF A-284 OH), styrene divinylbenzene polymer matrix functionalized with quaternary amine supplied in the hydroxide form (for example USF A-674 OH), a strongly basic, macroreticular, Type I, quaternary ammonium anion exchange resin (for example Dow® Ambersep™ 900 OH), Dowex™ Marathon™ A Anion Exchange Resin, Dowex™ Marathon™ 550A (OH), and Dowex™ Monosphere™ 550A (OH).

In certain embodiments, for example, at least one of the one or more complexes may comprise a metal chelate. In certain embodiments, for example, at least one of the one or more complexes may comprise a contaminant bound to a surface or a bead (for example an ion exchange surface or bead). In certain embodiments, for example, at least one of the one or more complexes may be dissolved in the liquid biomass. In certain embodiments, at least one of the one or more complexes may form a solid-state complex (for example, a dissolved contaminant and a dissolved complexing agent combine to form a solid-state complex precipitate). In certain embodiments, for example, at least one of the one or more complexes may be suspended (for example suspended particles) in the liquid biomass.

Certain embodiments may provide, for example, methods, processes, systems, or apparatus to reduce, remove, and/or recover any one or more of the foregoing contaminants present in any disclosed foregoing liquid biomass, comprising: complexing at least a portion of the one or more contaminants with any of the foregoing complexing agents to form one or more complexes, and separating at least a portion of the one or more complexes from the liquid biomass.

In certain embodiments, for example, the separating may comprise passing the liquid biomass through a fixed bed of the complexing agent(s) followed by removing the liquid biomass from the presence of the complexing agent(s).

In certain embodiments, for example, where the at least a portion of the one or more contaminants forms a solid-state complex (for example a precipitate or a complex with one or more beads), the separating may comprise passing the liquid biomass through a cyclone (for example a hydrocyclone), for example a high efficiency cyclone, to obtain a low solids liquid biomass fraction and a high solids fraction.

In certain embodiments, for example, where the at least a portion of the one or more contaminants forms a solid-state complex (for example a precipitate or a complex with one or more beads), the separating may comprise filtering the liquid biomass. In certain embodiments, for example, a suitable filters may comprise a gag filter, a candle filter, a pressure leaf filter, a deep filter bed filter, a vacuum filter drum, a filter press, a centrifuge/decanter, a structured metal media, or a sintered metal filter media. In certain embodiments, for example, the filtering may comprise passing the liquid biomass through a high flux filter. In certain embodiments, for example, the filtering may comprise passing the liquid biomass through a filter assembly. In certain further embodiments, for example, the filter assembly may comprise at least one redundant filter. In certain further embodiments, for example, the redundant filter may be used when servicing a primary filter. In certain embodiments, for example, the redundant filter may be used when a primary filter is offline. In certain embodiments, for example, the filter assembly may comprise two or more filters arranged in parallel (for example a duplex or a triplex configuration). In certain further embodiments, the two or more parallel filters may be rotated in and out of service according to a pre-determined maintenance schedule.

In certain embodiments, for example, the liquid biomass may be adjusted to a separating temperature of at least 30° C., for example a separating temperature of at least 40° C., at least 45° C., at least 50° C., at least 60° C., at least 70° C., or adjusted to a separating temperature of at least 80° C. In certain further embodiments, for example, the liquid biomass may be adjusted to a separating temperature in the range of 20-80° C., for example a separating temperature in the range of 25-70° C., in the range of 25-50° C., in the range of 30-40° C., in the range of 40-80° C., in the range of 50-75° C., in the range of 60-75° C., or adjusted to a separating temperature in the range of 65-75° C. For example, in certain embodiments the temperature may be adjusted before, during, or after the complexing such that separating occurs at a temperature in the range of 30-40° C.

In certain embodiments, for example, the liquid biomass may be adjusted to a separating viscosity of at least 30 cP, for example a separating viscosity of at least 40 cP, at least 45 cP, at least 50 cP, at least 60 cP, at least 70 cP, or adjusted to a separating viscosity of at least 80 cP. In certain further embodiments, for example, the liquid biomass may be adjusted to a separating viscosity in the range of 20-80 cP, for example a separating viscosity in the range of 25-70 cP, in the range of 25-50 cP, in the range of 30-40 cP, in the range of 40-80 cP, in the range of 50-75 cP, in the range of 60-75 cP or adjusted to a separating viscosity in the range of 65-75 cP. For example, in certain embodiments the temperature may be adjusted before, during, or after the complexing such that separating occurs at a viscosity in the range of 30-40 cP. In certain embodiments, for example, the separating viscosity the liquid biomass may be adjusted by controlling the temperature of the liquid biomass. In certain embodiments, for example, the separating viscosity of the liquid biomass may be adjusted by introducing an additive (for example an alcohol, for example ethanol) to the liquid biomass. In certain further embodiments, for example, the separating viscosity the liquid biomass may be adjusted by introducing 0.5-5 wt. % of an alcohol (for example 0.5-5 wt. % of ethanol) to the liquid biomass, relative to the weight of the liquid biomass.

In certain embodiments, for example, following complexing with less than 0.2 wt. % oxalic acid followed by the separating, the total metal content of the liquid biomass may be reduced by at least 25 wt. % to below 1000 ppm in the liquid biomass, for example reduced by at least 25 wt. % to below 200 ppm, by at least 25 wt. % to below 75 ppm, by at least 25 wt. % to below 50 ppm, by at least 50 wt. % to below 1000 ppm, at least 50 wt. % to below 200 ppm, by at least 50 wt. % to below 75 ppm, by at least 50 wt. % to below 50 ppm, by at least 75 wt. % to below 1000 ppm, by at least 75 wt. % to below 200 ppm, by at least 75 wt. % to below 75 ppm, by at least 75 wt. % to below 50 ppm, by at least 90 wt. % to below 1000 ppm, by at least 90 wt. % to below 200 ppm, by at least 90 wt. % to below 75 ppm, or by at least 90 wt. % to below 50 ppm. In certain embodiments, for example, following complexing with less than 0.2 wt. % oxalic acid followed by the separating, the total alkali and alkaline earth metal content of the liquid biomass (combined) may be reduced by at least 25 wt. % to below 1000 ppm in the liquid biomass, for example reduced by at least 25 wt. % to below 200 ppm, by at least 25 wt. % to below 75 ppm, by at least 25 wt. % to below 50 ppm, by at least 50 wt. % to below 1000 ppm, at least 50 wt. % to below 200 ppm, by at least 50 wt. % to below 75 ppm, by at least 50 wt. % to below 50 ppm, by at least 75 wt. % to below 1000 ppm, by at least 75 wt. % to below 200 ppm, by at least 75 wt. % to below 75 ppm, by at least 75 wt. % to below 50 ppm, by at least 90 wt. % to below 1000 ppm, by at least 90 wt. % to below 200 ppm, by at least 90 wt. % to below 75 ppm, or by at least 90 wt. % to below 50 ppm.

In certain embodiments, for example, following complexing with less than 0.2 wt. % oxalic acid followed by the separating, the calcium content of the liquid biomass may be reduced by at least 50 wt. % (for example to below 100 ppm, 50 ppm, or to below 25 ppm). In certain embodiments, for example, following complexing with less than 0.9 wt. % oxalic acid followed by the separating, the calcium content of the liquid biomass may be reduced by at least 90 wt. % (for example to below 200 ppm, 100 ppm, or to below 50 ppm). In certain embodiments, for example, following complexing with less than 0.2 wt. % oxalic acid followed by the separating, the magnesium content of the liquid biomass may be reduced by at least 80 wt. % (for example to below 30 ppm, 10 ppm, or to below 5 ppm). In certain embodiments, for example, following complexing with less than 0.9 wt. % oxalic acid followed by the separating, the magnesium content of the liquid biomass may be reduced by at least 90 wt. % (for example to below 50 ppm, 20 ppm, or to below 10 ppm). In certain embodiments, for example, following complexing with less than 0.2 wt. % oxalic acid followed by the separating, the potassium content of the liquid biomass may be reduced by at least 90 wt. % (for example to below 10 ppm, 5 ppm, or to below 1 ppm). In certain embodiments, for example, following complexing with less than 0.9 wt. % oxalic acid followed by the separating, the potassium content of the liquid biomass may be reduced by at least 90 wt. % (for example to below 200 ppm, 100 ppm, or to below 50 ppm).

In certain embodiments, for example, following complexing with in the range of 1-8 wt. % anionic ionic exchange resin, relative to the weight of the liquid biomass, followed by the separating, the chlorine content of the liquid biomass may be reduced by at least 25 wt. % to below 1000 ppm in the liquid biomass, for example reduced by at least 25 wt. % to below 200 ppm, by at least 25 wt. % to below 75 ppm, by at least 25 wt. % to below 50 ppm, by at least 50 wt. % to below 1000 ppm, at least 50 wt. % to below 200 ppm, by at least 50 wt. % to below 75 ppm, by at least 50 wt. % to below 50 ppm, by at least 75 wt. % to below 1000 ppm, by at least 75 wt. % to below 200 ppm, by at least 75 wt. % to below 75 ppm, by at least 75 wt. % to below 50 ppm, by at least 90 wt. % to below 1000 ppm, by at least 90 wt. % to below 200 ppm, by at least 90 wt. % to below 75 ppm, or by at least 90 wt. % to below 50 ppm. In certain further embodiments, for example, complexing with at least 1 wt. % of the anionic ionic exchange resin may be effective to reduce the chlorine content by at least 50 wt. % to below 350 ppm, for example complexing with at least 2 wt. % of the anionic ionic exchange resin may be effective to reduce the chlorine content by at least 60 wt. % to below 200 ppm, for example complexing with at least 4 wt. % of the anionic ionic exchange resin may be effective to reduce the chlorine content by at least 70 wt. % to below 150 ppm, for example complexing with at least 8 wt. % of the anionic ionic exchange resin may be effective to reduce the chlorine content by at least 75 wt. % to below 125 ppm.

Certain embodiments may provide, for example, methods, processes, systems, or apparatus to reduce, remove, and/or recover a plurality of any one or more of the foregoing contaminants present in any foregoing liquid biomass, comprising: complexing at least a portion of the plurality of any one or more of the foregoing contaminants with a plurality of any of the foregoing complexing agents to form one or more complexes, and separating at least a portion of the one or more complexes from the liquid biomass.

In certain embodiments, for example, the plurality of any of the foregoing complexing agents may be present in the liquid biomass at a loading in the range of 0.25-25 times the concentration, on a weight basis, of the plurality of any one or more of the foregoing contaminants, for example in the range of 8-13 times, 10-12 times, or in the range of 12-20 times the concentration of the plurality of any one or more of the foregoing contaminants, or in the range of 0.5-5 times, for example in the range of 0.75-3 times, 1-2 times, or in the range of 1-1.5 times the concentration of the plurality of any one or more of the foregoing contaminants.

In certain embodiments, for example, a metal chelating agent (for example oxalic acid) may be present in the liquid biomass at a loading in the range of 0.25-25 times the total metal concentration (inclusive of metal present in solids present in the liquid biomass), on a weight basis, for example in the range of 0.5-5 times, for example in the range of 0.75-3 times, 1-2 times, or in the range of 1-1.5 times the total metal concentration. In certain embodiments, for example, a metal chelating agent (for example oxalic acid) may be present in the liquid biomass at a loading in the range of 0.25-25 times the total metal concentration (inclusive of metal present in solids present in the liquid biomass), on a weight basis, for example in the range of 0.25-0.75 times, for example in the range of 0.75-1.25 times, 1.25-2 times, 2-4 times, 4-8, 8-10 times, 10-15 times, 15-20 times or in the range of 20-25 times the total metal concentration. In certain embodiments, for example, a metal chelating agent (for example oxalic acid) may be present in the liquid biomass at a loading in the range of 0.25-25 times the total alkali and alkaline earth metal concentration (combined) (inclusive of alkali and alkaline earth metal present in solids present in the liquid biomass), on a weight basis, for example in the range of 0.5-5 times, for example in the range of 0.75-3 times, 1-2 times, or in the range of 1-1.5 times the total alkali and alkaline earth metal concentration. In certain embodiments, for example, a metal chelating agent (for example oxalic acid) may be present in the liquid biomass at a loading in the range of 0.25-25 times the total alkali and alkaline earth metal concentration (combined) (inclusive of alkali and alkaline earth metal present in solids present in the liquid biomass), on a weight basis, for example in the range of 0.25-0.75 times, for example in the range of 0.75-1.25 times, 1.25-2 times, 2-4 times, 4-8, 8-10 times, 10-15 times, 15-20 times or in the range of 20-25 times the total alkali and alkaline earth metal concentration (combined).

In certain embodiments, for example, an ion exchange material (for example a cationic or acidic ion exchange resin) may be present in the liquid biomass at a loading in the range of 1-25 times the total metal concentration (inclusive of metal present in solids present in the liquid biomass), on a weight basis, for example in the range of 5-25 times, for example in the range of 8-13 times, 10-12 times, or in the range of 12-20 times the total metal concentration. In certain embodiments, for example, an ion exchange material (for example a cationic or acidic ion exchange resin) may be present in the liquid biomass at a loading in the range of 1-25 times the total metal concentration (inclusive of metal present in solids present in the liquid biomass), on a weight basis, for example in the range of 2-12 times, for example in the range of 4-7 times, 5-6 times, or in the range of 6-10 times the total metal concentration. In certain embodiments, for example, an ion exchange material (for example a cationic or acidic ion exchange resin) may be present in the liquid biomass at a loading in the range of 0.25-25 times the total metal concentration (inclusive of metal present in solids present in the liquid biomass), on a weight basis, for example in the range of 0.25-0.75 times, for example in the range of 0.75-1.25 times, 1.25-2 times, 2-4 times, 4-8, 8-10 times, 10-15 times, 15-20 times or in the range of 20-25 times the total metal concentration. In certain embodiments, for example, an ion exchange material (for example a cationic or acidic ion exchange resin) may be present in the liquid biomass at a loading in the range of 1-25 times the total alkali and alkaline earth metal concentration (combined) (inclusive of alkali and alkaline earth metal present in solids present in the liquid biomass), on a weight basis, for example in the range of 5-25 times, for example in the range of 8-13 times, 10-12 times, or in the range of 12-20 times the total alkali and alkaline earth metal concentration (combined). In certain embodiments, for example, an ion exchange material (for example a cationic or acidic ion exchange resin) may be present in the liquid biomass at a loading in the range of 1-25 times the total alkali and alkaline earth metal concentration (combined) (inclusive of alkali and alkaline earth metal present in solids present in the liquid biomass), on a weight basis, for example in the range of 2-12 times, for example in the range of 4-7 times, 5-6 times, or in the range of 6-10 times the total alkali and alkaline earth metal concentration (combined). In certain embodiments, for example, an ion exchange material (for example a cationic or acidic ion exchange resin) may be present in the liquid biomass at a loading in the range of 0.25-25 times the total alkali and alkaline earth metal concentration (combined) (inclusive of alkali and alkaline earth metal present in solids present in the liquid biomass), on a weight basis, for example in the range of 0.25-0.75 times, for example in the range of 0.75-1.25 times, 1.25-2 times, 2-4 times, 4-8, 8-10 times, 10-15 times, 15-20 times or in the range of 20-25 times the total alkali and alkaline earth metal concentration (combined).

In certain embodiments, for example, an ion exchange material (for example an anionic or basic ion exchange resin) may be present in the liquid biomass at a loading in the range of 0.5-20 wt. % relative to the weight of the liquid biomass for example in the range of 0.5-2.5 wt. %, 2.5-5 wt. %, 5-9 wt. %, 9-12 wt. %, 12-15 wt. %, or in the range of 15-20 wt. %. In certain embodiments, for example, an ion exchange material (for example an anionic or basic ion exchange resin) may be present in the liquid biomass at a loading of approximately 1 wt. %, 2 wt. %, 4 wt. %, or a loading of approximately 8 wt. %.

Certain embodiments may provide, for example, methods, processes, systems, or apparatus to reduce a plurality contaminants (for example, a plurality of one of the foregoing contaminants, or a plurality of several or all of the foregoing contaminants) present in a liquid biomass, comprising: complexing a first contaminant with a dissolved first complexing agent (for example, one of the foregoing described complexing agents) to form a first complex, followed by further complexing a second contaminant (for example a second contaminant that is the same type of contaminant as the first contaminant, or a second contaminant that is a different type of contaminant than the first contaminant) with solid second complexing agent (for example, the same type of complexing agents as a the first complexing agent, or one of the foregoing described complexing agents that is a different type of complexing agent than the first complexing agent).

In certain embodiments, for example, the second contaminant may not form a complex with the first complexing agent. In certain embodiments, for example, the first contaminant may not form a complex with the second complexing agent. In certain embodiments, for example, the second contaminant may not form a solid complex in the liquid biomass with the first complexing agent. In certain embodiments, for example, the second contaminant may form a complex with the first complexing agent, wherein the complex is soluble (or dissolves) in the liquid biomass. In certain embodiments, for example, the second complexing agent may have a greater affinity for the second contaminant than does the first complexing agent.

In certain embodiments, for example, the complexing and the further complexing occur simultaneously, for example the first and second complexing agents may be added together (for example as a mixture or in a solution) to a vessel where they contact the liquid biomass. In certain embodiments, for example, the complexing and the further complexing may occur in a common space-volume. In certain embodiments, for example, the complexing and the further complexing may occur sequentially, for example the first complexing agent may be brought into contact with the liquid biomass before the second complexing agent is brought into contact with the liquid biomass. In certain embodiments, for example, the first complex may be at least partially separated from the liquid biomass (for example by filtration or by cyclone separation) prior to the further complexing.

In certain embodiments, for example, the first complexing agent may be a metal chelating agent. In certain embodiments, for example, the first contaminant may be dissolved (for example the first contaminant may be an ion) in the liquid biomass. In certain embodiments, for example, the first complex may be a solid-state complex (for example a precipitate). In certain embodiments, for example, the second contaminant may be dissolved in the liquid biomass. In certain further embodiments, for example, the metal chelating agent may be oxalic acid present at a concentration of less than 0.2 wt. %, relative to the weight of the liquid biomass.

In certain embodiments, for example, the second complexing agent may be a complexing agent present in a carrier (for example a liquid carrier, such as a liquid, such as a liquid biomass). In certain embodiments, for example, the second complexing agent may be a solid-state complexing agent (for example an ion exchange resin). In certain embodiments, for example, the second complexing agent may be a regenerable and/or a regenerated complexing agent (for example the second complexing agent may be a regenerable ion exchange resin which may be regenerated by removing captured contaminants). In certain embodiments, for example, the liquid biomass may be treated with a cationic ion exchange material in a fixed bed, whereby a residual of the liquid biomass may remain on the spent ion-exchange resin. In certain further embodiments, for example, at least a portion of the residual may be recovered by purging the ion-exchange column with gas such as nitrogen, air or the like. In certain embodiments, for example, at least a portion of the residual may be recovered by washing the spent ion-exchange resin with about 1 to about 10 column volumes of a suitable solvent selected from the group consisting of methanol, ethanol, acetone, or combinations thereof. In certain embodiments, for example, small amounts of residual oil may remain on the cationic ion exchange resin. In certain embodiments, for example, the recovered residual portion may be further processing and/or added to the liquid biomass product stream). In certain embodiments, for example, the recovered residual may contain residual solvent, which may increase the storage stability of the liquid biomass product. In certain embodiments, for example, the addition of ethanol to biomass-derived pyrolysis oil helps to keep the oil phase stable during storage.

In certain embodiments, for example, the methods, processes, systems, or apparatus may comprise complexing a first metal contaminant with a dissolved metal chelating agent to form a metal chelate precipitate, followed by complexing (or binding) a second metal contaminant with a solid-state cationic ion exchange material. In certain embodiments, for example, the methods, processes, systems, or apparatus may comprise complexing a first metal contaminant with a dissolved metal chelating agent to form a metal chelate precipitate, followed by complexing (or binding) an anionic contaminant (for example a chlorine ion) with a solid-state anionic ion exchange material. In certain embodiments, for example, the methods, processes, systems, or apparatus may comprise complexing a first metal contaminant with a solid-state cationic ion exchange material, followed by complexing (or binding) an anionic contaminant (for example a chlorine ion) with a solid-state anionic ion exchange material.

In certain embodiments, for example, complexing with less than 0.2 wt. % oxalic acid followed by complexing with a cationic ionic exchange resin followed by separating (for example filtering), the total metal content of the liquid biomass may be reduced by at least 25 wt. % to below 1000 ppm in the liquid biomass, for example reduced by at least 25 wt. % to below 200 ppm, by at least 25 wt. % to below 75 ppm, by at least 25 wt. % to below 50 ppm, by at least 50 wt. % to below 1000 ppm, at least 50 wt. % to below 200 ppm, by at least 50 wt. % to below 75 ppm, by at least 50 wt. % to below 50 ppm, by at least 75 wt. % to below 1000 ppm, by at least 75 wt. % to below 200 ppm, by at least 75 wt. % to below 75 ppm, by at least 75 wt. % to below 50 ppm, by at least 90 wt. % to below 1000 ppm, by at least 90 wt. % to below 200 ppm, by at least 90 wt. % to below 75 ppm, or by at least 90 wt. % to below 50 ppm. In certain embodiments, for example, complexing with less than 0.2 wt. % oxalic acid followed by complexing with a cationic ionic exchange resin followed by separating (for example filtering), the total alkali and alkaline earth metal content (combined) of the liquid biomass may be reduced by at least 25 wt. % to below 1000 ppm in the liquid biomass, for example reduced by at least 25 wt. % to below 200 ppm, by at least 25 wt. % to below 75 ppm, by at least 25 wt. % to below 50 ppm, by at least 50 wt. % to below 1000 ppm, at least 50 wt. % to below 200 ppm, by at least 50 wt. % to below 75 ppm, by at least 50 wt. % to below 50 ppm, by at least 75 wt. % to below 1000 ppm, by at least 75 wt. % to below 200 ppm, by at least 75 wt. % to below 75 ppm, by at least 75 wt. % to below 50 ppm, by at least 90 wt. % to below 1000 ppm, by at least 90 wt. % to below 200 ppm, by at least 90 wt. % to below 75 ppm, or by at least 90 wt. % to below 50 ppm.

In certain embodiments, for example, the first contaminant complexing may be performed in a pyrolysis vapor condenser. In certain embodiments, for example, the liquid biomass may be a condensation product of a pyrolysis vapor (for example a pyrolysis vapor formed by rapid thermal processing of a cellulosic biomass).

In certain embodiments, for example, the methods, processes, systems, or apparatus may further comprise forming a third complex comprising a third contaminant and a third complexing agent. In certain further embodiments, for example, the methods, processes, systems, or apparatus may comprise complexing a first metal contaminant with a solid-state cationic ion exchange material, followed by complexing (or binding) a second metal contaminant with a solid-state cationic ion exchange material, and complexing (or binding) an anionic contaminant (i.e., the third contaminant) with a solid-state anionic ion exchange material (i.e., the third complexing agent). In certain embodiments, for example, the first, second, and third complexing agents may be contacted with the liquid biomass concurrently or approximately simultaneously. In certain embodiments, for example, the metal chelating agent may be contacted with the liquid biomass (for example in a pyrolysis vapor condenser), the contacted liquid biomass filtered, and the filtered liquid biomass subsequently contacted with the cationic and anionic ion exchange materials. In certain embodiments, for example, the cationic and/or anionic ion exchange materials may be in powder or bead form. In certain embodiments, for example, the cationic and anionic ion exchange materials may be immobilized (for example in one or more fixed beds, for example in one or more columns).

FIG. 1 depicts an embodiment 100 comprising passing a metal-containing liquid biomass stream 102 through a cationic ion exchange treatment 104 to form a treated liquid biomass stream 106 containing cationic ion exchange material bound to metal, optionally followed by passing the treated liquid biomass stream 106 through a filter 108 to form a reduced-metal liquid biomass stream 110.

FIG. 2 depicts an embodiment 200 comprising passing a chlorine-containing liquid biomass stream 202 through an anionic ion exchange treatment 204 to form a treated liquid biomass stream 206 containing anionic ion exchange material bound to chlorine, optionally followed by passing the treated liquid biomass stream 206 through a filter 208 to form a reduced-chorine liquid biomass stream 210.

FIG. 3 depicts an embodiment 300 comprising passing a metal-containing liquid biomass stream 302 through a metal chelating agent treatment 304 to form a treated liquid biomass stream 306 containing metal chelate precipitate, followed by passing the treated liquid biomass stream 306 through a filter 308 to form a reduced-metal liquid biomass stream 310.

FIG. 4 depicts an embodiment 400 comprising passing a metal- and chlorine-containing liquid biomass stream 402 through a metal chelating agent treatment 404 to form a liquid biomass stream 406, followed by passing the liquid biomass stream 406 through an anionic and cationic ion exchange treatment 408 to form a liquid biomass stream 410 containing cationic ion exchange material bound to metal and anionic ion exchange material bound to chlorine. The liquid biomass stream 410 is passed through a filter 412 to form a reduced-metal and reduced-chlorine liquid biomass stream 414.

FIG. 5 depicts an embodiment 500 comprising passing a metal- and chlorine-containing liquid biomass stream 502 through a cationic ion exchange treatment 504 to form a liquid biomass stream 506 containing cationic ion exchange material bound to metal, optionally followed by passing the liquid biomass stream 506 through a filter 508 to form a reduced-metal liquid biomass stream 510. The reduced-metal liquid biomass stream 510 is passed through an anionic ion exchange treatment 512 to form a reduced-metal, reduced-chlorine liquid biomass stream 514 containing anionic ion exchange material bound to chlorine, optionally followed by passing the liquid biomass stream 514 through a filter 516 to form a filtered reduced-metal and reduced-chlorine liquid biomass stream 518.

FIG. 6 depicts an embodiment 600 comprising passing a metal- and chlorine-containing liquid biomass stream 602 through a metal chelating agent treatment 604 to form a metal chelate-containing liquid biomass stream 606, followed by passing the liquid biomass stream 606 through a filter 608 to form a reduced-metal liquid biomass stream 610. The liquid biomass stream 610 is passed through an anionic ion exchange treatment 612 to form a liquid biomass stream 614 containing anionic ion exchange material bound to chlorine, optionally followed by passing the liquid biomass stream 614 through a filter 616 to form a reduced-metal and reduced-chorine liquid biomass stream 618.

FIG. 7 depicts an embodiment 700 comprising passing a metal-containing liquid biomass stream 702 through a metal chelating agent treatment 704 to form a metal chelate-containing liquid biomass stream 706, followed by passing the liquid biomass stream 706 through a filter 708 to form a liquid biomass stream 710. The liquid biomass stream 710 is passed through a cationic ion exchange treatment 712 to form a liquid biomass stream 714 containing cationic ion exchange material bound to metal, optionally followed by passing the liquid biomass stream 714 through a filter 716 to form a reduced-metal liquid biomass stream 718.

FIG. 8 depicts an embodiment 800 comprising passing a metal- and chlorine-containing liquid biomass stream 802 through a metal chelating agent treatment 804 to form a metal chelate-containing liquid biomass stream 806, followed by passing the liquid biomass stream 806 through a cationic ion exchange treatment 808 to a form liquid biomass stream 810 containing cationic ion exchange material bound to metal. The liquid biomass stream 810 is passed through a filter 812 to form a filtered liquid biomass stream 814. The filtered liquid biomass stream 814 is passed through an anionic ion exchange treatment 816 to form a liquid biomass stream 818 containing anionic ion exchange material bound to chlorine, and the liquid biomass stream 818 is optionally passed through a filter 820 to form a reduced-metal and reduced-chlorine liquid biomass stream 824.

FIG. 9 depicts an embodiment 900 comprising passing a metal- and chlorine-containing liquid biomass stream 902 through a metal chelating agent treatment 904 to form a metal chelate-containing liquid biomass stream 906, followed by passing the liquid biomass stream 906 through a filter 908 to form a filtered liquid biomass stream 910. The filtered liquid biomass stream 910 is passed to a cationic ion exchange treatment 912 to form a liquid biomass stream 914 containing cationic ion exchange material bound to metal. The liquid biomass stream 914 is optionally passed through a filter 916 and a resulting liquid biomass stream 918 is passed through an anionic ion exchange treatment 920 to form a liquid biomass stream 922 containing an anionic ion exchange material bound to chlorine, and the liquid biomass stream 922 the optionally passed through a filter 924 to form a reduced-metal and reduced-chlorine liquid biomass stream 926.

Certain embodiments may provide, for example, methods, processes, systems, or apparatus to obtain a low-contaminant liquid biomass stream from a pyrolysis stream, the pyrolysis stream having one or more of contaminants (for example one or more for example all of the contaminants discussed above), comprising: condensing a portion of the pyrolysis stream in the presence of one or more contaminant complexing agents (for example one or more for example all of the contaminant complexing agents discussed above) to form a liquid biomass condensate comprising one or more contaminant complexes; and separating the one or more contaminant complexes from the condensate to form the low-contaminant liquid biomass stream.

In certain embodiments, for example, the pyrolysis stream may comprise vapor. In certain further embodiments, for example, the vapor may be formed by rapid thermal pyrolysis of a cellulosic biomass. In certain embodiments, for example, the pyrolysis stream may comprise one or more aerosols. In certain embodiments, for example, the pyrolysis stream may comprise ash. In certain embodiments, for example, the ash may comprise one or more metals. In certain further embodiments, the one or more metals (for example antimony, arsenic, barium, beryllium, boron, cadmium, calcium, chromium, cobalt, copper, iron, lead, lithium, magnesium, manganese, mercury, molybdenum, nickel, phosphorous, potassium, sodium, selenium, silicon, silver, strontium, tin, titanium, vanadium, and zinc) may be partially soluble in the liquid biomass. In certain embodiments, for example, the pyrolysis stream may comprise char. In certain embodiments, for example, the pyrolysis stream may comprise inorganic heat transfer particles (for example sand). In certain embodiments, for example, one or more of the ash, char, and/or inorganic heat transfer particles may comprise antimony, arsenic, barium, beryllium, boron, cadmium, calcium, chromium, cobalt, copper, iron, lead, lithium, magnesium, manganese, mercury, molybdenum, nickel, phosphorous, potassium, sodium, selenium, silicon, silver, strontium, tin, titanium, vanadium, and zinc.

In certain embodiments, for example, the pyrolysis stream may be passed through a high efficiency cyclone prior to introduction to the condenser. In certain embodiments, for example, the condensing temperature may be below the plating temperature of each of the one or more contaminant complexing agents.

In certain embodiments, for example, prior to the separating, the liquid biomass condensate may be at a temperature of at least 30° C., for example at a temperature of at least 40° C., at least 45° C., at least 50° C., at least 60° C., at least 70° C., or at a separating temperature of at least 80° C. In certain further embodiments, for example, prior to the separating, the liquid biomass condensate may be at a temperature of 20-80° C., for example at a temperature in the range of 25-70° C., in the range of 25-50° C., in the range of 30-40° C., in the range of 40-80° C., in the range of 50-75° C., in the range of 60-75° C. or at a temperature in the range of 65-75° C. For example, in certain embodiments the temperature of the liquid biomass condensate may be in the range of 30-40° C.

In certain embodiments, for example, the pyrolysis stream may be condensed in a condensing chamber (or "condenser," for short), or in multiple condensing chambers (for example condensed in a primary condensing chamber and further condensed in a secondary condensing chamber). In certain further embodiments, for example, the pyrolysis stream may be rapidly cooled in a first condenser from a conversion temperature of approximately 350° C. to 600° C. to a temperature of less than 100° C. (for example 30-40° C.) in less than 1 second, for example to a temperature of less than 80° C. (for example less than 70° C. or less than 50° C.) in less than 100 ms, for example to a temperature of less than 80° C. in less than 20 ms.

In certain embodiments, for example, the pyrolysis stream may be upward flowing in the condensing chamber (or in one or more of multiple condensing chambers). In certain embodiments, for example, the pyrolysis stream (for example an upward flowing pyrolysis stream) may be rapidly cooled by a downward flowing quench stream, and at least a portion of the pyrolysis stream may be condensed to form condensed liquid biomass. In certain embodiments, for example, the mass ratio of the downward flowing quench stream to the condensed portion of the pyrolysis stream may be at least 50:1, for example at least 100:1, 150:1, 200:1, or the mass ratio of the quench stream to the condensed portion of the pyrolysis stream may be at least 300:1.

In certain embodiments, for example, the quench stream may comprise previously condensed liquid biomass. In certain embodiments, for example, the previously condensed liquid biomass may be contained in a lower portion of the condensing chamber (or in one or more out of multiple condensing chambers). In certain embodiments, for example, the pyrolysis stream may be introduced to the condensing chamber (for example the condensing chamber may be a primary or a secondary condensing chamber) at a position just above the top surface of the previously condensed liquid biomass. In certain embodiments, for example, the flow of the pyrolysis stream in the condensing chamber may be counter-current relative to the flow of the quench stream. In certain embodiments, for example, the flow of the pyrolysis stream in the condensing chamber may be concurrent relative to the flow of the quench stream. In certain embodiments, for example, at least a portion of the previously quenched liquid biomass may be pumped out of the condensing chamber and then pumped through a recirculation assembly comprising an external heat exchanger, whereby the portion of the previously quenched liquid biomass is cooled and recirculated to a liquid distributor, wherein the liquid distributor is positioned in an upper portion of the condensing chamber. In certain embodiments, for example, the previously condensed liquid biomass may have an average liquid residence time in the condensing chamber and the recirculation assembly, combined, of at least 5 minutes, at least 30 minutes, at least 60 minutes, or an average liquid residence time in the condensing chamber and the recirculation assembly, combined, of at least 2 hours (for example at least 4 hours or at least 8 hours).

In certain embodiments, for example, the quench stream may be at least partially atomized by the liquid distributor. In certain embodiments, for example, the atomized quench stream may coalesce in the condensing chamber (for example the condensing chamber may be a primary or a secondary condensing chamber) and settle by gravitational action in the lower portion of the condensing chamber. In certain embodiments, for example, the quench stream may flow downwardly out of the liquid distributor. In certain embodiments, for example, the downwardly flowing quench stream may form a portion of the previously condensed liquid biomass in the lower portion of the condensing chamber (for example the downward flowing quench stream may arrive in the lower portion of the condensing chamber by gravitational flow). In certain embodiments, for example, the quench stream may flow downwardly out of the liquid distributor at a rate of at least 10 gpm/sq. ft. (gallons per minute per square foot) of the horizontal cross-sectional area of the condensing camber, for example at a rate of at least 50 gpm/sq. ft., for example at a rate of at least 100 gpm/sq. ft.

In certain embodiments, for example, one or more contaminant complexing agents may be introduced into the condensing chamber (or into one or more of multiple condensing chambers, for example introduced into a first condensing chamber and/or introduced into a second condensing chamber). In certain embodiments, for example, the one or more contaminant complexing agents may be introduced into a previously condensed liquid biomass in a lower portion of the condensing chamber (or into one or more previously condensed liquid biomasses present in one or more of multiple condensing chambers). In certain embodiments, for example, the one or more contaminant complexing agents may be introduced into the quench stream.

In certain embodiments, for example, the quench stream may comprise one or more of a pyrolysis stream condensate (for example a pyrolysis vapor condensate) or portion thereof, water, diesel, petroleum based liquid, and polysorbate. Other quench streams are contemplated herein.

In certain embodiments, for example, the liquid distributor may include, but not be limited to: a vane, a pipe, a chimney, a finger distributor, a spray head, a nozzle, a trays, and packing.

In certain embodiments, a first pyrolysis stream condensing chamber may be in fluid communication with a second condensing chamber. In certain embodiments, for example, a first overhead stream may be passed from the first condensing chamber to the second condensing chamber. In certain embodiments, for example, the first overhead stream may comprise an uncondensed portion of a pyrolysis stream. In certain embodiments, for example, the first overhead stream may comprise entrained droplets (for example a mist) of condensed liquid biomass. In certain embodiments, for example, the pyrolysis stream may comprise one or more contaminants, and the first overhead stream may have a reduced concentration of at least one of the one or more contaminants prior to introduction to the second condenser, for example the concentration of at least one of the one or more contaminants may be reduced by at least 50% relative to the pyrolysis stream, for example by at least 75%, or the concentration of at least one of the one or more contaminants may be reduced by at least 90% relative to the pyrolysis stream.

In certain embodiments, for example, the first overhead stream may exit an outlet of the first condensing chamber and enter the second condensing chamber through an inlet of the second condensing chamber. In certain embodiments, for example, the introduced first overhead stream may be upward flowing in the second condensing chamber. In certain embodiments, for example, the introduced first overhead stream (for example an upward flowing stream) may be rapidly cooled or heated in the second condensing chamber by a downward flowing second quench stream (herein and throughout the "second quench stream" refers to a quench stream in the second condensing chamber, irregardless of whether or not any quench stream is present in any first condensing chamber). In certain embodiments, for example, the mass ratio of the second quench stream to a condensed portion of the introduced first overhead stream may be at least 50:1, for example at least 100:1, 150:1, 200:1, or the mass ratio of the second quench stream to the condensed portion of the introduced first overhead stream may be at least 300:1.

In certain embodiments, for example, the second quench stream may comprise part or all of a liquid biomass previously condensed in the second condensing chamber (the "second previously condensed liquid biomass"). In certain embodiments, for example, the part or all of the second previously condensed liquid biomass may be contained in a lower portion of the second condensing chamber. In certain embodiments, for example, the introduced first overhead stream may be introduced to the second condensing chamber at a position just above the top surface of the part or all of the second previously condensed liquid biomass.

In certain embodiments, for example, the flow of the introduced first overhead stream in the second condensing chamber may be counter-current relative to the flow of the second quench stream. In certain embodiments, for example, the flow of the introduced first overhead stream in the second condensing chamber may be concurrent relative to the flow of the second quench stream. In certain embodiments, for example, at least a portion of the second previously condensed liquid biomass may be pumped out of the second condensing chamber and then pumped through a recirculation assembly comprising an external heat exchanger, whereby the at least a portion of the second previously condensed liquid biomass is cooled and recirculated to a liquid distributor in the second condensing chamber (the "second liquid distributor"). In certain embodiments, for example, the second liquid distributor may be positioned in an upper portion of the second condensing chamber. In certain embodiments, for example, the second previously condensed liquid biomass may have an average liquid residence time in the second condensing chamber and the recirculation assembly, combined, of at least 5 minutes, at least 30 minutes, at least 60 minutes, or an average liquid residence time in the second condensing chamber and the recirculation assembly, combined, of at least 2 hours (for example at least 4 hours or at least 8 hours).

In certain embodiments, for example, the second quench stream may be at least partially atomized by the second liquid distributor. In certain embodiments, for example, the at least partially atomized second quench stream may coalesce in the condensing column and may settle by gravitational action in a lower portion of the second condensing chamber. In certain embodiments, for example, the second quench stream may flow downwardly out of the second liquid distributor. In certain embodiments, for example, the downwardly flowing second quench stream may form a portion of the liquid biomass previously condensed in the second condensing chamber in the lower portion of the second condensing (for example by gravitational flow). In certain embodiments, for example, the second quench stream may flow downwardly out of the liquid distributor at a rate of at least 10 gpm/sq. ft. (gallons per minute per square foot) of the horizontal cross-sectional area of the second condensing chamber, for example at a rate of at least 50 gpm/sq. ft., for example at a rate of at least 100 gpm/sq. ft.

In certain embodiments, for example, a portion of the first overhead stream introduced to the second condensing chamber may exit the second condensing chamber as a second overhead stream. In certain embodiments, for example, the second overhead stream may comprise an uncondensed portion of the first overhead stream. In certain embodiments, for example, the second overhead stream may comprise entrained droplets (for example a mist) of condensed liquid biomass.

In certain embodiments, for example, at least a portion of a first overhead stream (for example an overhead stream exiting a first condenser) may be passed to a demister system. In certain embodiments, for example embodiments that are exclusive of any second condenser, all of the first overhead stream may be passed to a demister system. In certain embodiments, for example embodiments comprising a second condenser, at least a portion of a second overhead stream (for example an overhead stream exiting a second condenser) may be passed to a demister system. In certain embodiments, for example, the demister may be incorporated into (or integral to) the second condenser. In certain further embodiments, for example, the demister system may comprise a system wherein liquid and/or solid particles are captured by inertial impaction and/or adherence to structures (for example fibers) by Van Der Waals forces or other electrostatic or electrodynamic forces. In certain further embodiments, for example, captured particles combine to form droplets. In certain embodiments, for example, captured particles are accumulated in a vessel by gravitational sedimentation.

In certain embodiments, for example, the demister system may comprise a series of mist eliminator units. In certain further embodiments, for example, a first unit of the series of mist eliminator units may comprise a vane mist eliminator. In certain further embodiments, for example, the vane mist eliminator may remove about 99% of the mist as low as 10 microns. In certain further embodiments, for example, a second unit of the series of mist eliminator units may comprise a stainless steel wire mesh pad having a density of about 5 lbs/cu. ft. (pounds per cubic foot) and a wire diameter of 0.011 inches and a surface area of 45 ft. sq./ft. cu. (square foot per cubic foot) and 99.0% voids. In certain embodiments, for example, the second unit may comprise one or more of glass, alloy 20, Teflon, polypropylene, and the like. In certain embodiments, for example, a third unit of the demister system may comprise 9 lb/cu. ft. (pounds per cubmit stainless steel wire mesh pad, 0.011 inch diameter and a surface area of 85 sq. ft./cu. ft., and 98.0% voids. In certain embodiments, for example, the demister system may comprise co-knit style comprising a metal wire construction with fiberglass. The pad is 9 lb/cu. ft. with a wire diameter of 0.00036 inches and a surface area of 3725 sq. ft./cu. ft., and 99.0% voids.

In certain embodiments, for example, a portion of an overhead stream from a condenser, or portions of overhead streams from multiple condensers (for example a portion of a first overhead stream from a first condensing chamber and a a portion of a second overhead stream from a second condensing chamber), or a product stream from a demister, may be further passed through a fiber bed system. In certain embodiments, for example, fine particles (for example droplets or aerosols of less than approximately 3 microns), particles greater than 3 microns that may pass though the demister system may be passed to the fiber bed system and thereby separated from a stream. In certain embodiments, for example, the fiber bed system may comprise two or more fiber beds. In certain further embodiments, for example, two fiber beds may be arranged in a parallel configuration. In certain embodiments, for example, a first fiber bed may remain on-line for a period of about 8-24 hours (for example 10-12 hours) followed by a service cycle, draining cycle, or cleaning cycle, and a second fiber bed may be activated during the service cycle, draining cycle, or cleaning cycle of the first fiber bed. In certain embodiments, for example, a first fiber bed and a second fiber bed may be operated in alternating on-line and draining cycles. In certain embodiments, for example, the fiber bed system may capture particles present in a vapor stream that are larger than about 3 microns by inertial impaction. In certain embodiments, for example, particles between 1 and 3 microns present in a vapor stream may be captured through interception in which the particles come within about one particle radius of the surface of a fiber of the fiber bed system. In certain embodiments, for example, particles of less than 1 micron present in a vapor stream may be captured through diffusion or Brownian movement. In certain embodiments, for example, captured particles may join together to form larger liquid droplets. In certain embodiments, for example, the fiber bed system may comprise two or more filters in series, for example to limit the pressure drop across each of the filters in series. In certain embodiments, for example, a fiber bed unit may be operated or may remain on-line until the pressure drop across the filter unit reaches a predetermined limit. In certain embodiments, for example, the fiber bed may be operated so that the pressure drop across a filter element does not exceed one or more predetermined limits (for example the fiber bed may be operated so that the pressure drop across a filter element does not exceed 100 inches of water).

In certain embodiments, for example, mist and/or aerosol liquid collected in the fiber bed system may be relatively viscous at ambient conditions. In certain embodiments, for example, a reheater heat exchanger may be employed between one or more of a condenser, a demister, and the fiber bed system (for example a reheater heat exchanger may be employed between a first or second condensing chamber and the fiber bed system, or between a demister and the fiber bed system. In certain embodiments, for example, a demister may be incorporated in a first or second condenser and the reheater heat exchanger may be installed upstream of the fiber bed system. In certain further embodiments, for example, the reheat exchanger may be used to increase the temperature of the vapor stream (for example up to 60-65° C.) to reduce the viscosity of liquids captured in the fiber bed system, whereby drainage of the liquids from the fiber bed system may be improved.

FIG. 10 depicts a process 1000 for reducing metal and chlorine contaminants in a pyrolysis stream 1002. The pyrolysis stream 1002 and a metal chelating agent 1004 are introduced into a condenser 1006 mated with an external cooling loop (whereby a condensed pyrolysis oil 1008 is pumped out of the condenser 1006 by a pump 1012 to form a stream 1010, and a portion 1014 of the stream 1010 is cooled by a heat exchanger 1016) in fluid communication with a quench inlet distributor 1018 which is positioned in the condenser 1006. The pyrolysis stream 1002 is contacted with a downward flowing recirculated condensate 1020 to form a solid complex-containing condensate having a pH of at least 2, and at a weight ratio of 1:100, relative to the stream 1020. A portion 1022 of the solid complex-containing condensate stream 1010 is passed through an external filter assembly 1024 (comprising a 3-way plug valve 1026 and alternate filters 1028A and 1028B) configured to collect at least a portion of the solid complex. A filtered condensate 1030 is mixed with cationic ion exchange particles 1032 and anionic ion exchange particles 1034 in a mixed process vessel 1036. The contents 1038 of the mixed process vessel 1030 are removed by a pump 1042 to form a stream 1040, which is partially recirculated to the process vessel 1036 through a temperature control heat exchanger 1046. The non-recirculated portion 1048 of the stream 1040 is passed through a second filter assembly 1050 to form a product liquid biomass stream 1052.

Certain embodiments may provide, for example, a method, comprising: passing a pyrolysis stream through a multi-condenser separation train to form at least a first liquid biomass stream and a second liquid biomass stream; reducing the concentration of one or more contaminants present in the first liquid biomass stream by contacting the first liquid biomass stream with one or more decontamination agents; combining the first liquid biomass stream and the second liquid biomass stream to form a product stream, wherein each of the first liquid biomass stream and the product stream has a pH of at least 2; and adjusting the temperature of a first condenser of the multi-condenser separation train to control the concentration of the one or more contaminants in the product stream. In certain embodiments, for example, the second liquid biomass stream may not undergo any contaminant reduction steps prior to combining with the first liquid biomass stream. In certain embodiments, for example, the first liquid biomass stream may have a lower concentration of the one or more contaminants (for example, a total concentration of alkali and alkaline earth metals combined) relative to the second liquid biomass stream. In certain embodiments, for example, the temperature of the first condenser may be reduced to increase the portion of the pyrolysis stream condensed in the first condenser, thereby increasing the ratio of the first liquid biomass stream to the second liquid biomass stream. In certain embodiments, for example, the ratio of the first liquid biomass stream relative to the second liquid biomass stream, on a weight basis, may be at least 0.05:1, for example at least 0.1:1, at least 0.3:1, at least 0.5:1, at least 1:1, at least 1.5:1, at least 2:1, at least 2.5:1, at least 3:1, at least 4:1, at least 5:1, at least 7:1, at least 10:1, or the ratio of the first bottom stream relative to the second bottom stream may be at least 20:1 on a weight basis. In certain embodiments, for example, the temperature of the first condenser may be set to below 50° C. (for example to below 40° C. or to below 35° C.) and the ratio of the first liquid biomass stream relative to the second liquid biomass stream, on a weight basis, may be at least at least 1:1, at least 1.5:1, at least 2:1, at least 2.5:1, at least 3:1, at least 4:1, at least 5:1, at least 7:1, at least 10:1, or the ratio of the first bottom stream relative to the second bottom stream may be at least 20:1 on a weight basis. In certain embodiments, for example, the temperature of the first condenser may be set in a range of 30-40° C. and the ratio of the first liquid biomass stream relative to the second liquid biomass stream, on a weight basis, may be in the range of 1.5:1-4:1. In certain embodiments, for example, the ratio of concentrations of the one or more contaminants present in the first liquid biomass stream relative to the second liquid biomass stream may be less than 1:1, less than 0.75:1, less than 0.5:1, less than 0.25:1, less than 0.1:1, less than 0.05:1, or the ratio of concentrations of the one or more contaminants present in the first liquid biomass stream relative to the second liquid biomass stream may be less than less than 0.01:1. In certain embodiments, for example, the temperature of the first condenser may be set in a range of 30-40° C. and the ratio of concentrations of the one or more contaminants present in the first liquid biomass stream relative to the second liquid biomass stream may in the range of 0.01:1-0.1:1. In certain embodiments, for example, the temperature of the first condenser may be set in a range of 30-40° C., the ratio of concentrations of the one or more contaminants present in the first liquid biomass stream relative to the second liquid biomass stream may in the range of 0.01:1-0.1:1, and the ratio of the first liquid biomass stream and the second liquid biomass stream, on a weight basis, may be in the range of 1.5:1-4:1.

Certain embodiments may provide, for example, methods, processes, systems, or apparatus, comprising: in a first condenser (for example one of the foregoing described condensers), contacting a pyrolysis stream containing one of the foregoing described contaminants with one of the foregoing described contaminant complexing agents to form a reduced-contaminant overhead stream and a contaminant complex-containing first bottom stream; in a second condenser, condensing a portion of the reduced-contaminant overhead stream to form a further overhead stream and a second bottom stream; and removing at least a portion of the contaminant complex from the first bottom stream.

In certain embodiments, for example, the first bottom stream and the second bottom stream may be combined. In certain further embodiments, for example, the ratio of the first bottom stream relative to the second bottom stream, on a weight basis, may be at least 0.05:1, for example at least 0.1:1, at least 0.3:1, at least 0.5:1, at least 1:1, at least 1.5:1, at least 2:1, at least 2.5:1, at least 3:1, at least 4:1, at least 5:1, at least 7:1, at least 10:1, or the ratio of the first bottom stream and the second bottom stream may be at least 20:1 on a weight basis.

In certain embodiments, for example, the average liquid residence time of the first condenser may be at least 5 minutes, at least 30 minutes, at least 60 minutes, at least 2 hours, for example at least 2.5 hours, 3 hours, or the average liquid residence time of the first condenser may be at least 4 hours. In certain embodiments, for example, the average liquid residence time may be less than 2 hours, for example the average liquid residence time may be less than 1.5 hours, less than 1 hours, less than 30 minutes, or the average liquid residence time may be less than 5 minutes. In certain embodiments, for example, the average liquid residence time may be in the range of 1-4 hours, for example, the average liquid residence time may be in the range of 1-3 hours, in the range of 1.5-2.5 hours, in the range of 2-3 hours, or the average liquid residence time may be in the range of 3-4 hours.

In certain embodiments, for example, the reduced-contaminant overhead stream may comprise entrained droplets of condensed pyrolysis vapors (for example mist). In certain embodiments, for example, the temperature of the second condenser may be greater than the temperature of the first condenser.

In certain embodiments, for example, the methods, processes, systems, or apparatus may further comprise passing the further overhead stream through a demister and optionally one or more fiber beds. In certain embodiments, for example, the methods, processes, systems, or apparatus may further comprise forming a combustible carrier gas from the further overhead stream. In certain embodiments, for example, the first and second bottom streams, and optionally a stream obtained from the optional demister and/or fiber bed are collected in a storage tank, the storage tank coupled with an external recirculation loop comprising a filter and optionally a heater.

Figure 11:
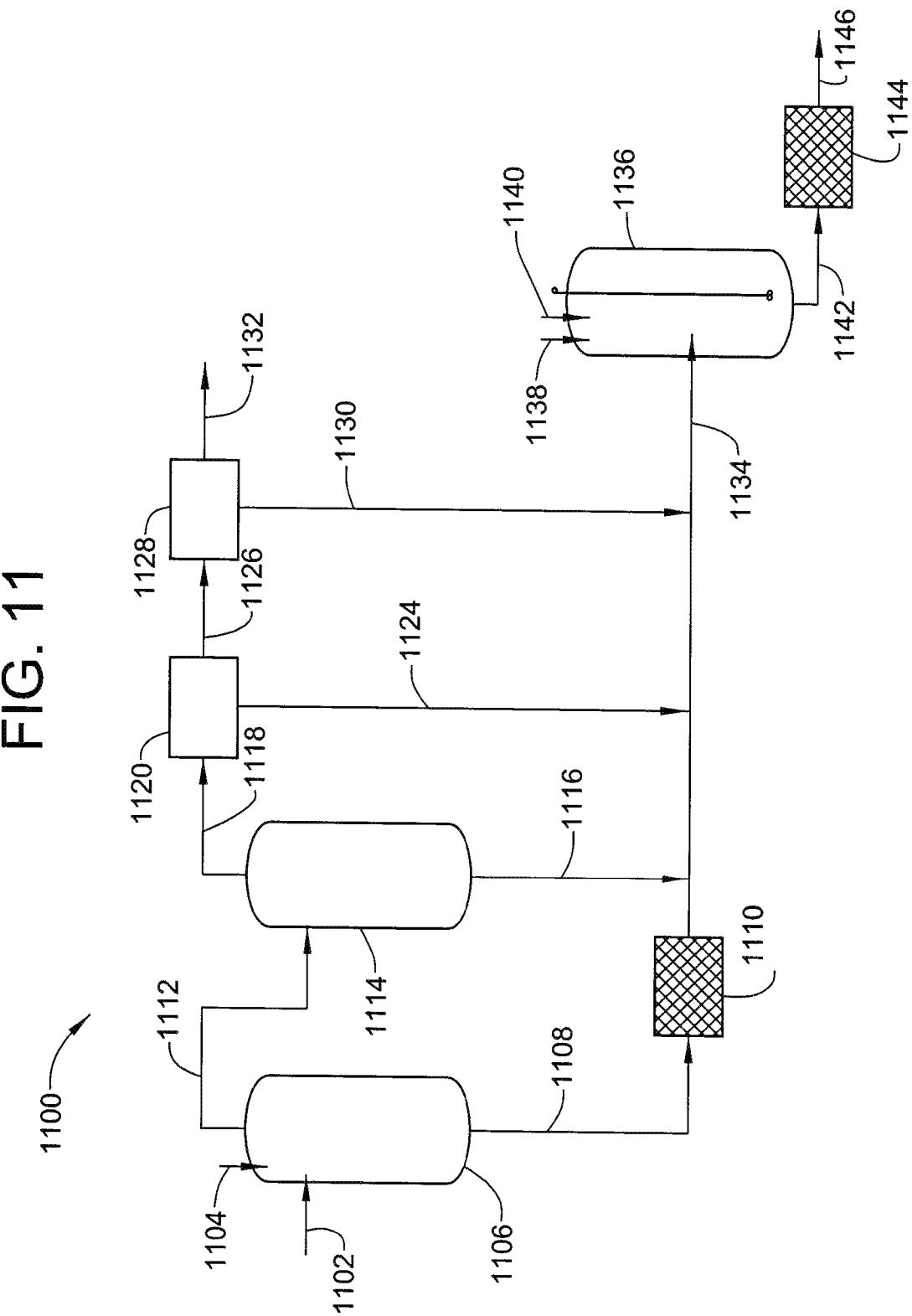
FIG. 11 is a schematic depiction of a process incorporating a demister and a filter bed for removing contaminants from a pyrolysis stream.

FIG. 11 depicts a process 1100 for reducing metal and chlorine contaminants in a pyrolysis stream. A first pyrolysis stream 1102 and an optional metal chelating agent stream 1104 are introduced to a first condenser 1106, and the pyrolysis stream 1102 is partially condensed to form a first liquid biomass stream 1108 and a reduced-contaminant second pyrolysis stream 1112. If the optional metal chelating stream 1104 is present, then the first liquid biomass stream 1108 is a solid complex-containing first liquid biomass stream. The reduced-contaminant second pyrolysis stream 1112 is partially condensed in a second condenser 1114 to form a second liquid biomass stream 1116 and a third pyrolysis stream 1118. The third pyrolysis stream 1118 is passed through a demister 1120 to form a liquid biomass stream 1124 and a fourth pyrolysis stream 1126, and the fourth pyrolysis stream 1126 is passed through a filter bed 1128 to obtain a combustible gas 1132 and an additional liquid biomass stream 1130. The first liquid biomass stream 1108 is filtered by a filter assembly 1110 and combined with the other liquid biomass streams (1116, 1124, and 1130) to form a combined stream 1134. The combined stream 1134 is mixed with cationic ion exchange particles (and optionally chelating agent) 1138 and anionic exchange particles 1140 in a process vessel 1136 and the mixed stream 1142 removed from the process vessel 1136 and passed through a filter 1144 to form a product stream 1146.

Certain embodiments may provide, for example, methods, processes, systems, or apparatus to obtain a low-contaminant liquid biomass stream from a contaminant-containing pyrolysis stream, comprising: contacting the pyrolysis stream with a quench stream (for example one of the foregoing described quench streams) and a contaminant complexing agent (for example one of the foregoing described complexing agents) in a condenser (for example one of the foregoing described condensers) to form solid complex-containing condensate; and filtering the solid complex from the condensate.

In certain embodiments, for example, the pyrolysis stream may have a volume ratio of condensable to non-condensable gases at a temperature of 40° C. and a pressure of 1 atmosphere in the range of 1:1-0.5:1. In certain embodiments, for example, the non-condensable gases may have an average residence time in the range of 1-3 seconds in the condenser.

In certain embodiments, for example, the filtering may comprises passing the condensate through a cake comprising ground biomass. In certain further embodiments, for example, the cake may be positioned upstream of, held in position by, or rest on a membrane filter. In certain embodiments, for example, the ground biomass may comprise particles having an average size in the range of 0.5-5 mm, for example in the range of 0.5-3 mm. In certain embodiments, for example, the cake may be applied as a pre-coat to a filter, or a membrane filter may be pre-coated with the cake of ground biomass. In certain embodiments, for example, the cake comprising ground biomass may be periodically removed and combusted in a reheater of a rapid thermal processing unit. In certain embodiments, for example, the cake comprising ground biomass may be periodically removed and combusted to generate process heat. In certain further embodiments, for example, the generated process heat may be used to dry a biomass.

In certain embodiments, for example, the contaminant-containing pyrolysis stream may comprise metal-containing ash. In certain further embodiments, for example, one or more metals and/or metal compounds present in the metal-containing ash may dissolve into the condensate. In certain embodiments, for example, the contaminant complexing agent may complex at least one of the one or more dissolved metals and/or metal compounds. In certain embodiments, for example, the quench may comprise a portion of the solid complex-containing condensate. In certain embodiments, for example, the quench may comprise a portion of the filtered condensate. In certain embodiments, for example, the quench may be introduced into an upper portion of the condenser through a liquid distributor. In certain embodiments, for example, at least a portion of the quench may be atomized in the condenser. In certain embodiments for example, the quench may be downward flowing.

Certain embodiments may provide, for example, methods, processes, systems, or apparatus to obtain a low-contaminant liquid biomass stream from a solids-containing pyrolysis stream, comprising: condensing a portion of the solids-containing pyrolysis stream to form a condensate containing suspended solids (for example one or more of the foregoing described suspended solids); dissolving contaminants (for example one or more of the foregoing described contaminants) present in the suspended solids into the condensate; and contacting the condensate with a contaminant complexing agent (for example one of the foregoing described contaminant complexing agents) to form solid complex-containing condensate.

In certain embodiments, for example, the solids-containing pyrolysis stream may comprise pyrolysis vapors and solid particles. In certain embodiments, for example, the solids may comprise ash, char, heat transfer medium, catalyst particles, catalytically active particles, and/or fines. In certain embodiments, for example, the condensate may contain 0.05-1 wt. % of solid particles, for example 0.1-0.5 wt. % of the solid particles. In certain embodiments, for example, the condensate may contain less than 0.15 wt. % of the solid particles, for example less than 0.10 wt. %, or less than 0.05 wt. % of the solid particles. In certain embodiments, for example, the contaminants may comprise metals, metal counterions, and/or metal oxides (for example metal oxides present in solid ash particles present in the condensate). In certain embodiments, for example, the condensate may comprise a liquid. In certain embodiments, for example, an agent may be added to the condensate to promote the dissolving. In certain embodiments, for example, an agent may be added to the condensate to inhibit the dissolving.

In certain embodiments, for example, less than 50 wt. % of the contaminants present in the suspended solids may dissolve into the condensate, for example less than 25 wt. %, less than 10 wt. %, less than 5 wt. %, or less than 1 wt. % of the contaminants present in the suspended solids may dissolve into the condensate. In certain embodiments, for example, at least 50 wt. % of the contaminants present in the suspended solids may dissolve into the condensate, for example at least 75 wt. %, at least 90 wt. %, at least 95 wt. %, or at least 99 wt. % of the contaminants present in the suspended solids may dissolve into the condensate.

In certain embodiments, for example, the methods, processes, systems, or apparatus may further comprise removing the condensate from the condenser and separating (for example filtering) a portion of the solid complex and the solids from the condensate to form the quench stream.

Certain embodiments may provide, for example, methods, processes, systems, or apparatus to remove one or more contaminants (for example one or more of the foregoing disclosed contaminants) present in a pyrolysis stream, comprising: condensing a portion of the pyrolysis stream in the presence of one or more complexing agents (for example one or more solid-state complexing agents, or one or more complexing agents present in a carrier (such as one or more complexing agents mixed with, mixed into, or pre-mixed with a liquid biomass), inclusive of any one or more of the foregoing disclosed complexing agents) to form a slurry, the slurry comprising: a) a liquid biomass; and b) the one or more solid-state complexing agents optionally bound to at least one of the one or more contaminants; and ii) removing a portion of the one or more complexing agents from the slurry to form a substantially complexing agent-free liquid biomass stream.

In certain embodiments, for example, the one or more complexing agents may weigh at least 0.25 wt. % relatively to the weight of the liquid biomass, for example at least 0.5 wt. %, at least 1.0 wt. %. In certain embodiments, for example, the one or more solid state complexing agents may weigh in the range of 25-0.75 wt. % relative to the weight of the liquid biomass.

In certain embodiments, for example, the pyrolysis stream may be rapidly condensed with a quench stream. In certain embodiments, for example, the quench stream may be formed from a portion of the slurry. In certain embodiments, for example, the slurry may have an average residence time of at least 5 minutes, for example at least 30 minutes, at least 60 minutes, at least 2 hours at least 2.5 hours, at least 3 hours, or the slurry may have an average residence time of at least 4 hours in the primary condenser assembly.

In certain embodiments, for example, a portion of the slurry may be recirculated in the primary condenser assembly, comprising passing the portion of the slurry through a heat exchanger. In certain embodiments, for example, the primary condenser assembly may comprise a slurry pump. In certain embodiments, for example, the primary condenser assembly may comprise a vessel equipped with an impeller mixer and cooling tubes.

EXAMPLES

Example 1

A renewable fuel oil was treated with varying loadings of anionic ion exchange resin and then filtered to remove chlorine. Results are shown in Table 3.

Example 2

Two renewable fuel oils (a low-ash sample and a high-ash sample) were treated with cationic ion exchange resin and/or oxalic acid and then filtered to remove ash. Results are shown in Table 4.

Example 3

A low-ash renewable fuel oil was treated with cationic ion exchange resin and/or oxalic acid and filtered. The reduction in specific metals results are shown in Table 5.

Example 4

A high-ash renewable fuel oil was treated with cationic ion exchange resin and/or oxalic acid and filtered. The reduction in specific metals results are shown in Table 6.

TABLE 3

Reduction in Chlorine Content (in PPM) of a Liquid Biomass After Treatment with Varying Loadings of Anionic Ion Exchange Resin.

| Wt. % Anionic Ion Exchange Resin Added | Chlorine Following Treatment, ppm | % Chlorine Removed |
| --- | --- | --- |
| Untreated | 628 | Unfiltered |
| 1% | 309 | 52 |
| 2% | 188 | 71 |
| 4% | 125 | 80 |
| 8% | 100 | 84 |

TABLE 4

Reduction in Ash (wt. %) in both Low-Ash and High-Ash Liquid Biomasses After Treatment with Cationic Ion Exchange Resin (IE) and/or Oxalic Acid (OA)

| | Low-Ash (0.12 wt. %) Renewable Fuel Oil | | | High-Ash (0.58 wt. %) Renewable Fuel Oil | | |
|---|---|---|---|---|---|---|
| Treatment | Wt. % IE Added | Wt. % OA Added | % Ash Reduction | Wt. % IE Added | Wt. % OA Added | % Ash Reduction |
| IE (only) | 1.42 | — | 83.3 | 7.47 | — | 93.1 |
| OA (only) | — | 0.16 | 50.0 | — | 0.83 | 55.2 |
| IE followed by OA | 0.77 | 0.16 | 75.0 | 2.14 | 0.83 | 81.0 |
| OA followed by IE | 0.77 | 0.16 | 75.0 | 0.83 | 2.14 | 63.8 |

TABLE 5

Reduction in Metal Content (in PPM) of Low-Ash Liquid Biomass After Treatment with Cationic Ion Exchange Resin (IE) and/or Oxalic Acid (OA)
Low-Ash (0.12 wt. %) Renewable Fuel Oil

| Metal | Untreated | After Treatment with 0.16 wt. % OA | After Treatment with 1.42 wt. % IE | After Treatment with 0.16 wt. % OA Followed By 0.77 wt. % IE |
|---|---|---|---|---|
| Calcium | 196.6 | 73.8 | 15.3 | 18.8 |
| Magnesium | 54.7 | 8.8 | 1.7 | 1.1 |
| Potassium | 20.5 | <0.1 | <0.1 | <0.1 |
| Sodium | 32.9 | 34.1 | 19.1 | 3.6 |
| Aluminium | 2.7 | 4.6 | <0.1 | <0.1 |
| Antimony | <0.1 | <0.1 | <0.1 | <0.1 |
| Arsenic | <0.1 | <0.1 | <0.1 | <0.1 |
| Barium | <0.1 | <0.1 | <0.1 | <0.1 |
| Beryllium | <0.1 | <0.1 | <0.1 | <0.1 |
| Boron | 2.4 | 1.3 | <0.1 | <0.1 |
| Cadmium | <0.1 | <0.1 | <0.1 | <0.1 |
| Chromium | <0.1 | <0.1 | <0.1 | <0.1 |
| Cobalt | <0.1 | <0.1 | <0.1 | <0.1 |
| Copper | 1.9 | 1.3 | 1.5 | 0.9 |
| Iron | 26.7 | 6.2 | 7.5 | 3.4 |
| Lead | <0.1 | <0.1 | <0.1 | <0.1 |
| Lithium | <0.1 | <0.1 | <0.1 | <0.1 |
| Manganese | 24.1 | 2.9 | 0.6 | <0.1 |
| Mercury | <0.1 | <0.1 | <0.1 | <0.1 |
| Molybdenum | <0.1 | <0.1 | <0.1 | <0.1 |
| Nickel | <0.1 | 1.8 | <0.1 | <0.1 |
| Phosphorous | 7.9 | 9.7 | 10 | 3.3 |
| Selenium | <0.1 | <0.1 | <0.1 | <0.1 |
| Silicon | 4.4 | 4.1 | <0.1 | 0.7 |
| Silver | <0.1 | <0.1 | <0.1 | <0.1 |
| Strontium | 1.1 | 0.4 | <0.1 | <0.1 |
| Tin | <0.1 | <0.1 | <0.1 | <0.1 |
| Titanium | <0.1 | 15.9 | 1.5 | <0.1 |
| Vanadium | <0.1 | <0.1 | <0.1 | <0.1 |
| Zinc | 3.8 | 1.8 | 1.5 | 1.5 |
| TOTAL (ppm) | 379.7 | 166.7 | 58.7 | 33.3 |
| TOTAL Percent Reduction | — | 56% | 85% | 91% |

TABLE 6

Reduction in Metal Content (in PPM) of High-Ash Liquid Biomass After Treatment with Cationic Ion Exchange Resin (IE) and/or Oxalic Acid (OA)
High-Ash (0.58 wt. %) Renewable Fuel Oil

| Metal | Untreated | After Treatment with 0.83 wt. % OA | After Treatment with 7.47 wt. % IE | After Treatment with 0.83 wt. % OA Followed By 2.14 wt. % IE |
|---|---|---|---|---|
| Calcium | 1423.5 | 114.8 | 30.7 | 124.2 |
| Magnesium | 295.0 | 15.7 | 1.3 | 1.3 |
| Potassium | 139.9 | 325.6 | <0.1 | 1.1 |
| Silver | <0.1 | <0.1 | <0.1 | <0.1 |
| Aluminium | 78.3 | 81.7 | 5.6 | 37.3 |
| Arsenic | <0.1 | <0.1 | <0.1 | <0.1 |
| Boron | 5.8 | 3.5 | 2.0 | 2.6 |
| Barium | 3.1 | 0.4 | 0.4 | 0.4 |
| Beryllium | <0.1 | <0.1 | <0.1 | <0.1 |
| Cadmium | <0.1 | <0.1 | <0.1 | <0.1 |
| Cobalt | <0.1 | <0.1 | <0.1 | <0.1 |
| Chromium | <0.1 | <0.1 | <0.1 | <0.1 |
| Copper | 1.7 | 2.2 | 1.1 | 1.6 |
| Iron | 197.4 | 79.1 | 17.7 | 21.0 |
| Mercury | <0.1 | <0.1 | <0.1 | <0.1 |
| Lithium | <0.1 | <0.1 | <0.1 | <0.1 |
| Manganese | 81.6 | 6.5 | <0.1 | 2.8 |
| Molybdenum | <0.1 | <0.1 | <0.1 | <0.1 |
| Sodium | 94.5 | 50.2 | 37.7 | 16.4 |
| Nickel | 1.6 | <0.1 | <0.1 | <0.1 |
| Phosphorous | 72.1 | 65.2 | 48.5 | 32.0 |
| Lead | <0.1 | <0.1 | <0.1 | <0.1 |
| Antimony | <0.1 | <0.1 | <0.1 | <0.1 |
| Selenium | <0.1 | <0.1 | <0.1 | <0.1 |
| Silicon | 18.7 | 10.3 | 2.6 | 6.2 |
| Tin | <0.1 | <0.1 | <0.1 | <0.1 |
| Strontium | 6.9 | <0.1 | <0.1 | <0.1 |
| Titanium | <0.1 | 1.3 | <0.1 | 1.0 |
| Vanadium | <0.1 | <0.1 | <0.1 | <0.1 |
| Zinc | 15.4 | 1.7 | 1.3 | 1.6 |
| TOTAL (ppm) | 2435.5 | 758.2 | 148.9 | 249.5 |
| TOTAL Percent Reduction | — | 69% | 94% | 90% |

All publications and patent applications mentioned in this specification are herein incorporated by reference in their entirety (to the same extent as if each individual publication or patent application was specifically and individually incorporated within this document).

While preferred embodiments of the present invention have been shown and described herein, it will be obvious to those skilled in the art that such embodiments are provided by way of example only. It is intended that the following claims define the scope of the invention and that methods and structures within the scope of these claims and their equivalents be covered thereby.

What is claimed is:

1. A system to obtain a reduced-contaminant liquid biomass stream from a metal-containing and chlorine-containing pyrolysis stream, comprising:
   i) a pyrolysis reactor;

ii) at least one pyrolysis vapor condenser comprising at least one metal reduction unit;

iii) at least one chlorine reduction unit; and iv) at least one filter configured to filter at least one pyrolysis liquid stream wherein a first condenser of the at least one pyrolysis vapor condenser is sized to provide a liquid residence time of at least two hours.

2. The system of claim 1, wherein the first condenser is configured to provide a pyrolysis liquid condensate having an oxalic acid concentration of between 0.1 wt. % and 0.4 wt. % oxalic acid.

3. The system of claim 1, wherein the first condenser is configured to condense a portion of a pyrolysis vapor stream with a quench stream.

4. The system of claim 3, wherein the quench stream comprises recirculated condensed pyrolysis liquid.

5. The system of claim 3, wherein a first metal reduction unit of the at least one metal reduction unit is configured to introduce a metal complexing agent into the quench stream.

6. The system of claim 1, wherein a first chlorine reduction unit of the at least one chlorine reduction unit is positioned downstream of a first metal reduction unit of the at least one metal reduction unit.

7. The system of claim 6, wherein the first chlorine reduction unit is configured to contact a first pyrolysis liquid stream of the at least one pyrolysis liquid stream with anionic ion exchange particles.

8. The system of claim 6, wherein a first filter of the at least one filter is positioned between the first metal reduction unit and the first chlorine reduction unit.

9. The system of claim 1, wherein a further metal reduction unit different from the at least one metal reduction unit is positioned downstream of the at least one pyrolysis vapor condenser.

10. The system of claim 9, wherein the further metal reduction unit is configured to contact the at least one pyrolysis liquid stream with cationic ion exchange particles.

11. The system of claim 1, wherein the at least one pyrolysis vapor condenser further comprises a first chlorine reduction unit of the at least one chlorine reduction unit.

12. A system to obtain a reduced-contaminant liquid biomass stream from a pyrolysis stream, comprising:
i) a pyrolysis reactor;
ii) at least one pyrolysis vapor condenser;
iii) at least one contaminant reduction component having a liquid residence time of at least 2 hours; and
iv) at least one filter configured to filter at least one pyrolysis liquid stream.

13. The system of claim 12, wherein the at least one contaminant reduction component is configured to contact a pyrolysis condensate with oxalic acid at a concentration of between 0.1 wt. % and 0.4 wt. % oxalic acid.

14. The system of claim 13, wherein the at least one contaminant reduction component is configured to contact the pyrolysis condensate with anionic ion exchange particles.

15. An apparatus to obtain a reduced-contaminant liquid biomass stream from a metal-containing and chlorine-containing pyrolysis stream, comprising:
i) a pyrolysis reactor;
ii) a quench condenser configured to receive pyrolysis vapors from the pyrolysis reactor;
iii) a supply of a first metal complexing agent in communication with the quench condenser;
iv) a stirred tank configured to receive pyrolysis liquid from the quench condenser;
v) a supply of a second metal complexing agent in communication with the stirred tank and a supply of a chlorine complexing agent in communication with the stirred tank;
vi) a first filter in communication with the quench condenser and the stirred tank, the first filter configured to filter a first metal complex from a first pyrolysis liquid stream;
vi) a second filter communication with the stirred tank, the second filter configured to filter a second metal complex and a chlorine complex from a second pyrolysis liquid stream.

16. The apparatus of claim 15, wherein the quench condenser is sized to provide a liquid residence time of at least two hours.

17. The apparatus of claim 15, wherein the first metal complexing agent comprises oxalic acid.

18. The apparatus of claim 15, wherein the second metal complexing agent comprises cationic ion exchange particles.

19. The apparatus of claim 15, wherein the chlorine complexing agent comprises anionic ion exchange particles.

* * * * *